United States Patent
Ronn et al.

(10) Patent No.: US 9,657,001 B2
(45) Date of Patent: May 23, 2017

(54) COMPOUNDS AND USES

(71) Applicant: AstraZeneca AB, Sodertalje (SE)

(72) Inventors: Robert Ronn, Uppsala (SE); Carl Jonas Lindh, Uppsala (SE); Erik Ringberg, Uppsala (SE); Hanna Birgitta Ellinor Andersson, Goteborg (SE); Peter Nilsson, Stockholm (SE); Wesley Ralph Schaal, Uppsala (SE); Magnus Munck af Rosenschöld, Molndal (SE); Antonios Nikitidis, Molndal (SE); Grigorios Nikitidis, Molndal (SE); Petra Johannesson, Molndal (SE); Christian Tyrchan, Molndal (SE)

(73) Assignee: ASTRAZENECA AB, Sodertalje (SE)

( * ) Notice: Subject to any disclaimer, the term of this patent is extended or adjusted under 35 U.S.C. 154(b) by 0 days.

(21) Appl. No.: 15/146,152

(22) Filed: May 4, 2016

(65) Prior Publication Data

US 2016/0326143 A1 Nov. 10, 2016

(30) Foreign Application Priority Data

May 6, 2015 (GB) .................................. 1507753.0

(51) Int. Cl.

| | | |
|---|---|---|
| A61K 31/12 | (2006.01) | |
| C07D 405/12 | (2006.01) | |
| A61K 31/44 | (2006.01) | |
| A61K 31/4439 | (2006.01) | |
| A61K 31/496 | (2006.01) | |
| A61K 31/505 | (2006.01) | |
| C07D 213/74 | (2006.01) | |
| C07D 401/08 | (2006.01) | |
| C07D 239/42 | (2006.01) | |
| C07D 241/20 | (2006.01) | |
| C07C 211/55 | (2006.01) | |
| C07C 211/58 | (2006.01) | |
| C07D 215/38 | (2006.01) | |
| C07D 239/47 | (2006.01) | |
| C07D 401/12 | (2006.01) | |

(52) U.S. Cl.
CPC ............ *C07D 405/12* (2013.01); *A61K 31/44* (2013.01); *A61K 31/4439* (2013.01); *A61K 31/496* (2013.01); *A61K 31/505* (2013.01); *C07C 211/55* (2013.01); *C07C 211/58* (2013.01); *C07D 213/74* (2013.01); *C07D 215/38* (2013.01); *C07D 239/42* (2013.01); *C07D 239/47* (2013.01); *C07D 241/20* (2013.01); *C07D 401/08* (2013.01); *C07D 401/12* (2013.01)

(58) Field of Classification Search
USPC ......................................... 514/269, 510, 557
See application file for complete search history.

(56) References Cited

FOREIGN PATENT DOCUMENTS

| WO | 2011110824 A1 | 9/2011 | |
|---|---|---|---|
| WO | 2013151707 A1 | 10/2013 | |
| WO | WO 2013/151707 A1 * | 10/2013 | ............. A61K 31/19 |

OTHER PUBLICATIONS

International Search Report mailed for PCT/EP2016/060110 on Jul. 20, 2016.
Written Opinion mailed for PCT/EP2016/060110 on Jul. 20, 2016.
Kleinschmidt et al., 'Tandem Benzophenone Amino Pyridines, Potent and Selective Inhibitors of Human Leukotriene C4 Synthase,' J. Pharmacol. Exp Ther., vol. 355, pp. 108-116, Oct. 2015.
Xue et al., 'Prostaglandin D2 and Leukotriene E4 synergize to stimulate diverse TH2 functions and TH2 cell/neutrophil crosstalk,' J Allergy Clin Immunol., vol. 135, No. 5, pp. 1358-1366.e11, May 2015.
Xue et al., 'Leukotriene E4 Activates Human Th2 cells for exaggerated proinflammatory cytokine production in response to Prostaglandin D2,' The Journal of Immunology, vol. 188, pp. 694-702, 2012.

* cited by examiner

*Primary Examiner* — Pancham Bakshi

(57) ABSTRACT

There is provided compounds of formula I,

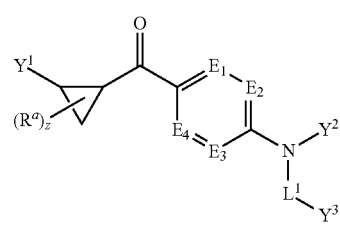

wherein $E^1$, $E^2$, $E^3$, $E^4$, $L^1$, $Y^1$, $Y^2$, $Y^3$, $R^a$ and z have meanings provided in the description, and pharmaceutically-acceptable salts thereof, which compounds are useful in the treatment of diseases in which inhibition of leukotriene $C_4$ synthase is desired and/or required, and particularly in the treatment of respiratory diseases and inflammation.

4 Claims, 1 Drawing Sheet

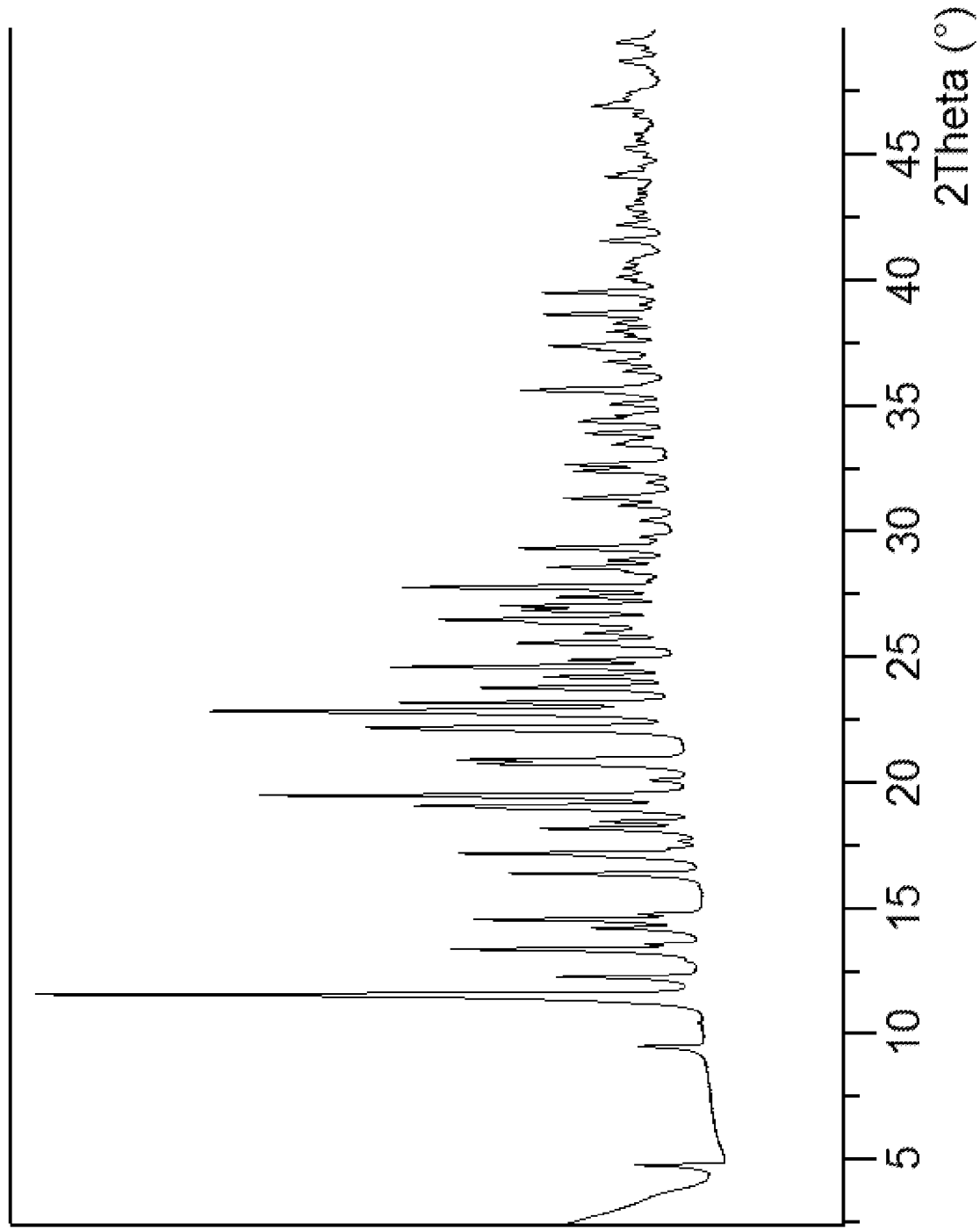

COMPOUNDS AND USES

CROSS-REFERENCE TO RELATED APPLICATIONS

This application claims the benefit under 35 U.S.C. §119 (a)-(d) to Great Britain Application No. 1507753.0 filed on 6 May 2015.

FIELD OF THE INVENTION

This invention relates to novel compounds useful as inhibitors of leukotriene C4 synthase. The compounds are of potential utility in the treatment of respiratory and/or inflammatory diseases. The invention also relates to the use of such compounds as medicaments, to pharmaceutical compositions containing them, and to synthetic routes for their production.

BACKGROUND OF THE INVENTION

Arachidonic acid is a fatty acid that is essential in the body and is stored in cell membranes. It may be converted, e.g. in the event of inflammation, into mediators, some of which are known to have beneficial properties, such as the lipoxins and resolvins and others that are harmful. Such mediators include leukotrienes (formed by the action of 5-lipoxygenase (5-LO), which act by catalysing the insertion of molecular oxygen into carbon position 5 of arachidonic acid generating 5-hydroxyeicosatetraenoic acid and then $LTA_4$), prostaglandins (which are formed by the action of cyclooxygenases (COXs)) and eoxins (formed by the action of 15-lipoxygenase (15-LO), which act by catalysing the insertion of molecular oxygen into carbon position 15), followed by conjugation with glutathione catalysed by leukotriene $C_4$ synthase. Huge efforts have been devoted towards the development of drugs that inhibit the action of some of these metabolites as well as the biological processes that form them.

Of the leukotrienes, leukotriene $(LT)B_4$ is formed by the action of 5-lipoxygenase and leukotriene $A_4$ hydrolase. $LTB_4$ is known to be involved in neutrophil recruitment and may play an important role in host defence. The cysteinyl-containing leukotrienes $C_4$, $D_4$ and $E_4$ (CysLTs), formed by the action of 5-lipoxygenase and cysteine leukotriene $C_4$ synthase, are both very potent bronchoconstrictors and proinflammatory mediators and have thus been implicated in the pathobiology of asthma. The biological activities of the CysLTs are mediated through two receptors designated $CysLT_1$, which is the preferred receptor for $LTD_4$, and $CysLT_2$, which is the preferred receptor for $LTC_4$, but the existence of additional CysLT receptors, such as $CysLT_3$, a receptor with preference for $LTE_4$, has also been proposed. Leukotriene receptor antagonists (LTRAs) have been developed for the treatment of asthma, but they are often highly selective for $CysLT_1$. It may be hypothesised that better control of asthma may be attained if the activity of all the leukotrienes at CysLT receptors could be reduced. This may be achieved by developing unselective LTRAs, but also by inhibiting the activity of proteins, e.g. enzymes, involved in the synthesis of the CysLTs; 5-LO, 5-lipoxygenase-activating protein (FLAP), and leukotriene $C_4$ synthase may be mentioned. However, 5-LO inhibitors and/or FLAP inhibitors would also decrease the formation of $LTB_4$, and pro-resolution lipids lipoxins and resolvins. In addition to inhibiting the synthesis of CysLTs, inhibition of leukotriene $C_4$ synthase will inhibit the formation of eoxins that are known proinflammatory mediators, while preserving anti-inflammatory lipids such as the lipoxins. For a review on leukotrienes in asthma, see e.g., H.-E. Claesson and S.-E. Dahlén *J. Internal Med.* 245, 205 (1999). For a review on eoxins in asthma, see e.g., H.-E. Claesson *Prostaglandins Other Lipid Mediat.* 89, 120-125 (2009).

There are many diseases/disorders that are inflammatory in their nature or have an inflammatory component. One of the major problems associated with existing treatments of inflammatory conditions is a lack of efficacy and/or the prevalence of side effects (real or perceived).

Asthma is a chronic inflammatory disease affecting 6% to 8% of the adult population of the industrialized world. In children, the incidence is even higher, being close to 10% in most countries. Asthma is the most common cause of hospitalization for children under the age of fifteen.

Treatment regimens for asthma depend upon the severity of the condition. Mild cases are either untreated or are only treated with inhaled (3-agonists). Patients with more severe asthma are typically treated with anti-inflammatory compounds on a regular basis.

There is a considerable under-treatment of asthma, which is due at least in part to perceived risks with existing maintenance therapy (mainly inhaled corticosteroids). These include risks of growth retardation in children and loss of bone mineral density, resulting in unnecessary morbidity and mortality. As an alternative to steroids, LTRAs have been developed. These drugs may be given orally, but are considerably less efficacious than inhaled steroids and usually do not control airway inflammation satisfactorily. This combination of factors has led to at least 50% of all asthma patients being inadequately treated.

A similar pattern of under-treatment exists in relation to allergic disorders, where drugs are available to treat a number of common conditions but are underused in view of apparent side effects. For instance, rhinitis, conjunctivitis and dermatitis may have an allergic component, but may also arise in the absence of underlying allergy. Indeed, non-allergic conditions of this class are in many cases more difficult to treat.

Other inflammatory disorders which may be mentioned include: chronic obstructive pulmonary disease (COPD) is a common disease affecting 6% to 8% of the world population. The disease is potentially lethal, and the morbidity and mortality from the condition is considerable. At present, there is no known pharmacological treatment capable of changing the course of COPD; pulmonary fibrosis (this is less common than COPD, but is a serious disorder with a very poor prognosis); inflammatory bowel disease (a group of disorders with a high morbidity rate—today only symptomatic treatment of such disorders is available); rheumatoid arthritis and osteoarthritis (common disabling inflammatory disorders of the joints—there are currently no curative, and only moderately effective symptomatic, treatments available for the management of such conditions); diabetes, a disease affecting over 3% of the world population, and growing, causing considerable morbidity and mortality; and cardiovascular disease.

Inflammation is also a common cause of pain. Inflammatory pain may arise for numerous reasons, such as infection, surgery or other trauma. Moreover, several malignancies have inflammatory components adding to the symptomatology of the patients. Inflammation may also play a role in cancer with leukotrienes involved in cancer cell proliferation and extending cancer cell lifetimes.

Thus, new and/or alternative treatments for respiratory and/or inflammatory disorders would be of benefit to all of the above-mentioned patient groups. In particular, there is a real and substantial unmet clinical need for an effective anti-inflammatory drug capable of treating inflammatory disorders, in particular asthma, with no real or perceived side effects.

The listing or discussion of an apparently prior-published document in this specification should not necessarily be taken as an acknowledgement that the document is part of the state of the art or is common general knowledge.

International patent publications WO 2009/030887, WO 2010/103297, WO 2010/103278, WO 2010/103279, WO 2010/103283 and WO 2011/110824 disclose bis-aromatic ketones thought to be $LTC_4$ synthase inhibitors and their potential use in the treatment of respiratory and/or inflammatory diseases. These disclosures contain no teaching or suggestion relating to the use of cyclopropyl-substituted aryl and heteroaryl ketones.

DISCLOSURE OF THE INVENTION

In a first aspect of the invention, there is provided a compound of formula I,

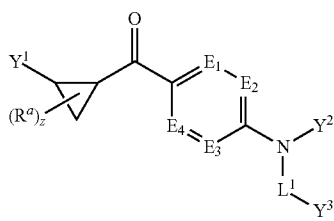

wherein:
- each of $E_1$, $E_2$, $E_3$ and $E_4$ individually represent any one of —C($R^1$)═, —C($R^2$)═, —C($R^3$)═ and —C($R^4$)═; and/or any one or two of $E_1$, $E_2$, $E_3$ and $E_4$ may independently represent —N═;
- each of $R^1$ to $R^4$ independently represents hydrogen or a substituent selected from $X^1$; and/or any one of $R^1$ to $R^4$ may independently represent —O$Y^4$; where present, each $R^a$ independently represents fluoro or $C_{1-6}$ alkyl (wherein the latter group is optionally substituted by one or more fluoro);
- z represents 0 to 4;
- $L^1$ represents a direct bond or a $C_{1-3}$ alkyl linker group, wherein the latter group is optionally substituted with one or more substituent selected from $Z^1$ and $G^1$;
- $Y^1$ represents —C(O)O$R^{1a}$, —C(O)N(H)S(O)$_2R^{1b}$ or a tetrazolyl group of the following formula,

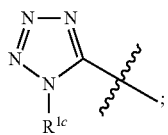

$R^{1a}$ represents:
  (i) hydrogen; or
  (ii) $C_{1-3}$ alkyl, optionally substituted by one or more fluoro;
$R^{1b}$ represents:
  A) an aryl group, optionally substituted by one or more substituents selected from $B^1$;
  B) a heteroaryl group, optionally substituted by one or more substituents selected from $B^2$; or
  C) $C_{1-8}$ alkyl or a heterocycloalkyl group, both of which are optionally substituted by one or more substituents selected from $G^2$ and/or $Z^2$;
$R^{1c}$ represents H or $C_{1-6}$ alkyl (wherein the latter group is optionally substituted by one or more substituents selected from $G^3$ and/or $Z^3$);
$Y^2$, $Y^3$ and $Y^4$ each independently represent:
  (a) an aryl group, optionally substituted by one or more substituents selected from $A^1$;
  (b) a heteroaryl group, optionally substituted by one or more substituents selected from $A^2$;
  (c) a $C_{1-12}$ alkyl (e.g. a $C_{3-12}$ cycloalkyl) or a heterocycloalkyl group, wherein the latter two groups are optionally substituted by one or more substituents selected from $G^4$ and/or $Z^4$; and/or
where $L^1$ represents a direct bond, $Y^2$ and $Y^3$ may be linked together to form, along with the atom to which they are attached, a 3- to 6-membered ring, which ring optionally contains a further heteroatom (such as nitrogen or oxygen) in addition to the nitrogen atom to which these substituents are necessarily attached, and which ring is optionally substituted by one or more substituents selected from $G^5$ and/or $Z^5$;
$A^1$ and $A^2$ independently represent, on each occasion when used herein:
  I) an aryl group, optionally substituted by one or more substituents selected from $B^3$;
  II) a heteroaryl group, optionally substituted by one or more substituents selected from $B^4$;
  III) $C_{1-8}$ alkyl or a heterocycloalkyl group, both of which are optionally substituted by one or more substituents selected from $G^6$ and/or $Z^6$; or
  IV) a $G^7$ group;
$X^1$ and $G^1$ to $G^7$ independently represent halo, —$R^{2a}$, —C(O)$R^{2b}$, —CN, —$NO_2$, —C(O)N($R^{3a}$)$R^{3b}$, —N($R^{4a}$)$R^{4b}$, —N($R^{2c}$)C(O)$R^{2d}$, —N(—$R^{2e}$)C(O)O$R^{2f}$, —O$R^{2g}$, —OS(O)$_2R^{2h}$, —S(O)$_nR^{2i}$, —OC(O)$R^{2j}$ or —S(O)$_2$N($R^{5a}$)$R^{5b}$;
n represents 0, 1 or 2;
$R^{2b}$ to $R^{2j}$, $R^{3a}$, $R^{3b}$, $R^{4a}$, $R^{4b}$, $R^{5a}$ and $R^{5b}$ independently represent, on each occasion when used herein, H or $R^{2a}$; and/or any of the pairs $R^{3a}$ and $R^{3b}$, $R^{4a}$ and $R^{4b}$, or $R^{5a}$ and $R^{5b}$ may be linked together to form, along with the atom(s) to which they are attached, a 3- to 6-membered ring, which ring optionally contains a further heteroatom (such as nitrogen or oxygen) in addition to the nitrogen atom to which these substituents are necessarily attached, and which ring is optionally substituted by one or more substituents selected from fluoro, ═O, —OH, —O$R^{7a}$ and/or $R^{7b}$;
$R^{7a}$ and $R^{7b}$ independently represent $R^{2a}$;
$R^{2a}$ represents, on each occasion when used herein:
  (i) $C_{1-6}$ alkyl optionally substituted by one or more substituents selected from fluoro, —$R^{8a}$, —CN, ═O, —O$R^{8b}$, —N($R^{8c}$)$R^{8d}$, —S(O)$_mR^{8e}$ and/or —S(O)$_2$N($R^{8f}$)$R^{8g}$;
  (ii) an aryl group, optionally substituted by one or more substituents selected from halo, —$R^{8a}$, —CN, —O$R^{8b}$, —N($R^{8c}$)$R^{8d}$, —S(O)$_mR^{8e}$ and/or —S(O)$_2$N($R^{8f}$)$R^{8g}$;
  (iii) a heteroaryl group, optionally substituted by one or more substituents selected from halo, —$R^{8a}$, —CN, —O$R^{8b}$, —N($R^{8c}$)$R^{8d}$, —S(O)$_mR^{8e}$ and/or —S(O)$_2$N($R^{8f}$)$R^{8g}$; or (iv) a heterocycloalkyl group, optionally substituted by one or more substituents selected from fluoro, —$R^{8a}$, —CN, —$OR^{8b}$, —$N(R^{8c})R^{8d}$, —$S(O)_m R^{8e}$ and/or —$S(O)_2 N(R^{8f})R^{8g}$;

m represents 0, 1 or 2;

each $R^{8a}$ to $R^{8g}$ independently represent H or $C_{1-6}$ alkyl optionally substituted by one or more substituents selected from fluoro, =O, —$OR^{11a}$ and/or —$N(R^{12a})R^{12b}$; and/or $R^{8c}$ and $R^{8d}$ and/or $R^{8f}$ and $R^{8g}$ may be linked together to form, along with the atom(s) to which they are attached, a 3- to 6-membered ring, which ring optionally contains a further heteroatom (such as nitrogen or oxygen) in addition to the nitrogen atom to which these substituents are necessarily attached, and which ring is optionally substituted by one or more substituents selected from fluoro and $C_{1-2}$ alkyl, wherein the latter group is optionally substituted by one or more fluoro atoms;

$R^{11a}$, $R^{12a}$ and $R^{12b}$ independently represent H or $C_{1-3}$ alkyl, wherein the latter group is optionally substituted by one or more fluoro atoms;

$B^1$ to $B^4$ independently represent halo, —$R^{14a}$, —C(O)$R^{14b}$, —CN, —$NO_2$, —C(O)N($R^{15a}$)$R^{15b}$, —N($R^{16a}$)$R^{16b}$, —N($R^{14c}$)C(O)$R^{14d}$, —N($R^{14e}$)C(O)O$R^{14f}$, —$OR^{14g}$, —OS(O)$_2 R^{14h}$, —S(O)$_p R^{14i}$, —OC(O)$R^{14j}$ or —S(O)$_2$N($R^{17a}$)$R^{17b}$;

p represents 0, 1 or 2;

$R^{14b}$ to $R^{14j}$, $R^{15a}$, $R^{15b}$, $R^{16a}$, $R^{16b}$, $R^{17a}$ and $R^{17b}$ independently represent, on each occasion when used herein, H or $R^{14a}$; and/or any of the pairs $R^{15a}$ and $R^{15b}$, $R^{16a}$ and $R^{16b}$, or $R^{17a}$ and $R^{17b}$ may be linked together to form, along with the atom(s) to which they are attached, a 3- to 6-membered ring, which ring optionally contains a further heteroatom (such as nitrogen or oxygen) in addition to the nitrogen atom to which these substituents are necessarily attached, and which ring is optionally substituted by one or more substituents selected from fluoro, =O, —OH, —$OR^{19a}$ and/or $R^{19b}$;

$R^{19a}$ and $R^{19b}$ independently represent $R^{14a}$;

$R^{14a}$ represents, on each occasion when used herein $C_{1-6}$ alkyl optionally substituted by one or more substituents selected from fluoro, —$R^{20a}$, —CN, =O, —$OR^{20b}$, —N($R^{20c}$)$R^{20d}$, —S(O)$_t R^{20e}$ and/or —S(O)$_2$N($R^{20f}$)$R^{20g}$;

t represents 0, 1 or 2;

$R^{20a}$ represents $C_{1-6}$ alkyl optionally substituted by one or more fluoro;

each $R^{20b}$ to $R^{20g}$ independently represents H or $C_{1-6}$ alkyl optionally substituted by one or more fluoro;

$Z^1$ to $Z^6$ independently represent, on each occasion when used herein, =O or =$NOR^{22a}$; and $R^{22a}$ represents hydrogen or $C_{1-6}$ alkyl, wherein the latter group is optionally substituted by one or more fluoro atoms, or a pharmaceutically-acceptable salt thereof, which compounds and salts are referred to hereinafter as "the compounds of the invention".

For the avoidance of doubt, the skilled person will appreciate that compounds of the invention are characterised in that they are based on cyclopropyl-substituted aryl and heteroaryl ketones. Moreover, compounds of the invention are further characterised in that:

the essential aryl or heteroaryl group requires the presence of a substituted amino group in the 4-position relative to the essential ketone; and the essential cyclopropyl group requires the presence of a carboxylate, tetrazole or sulphonamide group in the 2-position relative to the essential ketone.

Pharmaceutically-acceptable salts include acid addition salts and base addition salts. Such acid addition salts and base addition salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

Particular acid addition salts that may be mentioned include carboxylate salts (e.g. formate, acetate, trifluoroacetate, propionate, isobutyrate, heptanoate, decanoate, caprate, caprylate, stearate, acrylate, caproate, propiolate, ascorbate, citrate, glucuronate, glutamate, glycolate, α-hydroxybutyrate, lactate, tartrate, phenylacetate, mandelate, phenylpropionate, phenylbutyrate, benzoate, chlorobenzoate, methylbenzoate, hydroxybenzoate, methoxybenzoate, dinitrobenzoate, o-acetoxybenzoate, salicylate, nicotinate, isonicotinate, cinnamate, oxalate, malonate, succinate, suberate, sebacate, fumarate, malate, maleate, hydroxymaleate, hippurate, phthalate or terephthalate salts), halide salts (e.g. chloride, bromide or iodide salts), sulfonate salts (e.g. benzenesulfonate, methyl-, bromo- or chloro-benzenesulfonate, xylenesulfonate, methanesulfonate, ethanesulfonate, propanesulfonate, hydroxyethanesulfonate, 1- or 2-naphthalene-sulfonate or 1,5-naphthalenedisulfonate salts) or sulfate, pyrosulfate, bisulfate, sulfite, bisulfate, phosphate, monohydrogenphosphate, dihydrogenphosphate, metaphosphate, pyrophosphate or nitrate salts, and the like.

Particular base addition salts that may be mentioned include salts formed with alkali metals (such as Na and K salts), alkaline earth metals (such as Mg and Ca salts), organic bases (such as ethanolamine, diethanolamine, triethanolamine, tromethamine and lysine) and inorganic bases (such as ammonia and aluminium hydroxide). More particularly, base addition salts that may be mentioned include Mg, Ca and, most particularly, K and Na salts.

Compounds of the invention may contain double bonds and may thus exist as E (entgegen) and Z (zusammen) geometric isomers about each individual double bond. All such isomers and mixtures thereof are included within the scope of the invention.

Compounds of the invention may also exhibit tautomerism. All tautomeric forms and mixtures thereof are included within the scope of the invention. For example, in respect of compounds of the invention, where $Y^1$ represents a tetrazole in respect of which $R^{1c}$ represents H then the tetrazole may exist in the tautomeric forms indicated directly below.

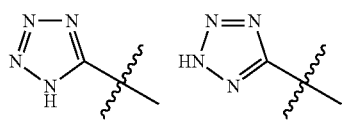 [SMILES: *c1nnn[nH]1 ; *c1nn[nH]n1]

The skilled person will understand that where a bond shown in respect of a substituent is intersected with a wavy line (such as in the structures shown directly above) or shown as a dashed line (as in respect of certain examples herein below) that bond forms the point of attachment to the other portion of the molecule.

Compounds of the invention may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution), for example with a homochiral acid followed by separation of the diastereomeric derivatives by conventional means such as chromatography, or by reaction with an appropriate chiral reagent or chiral catalyst all under conditions known to the skilled person. All stereoisomers and mixtures thereof are included within the scope of the invention. In particular, compounds of the invention may comprise asymmetric carbon atoms at the two points indicated with a dot in the structure (corresponding to compounds of formula I) shown directly below.

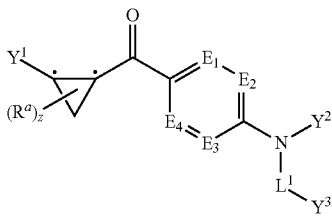

For the avoidance of doubt, the present invention includes compounds with any combination of stereochemistry in these positions. In at least one embodiment, compounds of the present disclosure include those wherein the $Y^1$ and —C(O)— substituents in these positions are in the trans configuration.

Unless otherwise specified, $C_{1-q}$ alkyl groups (where q is the upper limit of the range) defined herein may be straight-chain or, when there is a sufficient number (i.e. a minimum of two or three, as appropriate) of carbon atoms, be branched-chain, and/or cyclic (so forming a $C_{3-q}$-cycloalkyl group). Such cycloalkyl groups may be monocyclic or bicyclic and may further be bridged. Further, when there is a sufficient number (i.e. a minimum of four) of carbon atoms, such groups may also be part cyclic (for example, a $C_4$ alkyl may be represented by —CH$_2$-cyclopropyl (i.e. cyclopropylmethyl) and a $C_5$ alkyl may be represented by —CH$_2$-(1-methyl)cyclopropyl (i.e. ((1-methyl)cyclopropyl)methyl)). Such alkyl groups may also be saturated or, when there is a sufficient number (i.e. a minimum of two) of carbon atoms, be unsaturated (forming, for example, a $C_{2-q}$ alkenyl or a $C_{2-q}$ alkynyl group). Where the number of carbon atoms permits, $C_{1-q}$ alkyl groups may also be spiro-groups (i.e. two cycloalkyl rings linked together by a single common carbon atom), although more particularly they are not so. The skilled person will understand that, where an alkyl group contains a sufficient number of carbon atoms (e.g. two or three) a substituent on such a group being present on any suitable carbon atom. For example, in respect of a linker group (such as $L^1$ as herein defined) a substituent on such a group may be present on any suitable carbon atom (for example, where $L^1$ is a $C_2$ alkyl group, $L^1$ may take the form of a —(CH$_2$)$_2$— or —CH(CH$_3$)— group, which linker groups are specifically contemplated by the present invention).

The term "halo", independently at each instance when used herein, includes fluoro, chloro, bromo and iodo (for example, fluoro and chloro).

Heterocycloalkyl groups that may be mentioned include non-aromatic monocyclic and bicyclic heterocycloalkyl groups (which groups may further be bridged) in which at least one (e.g. one to four) of the atoms in the ring system is other than carbon (i.e. a heteroatom), and in which the total number of atoms in the ring system is between three and twelve (e.g. between five and ten and, most preferably, between three and eight, e.g. a 5- or 6-membered heterocycloalkyl group). Further, such heterocycloalkyl groups may be saturated or unsaturated containing one or more double and/or triple bonds, forming for example a $C_{2-q}$ (e.g. $C_{4-q}$) heterocycloalkenyl (where q is the upper limit of the range) or a $C_{7-q}$ heterocycloalkynyl group. $C_{2-q}$ heterocycloalkyl groups that may be mentioned include 7-azabicyclo-[2.2.1]heptanyl, 6-azabicyclo[3.1.1]heptanyl, 6-azabicyclo[3.2.1]-octanyl, 8-azabicyclo[3.2.1]octanyl, aziridinyl, azetidinyl, dihydropyranyl, dihydropyridyl, dihydropyrrolyl (including 2,5-dihydropyrrolyl), dioxolanyl (including 1,3-dioxolanyl), dioxanyl (including 1,3-dioxanyl and 1,4-dioxanyl), dithianyl (including 1,4-dithianyl), dithiolanyl (including 1,3-dithiolanyl), imidazolidinyl, imidazolinyl, morpholinyl, 7-oxabicyclo[2.2.1]heptanyl, 6-oxabicyclo[3.2.1]-octanyl, oxetanyl, oxiranyl, piperazinyl, piperidinyl, pyranyl, pyrazolidinyl, pyrrolidinonyl, pyrrolidinyl, pyrrolinyl, quinuclidinyl, sulfolanyl, 3-sulfolenyl, tetrahydropyranyl, tetrahydrofuranyl, tetrahydropyridyl (such as 1,2,3,4-tetrahydropyridyl and 1,2,3,6-tetrahydropyridyl), thianyl, thietanyl, thiiranyl, thiolanyl, thiomorpholinyl, trithianyl (including 1,3,5-trithianyl), tropanyl and the like. Substituents on heterocycloalkyl groups may, where appropriate, be located on any atom in the ring system including a heteroatom. Further, in the case where the substituent is another cyclic compound, then the cyclic compound may be attached through a single atom on the heterocycloalkyl group, forming a so-called "spiro"-compound. The point of attachment of heterocycloalkyl groups may be via any atom in the ring system including (where appropriate) a heteroatom (such as a nitrogen atom), or an atom on any fused carbocyclic ring that may be present as part of the ring system. Heterocycloalkyl groups may also be in the N- or S-oxidised form. At each occurrence when mentioned herein, a heterocycloalkyl group is preferably a 3- to 8-membered heterocycloalkyl group (e.g. a 5- or 6-membered heterocycloalkyl group).

For the avoidance of doubt, the term "bicyclic" (e.g. when employed in the context of heterocycloalkyl groups) refers to groups in which the second ring of a two-ring system is formed between two adjacent atoms of the first ring. The term "bridged" (e.g. when employed in the context of heterocycloalkyl groups) refers to monocyclic or bicyclic groups in which two non-adjacent atoms are linked by either an alkylene or heteroalkylene chain (as appropriate).

Aryl groups that may be mentioned include $C_{6-14}$ (such as $C_{6-13}$ (e.g. $C_{6-10}$) aryl groups. Such groups may be monocyclic or bicyclic and have between 6 and 14 ring carbon atoms, in which at least one ring is aromatic. $C_{6-14}$ aryl groups include phenyl, naphthyl and the like, such as 1,2,3,4-tetrahydronaphthyl (or 5,6,7,8-tetrahydronaphthyl), indanyl, indenyl, dihydroindenyl, dihydroacenapthylenyl, acenaphthylenyl and fluorenyl. The point of attachment of aryl groups may be via any atom of the ring system. However, when aryl groups are bicyclic or tricyclic, aryl groups that may be mentioned are those linked to the rest of the molecule via an aromatic ring.

Heteroaryl groups that may be mentioned include those which have between 5 and 14 (e.g. 10) members. Such groups may be monocyclic, bicyclic or tricyclic, provided that at least one of the rings is aromatic and wherein at least one (e.g. one to four) of the atoms in the ring system is other than carbon (i.e. a heteroatom). Heteroaryl groups that may be mentioned include oxazolopyridyl (including oxazolo[4,5-b]pyridyl, oxazolo[5,4-b]pyridyl and, in particular, oxazolo[4,5-c]pyridyl and oxazolo[5,4-c]pyridyl), thiazolopyridyl (including thiazolo[4,5-b]pyridyl, thiazolo[5,4-b]pyridyl and, in particular, thiazolo[4,5-c]pyridyl and thiazolo[5,4-c]pyridyl) and, more preferably, benzothiadiazolyl (including 2,1,3-benzothiadiazolyl), isothiochromanyl and, more preferably, acridinyl, benzimidazolyl, benzodioxanyl, benzodioxepinyl, benzodioxolyl (including 1,3-benzodioxolyl), benzofuranyl, benzofurazanyl, benzothiazolyl, benzoxadiazolyl (including 2,1,3-benzoxadiazolyl), benzoxazinyl (including 3,4-dihydro-[b][1,4]-benzoxazinyl and 4H-benzo[b][1,4]-dioxazinyl), benzoxazolyl (including benzo[d][1,3]dioxolyl), benzomorpholinyl, benzoselenadiazolyl (including 2,1,3-benzoselenadiazolyl), benzothienyl, carbazolyl, chromanyl, cinnolinyl, furanyl, imidazolyl, imidazopyridyl (such as imidazo[4,5-b]pyridyl, imidazo[5,4-b]pyridyl and, preferably, imidazo[1,2-a]pyridyl), indazolyl, indolinyl, indolyl, isobenzofuranyl, isochromanyl, isoindolinyl, isoindolyl, isoquinolinyl, isothiazolyl, isoxazolyl, naphthyridinyl (including 1,6-naphthyridinyl or, preferably, 1,5-naphthyridinyl and 1,8-naphthyridinyl), oxadiazolyl (including 1,2,3-oxadiazolyl, 1,2,4-oxadiazolyl and 1,3,4-oxadiazolyl), oxazolyl, phenazinyl, phenothiazinyl, phthalazinyl, pteridinyl, purinyl, pyrazinyl, pyrazolyl, pyridazinyl, pyridyl, pyrimidinyl, pyrrolyl, quinazolinyl, quinolinyl, quinolizinyl, quinoxalinyl, tetrahydroisoquinolinyl (including 1,2,3,4-tetrahydroisoquinolinyl and 5,6,7,8-tetrahydroisoquinolinyl), tetrahydroquinolinyl (including 1,2,3,4-tetrahydroquinolinyl and 5,6,7,8-tetrahydroquinolinyl), tetrazolyl, thiadiazolyl (including 1,2,3-thiadiazolyl, 1,2,4-thiadiazolyl and 1,3,4-thiadiazolyl), thiazolyl, thiochromanyl, thienyl, triazolyl (including 1,2,3-triazolyl, 1,2,4-triazolyl and 1,3,4-triazolyl) and the like. Substituents on heteroaryl groups may, where appropriate, be located on any atom in the ring system including a heteroatom. The point of attachment of heteroaryl groups may be via any atom in the ring system including (where appropriate) a heteroatom (such as a nitrogen atom), or an atom on any fused carbocyclic ring that may be present as part of the ring system. When heteroaryl groups are polycyclic, they are preferably linked to the rest of the molecule via an aromatic ring. Heteroaryl groups may also be in the N- or S-oxidised form.

Heteroatoms that may be mentioned include phosphorus, silicon, boron, tellurium, selenium, oxygen, nitrogen and sulphur (for example, oxygen and nitrogen).

Where the E-containing ring (as described herein) may contain more than one nitrogen atom, particular such groups that may be mentioned include those wherein the two nitrogen atoms are non-adjacent (i.e. they are not directly bonded to each other).

For the avoidance of doubt, in cases in which the identity of two or more substituents in a compound of the invention may be the same, the actual identities of the respective substituents are not in any way interdependent. For example, in the situation in which $G^1$ and $G^2$ both represent $R^{2a}$, the $R^{2a}$ groups in question may be the same or different. Similarly, when groups are substituted by more than one substituent as defined herein, the identities of those individual substituents are not to be regarded as being interdependent. For example, when there are two $X^1$ substituents present, which represent —$R^{2a}$ and —$C(O)R^{2b}$, in which $R^{2b}$ represents $R^{2a}$, then the identities of the two $R^{2a}$ groups are not to be regarded as being interdependent. Likewise, when $Y^2$ or $Y^3$ represent aryl substituted by more than one $A^1$ group, then such substituents are not interdependent (i.e. they may be the same or different $A^1$ groups).

For the avoidance of doubt, when a term such as "$R^{2b}$ to $R^{2j}$" is employed herein, this will be understood by the skilled person to mean $R^{2b}$, $R^{2c}$, $R^{2d}$, $R^{2e}$, $R^{2f}$, $R^{2g}$, $R^{2h}$, $R^{2i}$ and $R^{2j}$ inclusively. Unless otherwise stated, the same reasoning will apply to other such terms used herein.

For the avoidance of doubt, the term "$E_1$ to $E_4$-containing ring" or "E-containing ring" are synonymous and refer to the ring containing $E_1$, $E_2$, $E_3$ and $E_4$.

An embodiment of the invention include compounds of formula I wherein:
  $E_1$, $E_2$ and $E_3$ individually represent $C(R^1)$, $C(R^2)$ and $C(R^3)$ respectively and $E_4$ represents —N= (particularly wherein $R^1$ to $R^3$ are represented by hydrogen or $X^1$, or wherein $R^2$ and $R^3$ are represented by hydrogen or $X^1$ and $R^1$ is represented by —$OY^4$);
  $E_1$, $E_2$ and $E_4$ individually represent $C(R^1)$, $C(R^2)$ and $C(R^4)$ respectively and $E_3$ represents —N= (particularly wherein $R^2$ and $R^4$ are represented by hydrogen or $X^1$ and $R^1$ is represented by —$OY^4$);
  $E_1$, $E_2$, $E_3$ and $E_4$ individually represent $C(R^1)$, $C(R^2)$, $C(R^3)$ and $C(R^4)$ respectively (particularly wherein $R^2$ to $R^4$ are represented by hydrogen or $X^1$ and $R^1$ is represented by —$OY^4$);
  $E_2$ and $E_3$ individually represent $C(R^2)$ and $C(R^3)$ respectively and $E_1$ and $E_4$ each represent —N= (particularly wherein $R^3$ is represented by hydrogen or $X^1$ and $R^2$ is represented by —$OY^4$);
  $E_1$ and $E_3$ individually represent any one of $C(R^1)$, $C(R^2)$ and $C(R^4)$ and $E_2$ and $E_4$ represent —N= (particularly wherein $R^2$ and $R^4$ are represented by hydrogen and $R^1$ is represented by —$OY^4$).

Other embodiments include compounds of formula I wherein:
  $E_1$, $E_2$ and $E_3$ individually represent $C(R^1)$, $C(R^2)$ and $C(R^3)$ respectively and $E_4$ represents —N= (particularly wherein $R^1$ to $R^3$ are represented by hydrogen, or wherein $R^2$ and $R^3$ are represented by hydrogen and $R^1$ is represented by —$OY^4$);
  $E_1$, $E_2$ and $E_4$ individually represent $C(R^1)$, $C(R^2)$ and $C(R^4)$ respectively and $E_3$ represents —N= (particularly wherein $R^2$ and $R^4$ are represented by hydrogen and $R^1$ is represented by —$OY^4$);
  $E_1$, $E_2$, $E_3$ and $E_4$ individually represent $C(R^1)$, $C(R^2)$, $C(R^3)$ and $C(R^4)$ respectively (particularly wherein $R^2$ to $R^4$ are represented by hydrogen and $R^1$ is represented by —$OY^4$);
  $E_2$ and $E_3$ individually represent $C(R^2)$ and $C(R^3)$ respectively and $E_1$ and $E_4$ each represent —N= (particularly wherein $R^3$ is represented by hydrogen and $R^2$ is represented by —$OY^4$);
  $E_1$ represent $C(R^1)$ and $E_3$ represent $C(R^{1a})$ respectively and $E_2$ and $E_4$ represent —N= (particularly wherein $R^1$ is represented by —$OY^4$).

Compounds of formula I that may be mentioned include those in which at least one of $R^1$ to $R^4$ (where present) is represented by —$OY^4$.

In a particular embodiment that may be mentioned, the compound of formula I is a compound of formula Ia,

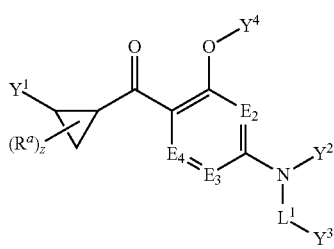

Ia wherein $Y^1$ to $Y^4$, $L^1$, $E_2$ to $E_4$, $R^a$ and z are as defined in respect of compounds of formula I.

Compounds of formula Ia that may be mentioned include those in which:
$E_2$ and $E_3$ individually represent $C(R^2)$ and $C(R^3)$ respectively and $E_4$ represents —N═; or
$E_2$ and $E_4$ individually represent $C(R^2)$ and $C(R^4)$ respectively and $E_3$ represents —N═.
$E_3$ represent $C(R^2)$ or $C(R^3)$ and $E_2$ and $E_4$ represents —N═.

Compounds of formula Ia that may be mentioned include those in which:
$E_2$ and $E_3$ individually represent $C(R^2)$ and $C(R^3)$ respectively and $E_4$ represents —N═, wherein $R^2$ and $R^3$ are represented by hydrogen; or
$E_2$ and $E_4$ individually represent $C(R^2)$ and $C(R^4)$ respectively and $E_3$ represents —N═, wherein $R^2$ and $R^4$ are represented by hydrogen.
$E_3$ represent $C(R^{1a})$ and $E_2$ and $E_4$ represents —N═.

In a further particular embodiment that may be mentioned, the compound of formula I is a compound of formula Ib

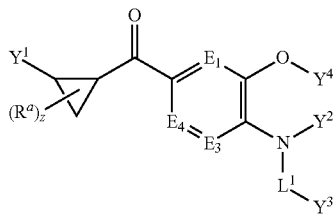

Ib wherein $Y^1$ to $Y^4$, $L^1$, $E_1$, $E_3$, $E_4$, $R^a$ and z are as defined in respect of compounds of formula I.

Particular compounds of formula Ib that may be mentioned include those in which: $E_3$ represents $C(R^3)$ and $E_1$ and $E_4$ each represent —N═.

More particular compounds of formula Ib that may be mentioned include those in which: $E_3$ represents $C(R^3)$ and $E_1$ and $E_4$ each represent —N═, wherein $R^3$ is represented by hydrogen.

For example, particular compounds of formula I that may be mentioned include those in which:
(a) $E_1$, $E_2$ and $E_3$ individually represent $C(R^1)$, $C(R^2)$ and $C(R^3)$ respectively, $E_4$ represents —N═, $R^1$ represents —$OY^4$, and $R^2$ and $R^3$ represent H,
(b) $E_1$, $E_2$ and $E_4$ individually represent $C(R^1)$, $C(R^2)$ and $C(R^4)$ respectively, $E_3$ represents —N═, $R^1$ represents —$OY^4$, and $R^2$ and $R^4$ represent H, or
(c) $E_2$ and $E_3$ individually represent $C(R^2)$ and $C(R^3)$ respectively, $E_1$ and $E_4$ each represent —N═, $R^2$ represents —$OY^4$, and $R^3$ represents H.

Particular compounds of the invention (including compounds of formula I, Ia and Ib) that may be mentioned include those in which $Y^1$ represents —C(O)OH, —C(O)N(H)S(O)$_2R^{1b}$ or tetrazol-5-yl (i.e. an unsubstituted tetrazol-5-yl wherein $R^{1c}$ represents H), particularly wherein $R^{1b}$ represents:
(a) an aryl group, optionally substituted by one or more substituents selected from $B^1$;
(b) $C_{1-6}$ (e.g. $C_{1-3}$) alkyl group, optionally substituted by one or more substituents selected from $G^2$ and/or $Z^2$.

More particular compounds of the invention (including compounds of formula I, Ia and Ib) that may be mentioned include those in which $Y^1$ represents —C(O)OH, —C(O)N(H)S(O)$_2R^{1b}$ or tetrazol-5-yl, wherein $R^{1b}$ represents:
(a) phenyl, optionally substituted by one or more (e.g. one) substituents selected from $B^1$, particularly wherein $B^1$ represents halo (such as fluoro) or —$OR^{14g}$, particularly wherein $R^{14g}$ represents $C_{1-3}$ (e.g. $C_1$) alkyl optionally substituted by one or more fluoro;
(b) a $C_{1-6}$ (e.g. $C_{1-3}$) alkyl group (such as cyclopropyl), optionally substituted by one or more fluoro (or, particularly, where the alkyl group is unsubstituted).

Particular $Y^1$ groups that may be mentioned include —C(O)OH, —C(O)N(H)S(O)$_2R^{1b}$ and tetrazol-5-yl, wherein $R^{1b}$ represents cyclopropyl, phenyl, (2-F)Ph, (4-OCH$_3$)Ph and (4-OCF$_3$)Ph.

Particular compounds of the invention (including compounds of formula I, Ia and Ib) that may be mentioned include those in which:
each $R^a$ independently represents fluoro or methyl (wherein the latter group is optionally substituted by one or more fluoro or, particularly, wherein the methyl group is unsubstituted);
z represents 0 to 4 (e.g. 4, 3, 2, 1 or 0).

More particular compounds of the invention (including compounds of formula I, Ia and Ib) that may be mentioned include those in which z represents 0 (i.e. no $R^a$ group is present).

Particular compounds of the invention (including compounds of formula I, Ia and Ib) that may be mentioned include those in which $L^1$ represents a direct bond or a $C_1$ alkyl group, wherein the latter group is optionally substituted with one or more substituent selected from ═O or, particularly, $G^1$ (such as one more fluoro).

Compounds of the invention (including compounds of formula I, Ia and Ib) that may be mentioned include those in which $L^1$ represents a direct bond or —CH$_2$—.

Particular compounds of the invention (including compounds of formula I, Ia and Ib) that may be mentioned include those in which:
$Y^2$ represents a $C_{1-6}$ (e.g. $C_{1-5}$) alkyl, straight-chain or branched-chain, optionally substituted by one or more substituents selected from $G^4$ and ═O; and
$Y^3$ represents
(a) an aryl group, optionally substituted by one or more substituents selected from $A^1$; or
(b) a heteroaryl group, optionally substituted by one or more substituents selected from $A^2$.

More particular compounds of the invention (including compounds of formula I, Ia and Ib) that may be mentioned include those in which:

$Y^2$ represents a $C_{1-5}$ alkyl, straight-chain or branched-chain, optionally substituted by one or more substituents selected from $G^4$, wherein $G^4$ represents halo (such as fluoro) or $-OR^{2g}$, wherein $R^{2g}$ represents $R^{2a}$, wherein $R^{2a}$ represents $C_{1-3}$ (e.g. $C_1$) alkyl, optionally substituted by one more fluoro; and/or $Y^3$ represents
- an aryl group (such as phenyl, naphthyl, dihydroacenaphthylenyl (e.g. 1,2-dihydroacenaphthylenyl) or dihydroindenyl (e.g. 2,3-dihydroindenyl)), optionally substituted by one or more substituents selected from $A^1$, wherein each $A^1$ independently represents:
  an aryl group (such as phenyl), wherein the latter group is optionally substituted by one or more $B^1$ group (or, particularly, wherein the aryl group is unsubstituted), a $C_{1-3}$ (e.g. $C_1$) alkyl group, wherein the latter group is optionally substituted by one or more $G^4$ group, or a $G^5$ group, particularly wherein,
  $G^4$ represents halo (such as fluoro),
  $G^5$ represents halo (such as chloro or fluoro); or
- a heteroaryl group (such as quinolinyl, 4H-benzo[d][1,3]dioxinyl or benzo[d][1,3]dioxolyl), optionally substituted by one or more substituents selected from $A^2$, wherein each $A^2$ independently represents a $C_{1-3}$ (e.g. $C_1$) alkyl group, wherein the latter group is optionally substituted by one or more $G^4$ group, or a $G^5$ group, particularly wherein,
  $G^4$ represents halo (such as fluoro),
  $G^5$ represents halo (such as chloro or fluoro).

Particular $Y^2$ groups that may be mentioned include substituted methylbutyl (for example, fluoro-methylbutyl), cyclopropylmethyl, ((1-trifluoromethyl)cyclopropyl)methyl and ((1-methyl)cyclopropyl)methyl, wherein the latter group is optionally substituted (e.g. on the 1-methyl group) with $-OCH_3$.

Particular $Y^3$ groups that may be mentioned include:
particularly where $L^1$ represents a direct bond,
- phenyl (optionally substituted with one or more chloro or methyl),
- naphthyl (e.g. naphth-1 or 2-yl; optionally substituted with one or more chloro, fluoro, $-CF_3$ or methyl),
- quinolinyl (e.g. quinolin-5 or 8-yl; optionally substituted with one or more methyl or $-CF_3$),
- dihydroindenyl (e.g. 2,3-dihydroinden-5-yl),
- dihydroacenaphthylenyl (e.g. 1,2-dihydroacenaphthylen-3 or 5-yl);

particularly where $L^1$ represents $-CH_2-$ (where optionally substituted with one or more fluoro or, particularly, unsubstituted),
- phenyl (optionally substituted with one or more methyl, $-F$, $-Cl$, $-CF_3$, -Ph),
- naphthyl (e.g. naphth-1 or 2-yl; optionally substituted with one or more methyl),
- 4H-benzo[d][1,3]dioxinyl (e.g. 4H-benzo[d][1,3]dioxin-8-yl; optionally substituted with halo, such as fluoro),
- benzo[d]dioxolyl (e.g. benzo[d]dioxol-4-yl; optionally substituted with halo, such as chloro).

Particular $X^1$ groups that may be mentioned include $-OR^{2g}$ and, more particularly, halo (such as fluoro), $-R^{2a}$, $-CN$ and $-N(R^{4a})R^{4b}$, such as fluoro.

Particular compounds of formula I that may be mentioned include those in which:
- each of $R^1$ to $R^4$ (where present) represent H; or
- any one of $R^1$ to $R^4$ (where present) represents $-OY^4$ and the remainder of $R^1$ to $R^4$ (where present) represent H.

Particular compounds of formula Ia and/or Ib that may be mentioned include those in which each of $R^1$ to $R^4$ (where present) represent H.

Particular compounds of the invention (including compounds of formula I, Ia and Ib) that may be mentioned include those in which $Y^4$ represents: a $C_{1-12}$ (e.g. $C_{1-6}$) alkyl (including a $C_{3-6}$ cycloalkyl), optionally substituted by one or more substituents selected from $G^4$ and $=O$.

More particular compounds of the invention (including compounds of formula I, Ia and Ib) that may be mentioned include those in which $Y^4$ represents methyl optionally substituted by one or more fluoro (or, more particularly, where unsubstituted).

In a particular embodiment, there is provided compounds of the invention (including compounds of formula I, Ia and Ib) wherein:
$Y^1$ represents $-C(O)OH$, $-C(O)N(H)S(O)_2R^{1b}$ or tetrazol-5-yl;
$Y^2$ represents a $C_{1-6}$ (e.g. $C_{1-5}$) alkyl, straight-chain or branched-chain, optionally substituted by one or more substituents selected from $G^4$ and $=O$;
$L^1$ represents a direct bond or a $C_1$ alkyl group, wherein the latter group is optionally substituted with one or more substituent selected from $=O$ or $G^1$;
$Y^3$ represents:
- an aryl group, optionally substituted by one or more substituents selected from $A^1$; or
- a heteroaryl group, optionally substituted by one or more substituents selected from $A^2$.
$X^1$ represents halo, $-R^{2a}$, $-N(R^{4a})R^{4b}$ and $-OR^{2g}$;
z represents 0 to 4 (particularly, 0);
$Y^4$ represents a $C_{1-6}$ alkyl (e.g. a $C_{3-6}$ cycloalkyl), optionally substituted by one or more substituents selected from $G^4$ and $=O$.

In a more particular embodiment, there is provided compounds of the invention (including compounds of formula I, Ia and Ib) wherein:
$E_1$, $E_2$ and $E_3$ individually represent $C(R^1)$, $C(R^2)$ and $C(R^3)$ respectively and $E_4$ represents $-N=$,
$E_1$, $E_2$ and $E_4$ individually represent $C(R^1)$, $C(R^2)$ and $C(R^4)$ respectively and $E_3$ represents $-N=$,
$E_1$, $E_2$, $E_3$ and $E_4$ individually represent $C(R^1)$, $C(R^2)$, $C(R^3)$ and $C(R^4)$ respectively, or
$E_2$ and $E_3$ individually represent $C(R^2)$ and $C(R^3)$ respectively and $E_1$ and $E_4$ each represent $-N=$;
$Y^1$ represents $-C(O)OH$, $-C(O)N(H)S(O)_2R^{1b}$ or tetrazol-5-yl, particularly wherein $R^{1b}$ represents:
- phenyl, optionally substituted by one or more (e.g. one) substituents selected from $B^1$, wherein $B^1$ represents halo (such as fluoro) or $-OR^{14g}$, wherein $R^{14g}$ represents $C_{1-3}$ (e.g. $C_1$) alkyl optionally substituted by one or more fluoro;
- a $C_{1-3}$ alkyl group (such as cyclopropyl), optionally substituted by one or more fluoro (or, particularly, where the alkyl group is unsubstituted);
$Y^2$ represents a $C_{1-5}$ alkyl, straight-chain or branched-chain, optionally substituted by one or more substituents selected from $G^4$, wherein $G^4$ represents halo (such as fluoro) or $-OR^{2g}$, wherein $R^{2g}$ represents $R^{2a}$, wherein $R^{2a}$ represents $C_{1-3}$ (e.g. $C_1$) alkyl, optionally substituted by one more fluoro;
$L^1$ represents a direct bond or $-CH_2-$;
$Y^3$ represents
- an aryl group (such as phenyl, naphthyl, dihydroacenaphthylenyl or dihydroindenyl), optionally substituted by one or more substituents selected from $A^1$, wherein each $A^1$ independently represents an aryl group (such as phenyl), wherein the latter group is optionally substituted by one or more $B^1$ group (or, particularly, wherein the aryl group is unsubstituted), a $C_{1-3}$ (e.g. $C_1$) alkyl group, wherein the latter group is optionally substituted by one or more $G^4$ group, or a $G^5$ group, particularly wherein,
$G^4$ represents halo (such as fluoro),
$G^5$ represents halo (such as chloro or fluoro); or
a heteroaryl group (such as quinolinyl, 4H-benzo[d][1,3]dioxinyl or benzo[d][1,3]dioxolyl), optionally substituted by one or more substituents selected from $A^2$, wherein each $A^2$ independently represents a $C_{1-3}$ (e.g. $C_1$) alkyl group, wherein the latter group is optionally substituted by one or more $G^4$ group, or a $G^5$ group, particularly wherein,
$G^4$ represents halo (such as fluoro),
$G^5$ represents halo (such as chloro or fluoro);
z represents 0 to 4 (particularly, 0);
in respect of compounds of formula I,
each of $R^1$ to $R^4$ (where present) represent H; or
any one of $R^1$ to $R^4$ (where present) represents $-OY^4$ and the remainder of $R^1$ to $R^4$ (where present) represent H;
in respect of compounds of formula Ia and/or Ib, each of $R^1$ to $R^4$ (where present) represent H; $Y^4$ represents a $C_{1-12}$ alkyl (e.g. a $C_{1-3}$ alkyl, such as methyl), optionally substituted by one or more fluoro.

In a certain embodiment that may be mentioned, there is provided compounds of formula I wherein:
$E_1$, $E_2$ and $E_3$ individually represent $C(R^1)$, $C(R^2)$ and $C(R^3)$ respectively, $E_4$ represents $-N=$, $R^1$ represents $-OY^4$, and $R^2$ and $R^3$ represent H,
$E_1$, $E_2$ and $E_4$ individually represent $C(R^1)$, $C(R^2)$ and $C(R^4)$ respectively, $E_3$ represents $-N=$, $R^1$ represents $-OY^4$, and $R^2$ and $R^4$ represent H, or
$E_2$ and $E_3$ individually represent $C(R^2)$ and $C(R^3)$ respectively, $E_1$ and $E_4$ each represent $-N=$, $R^2$ represents $-OY^4$, and $R^3$ represents H;
$Y^1$ represents $-C(O)OH$;
z represents 0;
$Y^2$ represents a $C_{1-5}$ alkyl (e.g. $-CH_2$-cyclopropyl), optionally substituted by one or more substituents selected from $G^4$,
$L^1$ represents a direct bond;
$Y^3$ represents naphthyl (e.g. napht-1-yl), optionally substituted (e.g. in the 4-position) by one or more substituents selected from $A^1$,
$Y^4$ represents a $C_{1-12}$ (e.g. $C_{1-6}$) alkyl, optionally substituted by one or more substituents selected from $G^4$ and $=O$.

In a certain embodiment that may be mentioned, there is provided compounds of formula I wherein:
$E_1$ represents $C(R^1)$, $E_2$ and $E_3$ represent $C(R^2)$, $E_4$ represents $-N=$, $R^1$ represents $-OY^4$, and $R^2$ represent H;
$Y^1$ represents $-C(O)OH$;
z represents 0;
$Y^2$ represents a $C_{1-5}$ alkyl (e.g. $-CH_2$-cyclopropyl), optionally substituted by one or more substituents selected from halo,
$L^1$ represents a direct bond;
$Y^3$ represents phenyl, optionally substituted by one or more substituents independently selected from $G^7$,
$G^7$ represents halo or $R^{2a}$; $R^{2a}$ represents $C_{1-3}$ alkyl optionally substituted by one or more substituents selected from fluoro,
$Y^4$ represents $CH_3$, $CH_2F$, $CHF_2$ or $CF_3$.

In a certain embodiment that may be mentioned, there is provided compounds of formula I wherein:
$E_1$ represents $C(R^1)$, $E_3$ represent $C(R^2)$, $E_2$ and $E_4$ represent $-N=$, $R^1$ represents $-OY^4$, and $R^2$ represent H;
$Y^1$ represents $-C(O)OH$;
z represents 0;
$Y^2$ represents a $C_{1-5}$ alkyl (e.g. $-CH_2$-cyclopropyl), optionally substituted by one or more substituents selected from halo,
$L^1$ represents a direct bond;
$Y^3$ represents phenyl, optionally substituted by one or more substituents independently selected from $G^7$,
$G^7$ represents halo or $R^{2a}$; $R^{2a}$ represents $C_{1-3}$ alkyl optionally substituted by one or more substituents selected from fluoro,
$Y^4$ represents $CH_3$, $CH_2F$, $CHF_2$ or $CF_3$.

In a certain embodiment that may be mentioned, there is provided compounds of formula I wherein:
$E_1$ represents $C(R^1)$, $E_2$ and $E_3$ represent $C(R^2)$, $E_4$ represents $-N=$, $R^1$ represents $-OY^4$, and $R^2$ represent H;
$Y^1$ represents $-C(O)OH$;
z represents 0;
$Y^2$ represents a $C_{1-5}$ alkyl (e.g. $-CH_2$-cyclopropyl), optionally substituted by one or more substituents selected from halo,
$L^1$ represents a direct bond;
$Y^3$ represents phenyl, optionally substituted by one or more substituents independently selected from $G^7$,
$G^7$ represents halo or $R^{2a}$; $R^{2a}$ represents $CH_3$, $CH_2F$, $CHF_2$ or $CF_3$,
$Y^4$ represents $CH_3$, $CH_2F$, $CHF_2$ or $CF_3$.

In a certain embodiment that may be mentioned, there is provided compounds of formula I wherein:
$E_1$ represents $C(R^1)$, $E_3$ represent $C(R^2)$, $E_2$ and $E_4$ represent $-N=$, $R^1$ represents $-OY^4$, and $R^2$ represent H;
$Y^1$ represents $-C(O)OH$;
z represents 0;
$Y^2$ represents a $C_{1-5}$ alkyl (e.g. $-CH_2$-cyclopropyl), optionally substituted by one or more substituents selected from halo,
$L^1$ represents a direct bond;
$Y^3$ represents phenyl, optionally substituted by one or more substituents independently selected from $G^7$,
$G^7$ represents halo or $R^{2a}$; $R^{2a}$ represents $CH_3$, $CH_2F$, $CHF_2$ or $CF_3$,
$Y^4$ represents $CH_3$, $CH_2F$, $CHF_2$ or $CF_3$.

In a certain embodiment that may be mentioned, there is provided compounds of formula I chosen from:
(1S,2S)-2-({5-[(5-Chloro-2,4-difluorophenyl)(2-fluoro-2-methylpropyl)amino]-3-methoxypyrazin-2-yl}carbonyl)cyclopropanecarboxylic acid;
(1R,2R)-2-({5-[(5-chloro-2,4-difluorophenyl)(2-fluoro-2-methylpropyl)amino]-3-methoxypyrazin-2-yl}carbonyl)cyclopropanecarboxylic acid;
(1S,2R)-2-({5-[(5-chloro-2,4-difluorophenyl)(2-fluoro-2-methylpropyl)amino]-3-methoxypyrazin-2-yl}) carbonyl)cyclopropanecarboxylic acid;
(1R,2S)-2-({5-[(5-chloro-2,4-difluorophenyl)(2-fluoro-2-methylpropyl)amino]-3-methoxypyrazin-2-yl}) carbonyl)cyclopropanecarboxylic acid; or a pharmaceutically acceptable salt thereof.

Particular compounds of the invention that may be mentioned include those of the examples described hereinafter, or isomers thereof or pharmaceutically-acceptable salts thereof.

Compounds of the invention may be made in accordance with techniques that are well known to those skilled in the art, for example as described hereinafter.

Methods of Preparation

According to a further aspect of the invention there is provided a process for the preparation of a compound of formula I which process comprises:

(i) oxidation of a compound of formula II,

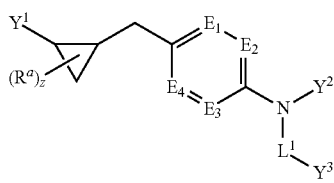

II wherein $E^1$, $E^2$, $E^3$, $E^4$, $L^1$, $Y^1$, $Y^2$, $Y^3$, $R^a$ and z are as hereinbefore defined, or a suitably protected derivative thereof, in the presence of a suitable oxidising agent as known to those skilled in the art, for example, tert-butyl hydroperoxide or sodium periodate, and optionally in the presence of a suitable catalytic additive(s) (e.g. $CrO_3$ or $RhO_4$);

(ii) oxidation of a compound of formula III,

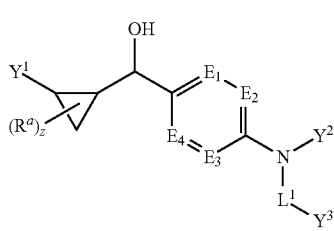

III wherein $E^1$, $E^2$, $E^3$, $E^4$, $L^1$, $Y^1$, $Y^2$, $Y^3$, $R^a$ and z are as hereinbefore defined, or a suitably protected derivative thereof, in the presence of a suitable oxidising agent, for example, manganese dioxide ($MnO_2$), 2,3-dichloro-5,6-dicyano-1,4-benzoquinone (DDQ), pyridinium chlorochromate (PCC) or the like (e.g. pyridinium dichromate (PDC));

(iii) reaction of a compound of formula IV,

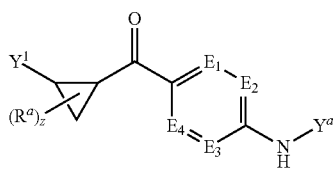

IV wherein $Y^a$ represents either of $Y^2$ or $L^1$-$Y^3$, and $E^1$, $E^2$, $E^3$, $E^4$, $L^1$, $Y^1$, $Y^2$, $Y^3$, $R^a$ and z (as appropriate) are as hereinbefore defined, or a suitably protected derivative thereof, with a compound of formula V, $Y^b$-$L^a$  V wherein $L^a$ represents a suitable leaving group such as chloro, bromo, iodo, a sulfonate group (e.g. —OS(O)$_2$CF$_3$, —OS(O)$_2$CH$_3$, —OS(O)$_2$PhMe or a nonaflate) or —B(OH)$_2$ (or a protected derivative thereof, e.g. an alkyl protected derivative, so forming, for example a 4,4,5,5-tetramethyl-1,3,2-dioxaborolan-2-yl group) and $Y^b$ represents the other of $Y^2$ or $L^1$-$Y^3$ (i.e. that not present in the compound of formula IV as described herein) and $Y^2$ or $L^1$ and $Y^3$ (as appropriate) is as hereinbefore defined, for example optionally in the presence of an appropriate metal catalyst (or a salt or complex thereof) such as Cu, Cu(OAc)$_2$, CuI (or CuI/diamine complex), copper tris(triphenyl-phosphine)bromide, Pd(OAc)$_2$, Pd$_2$(dba)$_3$ or NiCl$_2$ and an optional additive such as Ph$_3$P, 2,2'-bis(diphenylphosphino)-1, 1'-binaphthyl, xantphos, NaI or an appropriate crown ether such as 18-crown-6-benzene, in the presence of an appropriate base such as NaH, Et$_3$N, pyridine, N,N'-dimethylethylenediamine, Na$_2$CO$_3$, K$_2$CO$_3$, K$_3$PO$_4$, Cs$_2$CO$_3$, t-BuONa or t-BuOK (or a mixture thereof, optionally in the presence of 4 Å molecular sieves), in a suitable solvent (e.g. dichloromethane, dioxane, toluene, ethanol, isopropanol, dimethylformamide, ethylene glycol, ethylene glycol dimethyl ether, water, dimethylsulfoxide, acetonitrile, dimethylacetamide, N-methylpyrrolidinone, tetrahydrofuran or a mixture thereof) or in the absence of an additional solvent when the reagent may itself act as a solvent (e.g. when $Y^b$ represents phenyl and $L^a$ represents bromo, i.e. bromobenzene), and wherein the reaction may be carried out at room temperature or above (e.g. at a high temperature, such as the reflux temperature of the solvent system that is employed) and/or using microwave irradiation;

(iv) reaction of a compound of formula VI,

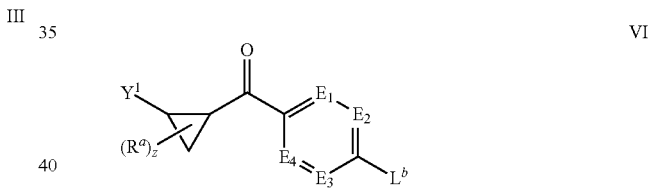

VI wherein $E^1$, $E^2$, $E^3$, $E^4$, $Y^1$, $R^a$ and z are as hereinbefore defined and $L^b$ represents a suitable leaving group, or a suitably protected derivative thereof, in which the suitable leaving group may independently be fluoro or, preferably, chloro, bromo, iodo, a sulfonate group (e.g. —OS(O)$_2$CF$_3$, —OS(O)$_2$CH$_3$, —OS(O)$_2$PhMe or a nonaflate), —B(OH)$_2$ and —B(OR$^{za}$)$_2$, in which each R$^{za}$ independently represents a $C_{1-6}$ alkyl group, or, the respective R$^{za}$ groups may be linked together to form a 4- to 6-membered cyclic group (such as a 4,4,5,5-tetramethyl-1,3,2-dioxaborolan-2-yl group), with a compound of formula VII,

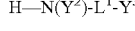H—N(Y$^2$)-L$^1$-Y$^3$  VII wherein $L^1$, $Y^2$ and $Y^3$ are as hereinbefore defined, under suitable reaction conditions known to those skilled in the art, e.g. such as those hereinbefore described in respect of process (iii) above, for example optionally in the presence of an appropriate metal catalyst (or a salt or complex thereof) such as Cu, Cu(OAc)$_2$, CuI (or CuI/diamine complex), copper tris(triphenyl-phosphine)bromide, Pd(OAc)$_2$, Pd$_2$(dba)$_3$ or NiCl$_2$ and an optional additive such as Ph$_3$P, 2,2'-bis(diphenylphosphino)-1,1'-binaphthyl, xantphos, NaI or an appropriate crown ether such as 18-crown-6-benzene, in the presence of an appropriate base such as NaH, Et$_3$N, pyridine, N,N'-dimethylethylenediamine, $Na_2CO_3$, $K_2CO_3$, $K_3PO_4$, $Cs_2CO_3$, t-BuONa or t-BuOK (or a mixture thereof, optionally in the presence of 4 Å molecular sieves), in a suitable solvent (e.g. dichloromethane, dioxane, toluene, ethanol, isopropanol, dimethylformamide, ethylene glycol, ethylene glycol dimethyl ether, water, dimethylsulfoxide, acetonitrile, dimethylacetamide, N-methylpyrrolidinone, tetrahydrofuran or a mixture thereof);

(v) for compounds of formula I that contain only saturated alkyl groups, reduction of a corresponding compound of formula I that contains an unsaturation, such as a double or triple bond, in the presence of suitable reducing conditions, for example by catalytic (e.g. employing Pd) hydrogenation;

(vi) for compounds of formula I in which $Y^1$ represents —C(O)OR$^{1a}$, in which $R^{1a}$ represents hydrogen, hydrolysis of a corresponding compound of formula I in which $R^{1a}$ does not represent hydrogen (e.g. $R^{1a}$ represents $C_{1-3}$ alkyl or a suitable benzylic group as known to those skilled in the art), under standard conditions, for example: in the presence of an aqueous solution of base (e.g. aqueous 2M NaOH) optionally in the presence of an (additional) organic solvent (such as THF or ethanol), which reaction mixture may be stirred at room or elevated temperature (e.g. about 60° C.) for a period of time until hydrolysis is complete (e.g. 5 hours); or, alternatively, using non-hydrolytic means suitable for converting esters to acids, such as by hydrogenation or oxidation (e.g. for certain benzylic groups) under conditions known to those skilled in the art;

(vii) for compounds of formula I in which $Y^1$ represents —C(O)OR$^{1a}$ and $R^{1a}$ does not represent H:
esterification (or the like) of a corresponding compound of formula I in which $R^{1a}$ represents H; or
trans-esterification (or the like) of a corresponding compound of formula I in which $R^{1a}$ does not represent H (and does not represent the same value of the corresponding $R^{1a}$ group in the compound of formula I to be prepared),
under standard conditions in the presence of the appropriate alcohol of formula VIII, $$R^{1za}OH \qquad \text{VIII}$$

wherein $R^{1za}$ represents $R^{1a}$ provided that it does not represent H, for example further in the presence of acid (e.g. concentrated $H_2SO_4$) at elevated temperature, such as at the boiling temperature of the alcohol of formula VIII;

(viii) for compounds of formula I (particularly in which $Y^1$ represents —C(O)OR$^{1a}$, wherein $R^{1a}$ is other than H), reaction of a compound of formula IX,

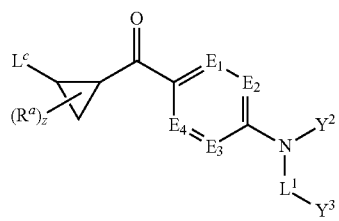

IX wherein $E^1$, $E^2$, $E^3$, $E^4$, $L^1$, $Y^2$, $Y^3$, $R^a$ and z are as hereinbefore defined, or a suitably protected derivative thereof, and L represents an appropriate alkali metal group (e.g. sodium, potassium or, especially, lithium), a —Mg-halide, an organotin group or a suitable leaving group such as halo(wherein the skilled person will appreciate that the compound of formula IX in which $L^c$ represents an alkali metal (e.g. lithium), a Mg-halide or an organotin group may be prepared from a corresponding compound of formula IX in which $L^c$ represents halo, for example under conditions such as Grignard reaction conditions, halogen-lithium exchange reaction conditions, which latter two may be followed by transmetallation, all of which reaction conditions are known to those skilled in the art), with a compound of formula X, $$L^d-Y^c \qquad \text{X}$$

wherein $Y^c$ represents —C(O)OR$^{1a}$ wherein $R^{1a}$ is as hereinbefore defined in respect of compounds of formula I, particularly in which $R^{1a}$ is other than H, and $L^d$ represents a suitable leaving group known to those skilled in the art, such as $C_{1-3}$ alkoxy and, preferably, halo (especially chloro or bromo). For example, the compound of formula X may be Cl—C(O)OR$^{1a}$. The reaction may be performed under standard reaction conditions known to those skilled in the art, for example in the presence of a polar aprotic solvent (e.g. THF or diethyl ether);

(ix) for compounds of formula I in which $Y^1$ represents —C(O)OR$^{1a}$ in which $R^{1a}$ is H, reaction of a compound of formula IX as hereinbefore defined but in which $L^c$ represents either:
an alkali metal (for example, such as one defined in respect of process step (viii) above); or
—Mg-halide (for example, wherein the halide is bromo or chloro),
with carbon dioxide, followed by acidification under standard conditions known to those skilled in the art, for example, in the presence of aqueous hydrochloric acid;

(x) for compounds of formula I in which $Y^1$ represents —C(O)OR$^{1a}$, reaction of a corresponding compound of formula IX as hereinbefore defined but in which $L^c$ is a suitable leaving group known to those skilled in the art (such as a sulfonate group (e.g. a triflate) or, preferably, a halo (e.g. bromo or iodo) group) with CO (or a reagent that is a suitable source of CO (e.g. $Mo(CO)_6$ or $Co_2(CO)_8$)), in the presence of a compound of formula XI, $$R^{1a}OH \qquad \text{XI}$$

wherein $R^{1a}$ is as hereinbefore defined, and an appropriate catalyst system (e.g. a palladium catalyst, such as $PdCl_2$, $Pd(OAc)_2$, $Pd(Ph_3P)_2Cl_2$, $Pd(Ph_3P)_4$, $Pd_2(dba)_3$ or the like) under conditions known to those skilled in the art;

(xi) reaction of a compound of formula XII,

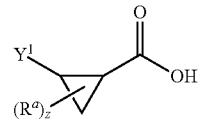

XII or a suitably protected derivative thereof (e.g. in compounds of formula I where $Y^1$ is represented by —C(O)OR$^{1a}$ it is instead represented as a suitable protecting group thereof, such as a suitable ester) with a compound of formula XIII,

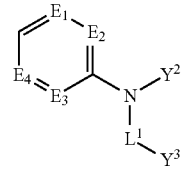

XIII wherein (in all cases and where present $E^1$, $E^2$, $E^3$, $E^4$, $L^1$, $Y^1$, $Y^2$, $Y^3$, $R^a$ and z are as hereinbefore defined, or a suitably protected derivative thereof, in the presence of a suitable reagent that converts the free carboxylic acid group of the compound of formula XII to a more reactive derivative (e.g. an acid chloride or acid anhydride, or the like; which reactive derivative may itself be separately prepared and/or isolated, or where such a reactive derivative may be prepared in situ) such as $POCl_3$, in the presence of $ZnCl_2$ or, more preferably, $PCl_3$, $PCl_5$, $SOCl_2$ or $(COCl)_2$, under conditions known to those skilled in the art, such as in the presence of a suitable solvent (e.g. DCM). Alternatively, such a reaction may be performed in the presence of a suitable catalyst (for example a Lewis acid catalyst such as $AlCl_3$) or under alternative Friedel-crafts acylation reaction conditions (or variations thereupon);

(xii) reaction of either a compound of formula XIV or XV,

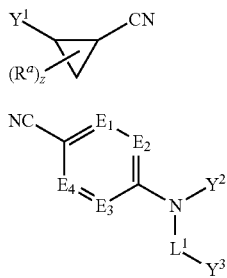

XIV with a compound of formula XVI or XVII,

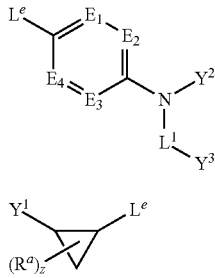

XVI

XVII respectively, wherein (in all cases and where present) $E^1$, $E^2$, $E^3$, $E^4$, $L^1$, $Y^1$, $Y^2$, $Y^3$, $R^a$ and z are as hereinbefore defined and $L^e$ represents —$B(OH)_2$ (or a protected derivative thereof as hereinbefore defined), an alkali metal (such as lithium) or a —Mg-halide (such as —MgI or, preferably, —MgBr), or a suitably protected derivative thereof, for example in the presence of a suitable solvent, optionally in the presence of a catalyst;

(xiii) reaction of an activated derivative of a compound of formula XII as hereinbefore defined (for example an acid chloride; the preparation of which is hereinbefore described in process step (xi) above), with a compound of formula XVI as hereinbefore defined, under reaction conditions known to those skilled in the art, for example those hereinbefore described in respect of process step (xii) above;

(xiv) for compounds of formula I wherein one of $R^1$ to $R^4$ represents —$OY^4$, reaction of a corresponding compound of formula I wherein the —$OY^4$ group is instead represented by —OH, with a suitable compound of formula XVIII, $Y^4$-$L^f$      XVIII wherein $Y^4$ is as hereinbefore defined in respect of compounds of formula I and $L^f$ represents a suitable leaving group such as chloro, bromo, iodo, a sulfonate group (e.g. —$OS(O)_2CF_3$, —$OS(O)_2CH_3$, —$OS(O)_2PhMe$ or a nonaflate) or —$B(OH)_2$ (or a protected derivative thereof, e.g. an alkyl protected derivative, so forming, for example a 4,4,5,5-tetramethyl-1,3,2-dioxaborolan-2-yl group), for example optionally in the presence of an appropriate metal catalyst (or a salt or complex thereof) such as Cu, $Cu(OAc)_2$, CuI (or CuI/diamine complex), copper tris(triphenyl-phosphine)bromide, $Pd(OAc)_2$, $Pd_2(dba)_3$ or $NiCl_2$ and an optional additive such as $Ph_3P$, 2,2'-bis(diphenylphosphino)-1,1'-binaphthyl, xantphos, NaI or an appropriate crown ether such as 18-crown-6-benzene, in the presence of an appropriate base such as NaH, $Et_3N$, pyridine, N,N'-dimethylethylenediamine, $Na_2CO_3$, $K_2CO_3$, $K_3PO_4$, $Cs_2CO_3$, t-BuONa or t-BuOK (or a mixture thereof, optionally in the presence of 4 Å molecular sieves), in a suitable solvent (e.g. dichloromethane, dioxane, toluene, ethanol, isopropanol, dimethylformamide, ethylene glycol, ethylene glycol dimethyl ether, water, dimethylsulfoxide, acetonitrile, dimethylacetamide, N-methylpyrrolidinone, tetrahydrofuran or a mixture thereof) or in the absence of an additional solvent when the reagent may itself act as a solvent (e.g. when $Y^4$ represents phenyl and $L^f$ represents bromo, i.e. bromobenzene), and wherein the reaction may be carried out at room temperature or above (e.g. at a high temperature, such as the reflux temperature of the solvent system that is employed) and/or using microwave irradiation;

(xv) for compounds of formula I wherein one of $R^1$ to $R^4$ represents —$OY^4$, reaction of a compound of formula XIX, or a suitably protected derivative thereof, wherein the compound of formula XIX takes the same definition as compounds of formula I with the exception that the respective $R^1$ to $R^4$ group(s) which is to represent —$OY^4$ in the compound of formula I is instead an $L_g$ group, wherein $L_g$ represents a suitable leaving group, in which the suitable leaving group may independently be chloro, bromo, iodo or, preferably, fluoro, a sulfonate group (e.g. —$OS(O)_2CF_3$, —$OS(O)_2CH_3$, —$OS(O)_2PhMe$ or a nonaflate), —$B(OH)_2$ or —$B(OR^{za})_2$, in which each $R^{za}$ independently represents a $C_{1-6}$ alkyl group, or the respective $R^{za}$ groups may be linked together to form a 4- to 6-membered cyclic group (such as a 4,4,5,5-tetramethyl-1,3,2-dioxaborolan-2-yl group), with a suitable compound of formula XX,

H—$OY^4$      XX wherein $Y^4$ is defined in respect of compounds of formula I, under suitable reaction conditions known to those skilled in the art, e.g. such as those hereinbefore described in respect of process step (iii) above, for example optionally in the presence of an appropriate metal catalyst (or a salt or complex thereof) such as Cu, $Cu(OAc)_2$, CuI (or CuI/diamine complex), copper tris(triphenyl-phosphine)bromide, $Pd(OAc)_2$, $Pd_2(dba)_3$ or $NiCl_2$ and an optional additive such as $Ph_3P$, 2,2'-bis(diphenylphosphino)-1,1'-binaphthyl, xantphos, NaI or an appropriate crown ether such as 18-crown-6-benzene, in the presence of an appropriate base such as NaH, $Et_3N$, pyridine, N,N'-dimethylethylenediamine, $Na_2CO_3$, $K_2CO_3$, $K_3PO_4$, $Cs_2CO_3$, t-BuONa or t-BuOK (or a mixture thereof, optionally in the presence of 4 Å molecular sieves), in a suitable solvent (e.g. dichloromethane, dioxane, toluene, ethanol, isopropanol, dimethylformamide, ethylene glycol, ethylene glycol dimethyl ether, water, dimethylsulfoxide, acetonitrile, dimethylacetamide, N-methylpyrrolidinone, tetrahydrofuran or a mixture thereof);

(xvi) for compounds of formula I wherein $Y^1$ represents —C(O)N(H)S(O)$_2$R$^{1b}$, reaction of a corresponding compound of formula I wherein $Y^1$ represents —C(O)OR$^{1a}$ in which R$^{1a}$ represents H, with a compound of formula XXI,

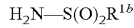

H$_2$N—S(O)$_2$R$^{1b}$   XXI wherein R$^{1b}$ is as defined in respect of compounds of formula I, under conditions known to those skilled in the art, such as under suitable peptide coupling conditions, for example in the presence of a suitable coupling reagent (such as HATU or EDC) and a suitable base (such as DIEA, DMAP and/or DBU) and in a suitable solvent (such as DMF). The skilled person will understand that the reaction may also be performed with an activated derivative of the relevant compound of formula I (for example an acid chloride; the preparation of which is hereinbefore described in process step (xi) above). Alternatively, the reaction may also be performed with a compound of formula I wherein $Y^1$ represents —C(O)OR$^{1a}$ in which R$^{1a}$ represents other than H (e.g. a C$_{1-8}$ alkyl group, such as —CH$_3$), under conditions known to those skilled in the art, such as in a suitable solvent (such as DMF) and optionally in the presence of a suitable base (such as DMAP);

(xvii) for compounds of formula I wherein $Y^1$ represents a tetrazolyl group, reaction of a compound of formula XXII,

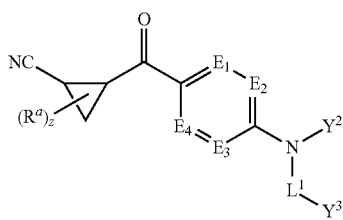

XXII wherein $E^1$, $E^2$, $E^3$, $E^4$, $L^1$, $Y^2$, $Y^3$, $R^a$ and z are as hereinbefore defined, with a suitable source of azide anion (such as sodium azide) under suitable conditions known to those skilled in the art, such as in the presence of a suitable solvent (such as toluene) and, optionally, in the presence of a suitable salt (such as triethylamine hydrochloride), followed by acidification (for example, with aq. hydrochloric acid);

(xviii) for compounds of formula I in which $Y^1$ represents —C(O)OR$^{1a}$, in which R$^{1a}$ represents hydrogen, hydrolysis of a corresponding compound of formula XXII, as hereinbefore defined, or a suitably protected derivative thereof, under standard conditions, for example in the presence of an aqueous solution of base (e.g. aqueous NaOH) optionally in the presence of an organic solvent (such as ethanol), which reaction mixture may be stirred at room or, preferably, elevated temperature (e.g. about 70° C.) for a period of time until hydrolysis is complete (e.g. 24 hours), followed by acidification using an aqueous acid (such as HCl).

Compounds of formula III may be prepared by reaction of a compound of formula XXIII,

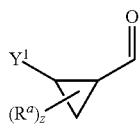

XXIII wherein $Y^1$, $R^a$ and z are as hereinbefore defined, with a compound of formula XVI, for example under reaction conditions such as those hereinbefore described in respect of preparation of compounds of formula I (process step (xii)).

Compounds of formula IV may be prepared by reaction of a compound of formula VI as hereinbefore defined with a compound of formula XXIV,

H$_2$N—Y$^a$   XXIV, wherein $Y^a$ is as hereinbefore defined in respect of compounds of formula IV, under conditions known to those skilled in the art, such as those described in respect of process step (iv) above.

Compounds of formula VI may be prepared by reactions using compounds and conditions as described in respect of process steps (xi), (xii) or (xiii) above but wherein the substituent —N(Y$^2$)-L$^1$-Y$^3$ is instead an L$^b$ group, wherein L$^b$ is as defined in respect of compounds of formula VI (or alternatively a suitable protected derivative or precursor of an L$^b$ group, wherein the process further comprises conversion of the protected derivative or precursor to the required L$^b$ group).

Compounds of formula IX may be prepared by reactions using compounds and conditions as described in respect of process steps (xi), (xii) or (xiii) above but wherein the substituent —Y$^1$ is instead an L$^c$ group, wherein L$^c$ is as defined in respect of compounds of formula IX (or alternatively a suitable protected derivative or precursor of an L$^c$ group, wherein the process further comprises conversion of the protected derivative or precursor to the required L$^c$ group).

Compounds of formula XII may be prepared by reaction of a compound of formula XVII as hereinbefore defined but in which L$^e$ represents either:
- an alkali metal (for example, such as one defined in respect of process step (viii) above); or
- —Mg-halide (for example, wherein the halide is bromo or chloro), with carbon dioxide, followed by acidification under standard conditions known to those skilled in the art, for example, in the presence of aqueous hydrochloric acid.

Compounds of formula XXIII may be prepared by reaction of a compound of formula XVII as hereinbefore defined but in which L$^e$ represents either:
- an alkali metal (for example, such as one defined in respect of process step (viii) above); or
- —Mg-halide (for example, wherein the halide is bromo or chloro), with dimethylformamide (or a similar reagent for the introduction of an aldehyde group), under standard conditions known to those skilled in the art, for example, where L$^e$ represents a —Mg-halide, under Grignard reaction conditions known to those skilled in the art (such as those described herein).

Compounds of formula II, V, VII, VIII, X, XI, XIII to XXII and XXIV are either commercially available, are known in the literature, or may be obtained either by analogy with the processes described herein, or by conventional synthetic procedures, in accordance with standard techniques, from available starting materials using appropriate reagents and reaction conditions. In this respect, the skilled person may refer to inter alia "*Comprehensive Organic Synthesis*" by B. M. Trost and I. Fleming, Pergamon Press, 1991.

The groups $E_1$ to $E_4$, $L^1$, $Y^1$ to $Y^3$ and $R_a$ (and, where relevant, $Y^4$), and substituents thereon, in final compounds of the invention or relevant intermediates may be modified one or more times, after or during the processes described above by way of methods that are well known to those skilled in the art. Examples of such methods include substitutions, reductions, oxidations, alkylations, acylations, hydrolyses, esterifications (e.g. from a carboxylic acid, e.g. in the presence of $H_2SO_4$ and appropriate alcohol or in the presence of $K_2CO_3$ and alkyl iodide), etherifications, halogenations or nitrations. The precursor groups can be changed to a different such group, or to the groups defined in formula I, at any time during the reaction sequence. For example, in cases where $Y^1$ represents —$C(O)OR^{9a}$ in which $R^{9a}$ does not initially represent hydrogen (so providing at least one ester functional group), the skilled person will appreciate that at any stage during the synthesis (e.g. the final step), the relevant $R^{9a}$-containing group may be hydrolysed to form a carboxylic acid functional group (i.e. a group in which $R^{9a}$ represents hydrogen). In this respect, the skilled person may also refer to "*Comprehensive Organic Functional Group Transformations*" by A. R. Katritzky, O. Meth-Cohn and C. W. Rees, Pergamon Press, 1995. Other specific transformation steps include: the reduction of a nitro group to an amino group; the hydrolysis of a nitrile group to a carboxylic acid group; standard nucleophilic aromatic substitution reactions, for example in which an iodo-, preferably, fluoro-, chloro- or bromo-phenyl group is converted into a cyanophenyl group by employing a source of cyanide ions (e.g. by reaction with a compound which is a source of cyano anions, e.g. sodium, copper (I), zinc or, preferably, potassium cyanide) as a reagent (alternatively, in this case, palladium catalysed cyanation reaction conditions may also be employed); the reduction of an azido group to an amino group (e.g. in the presence of $FeCl_3$ trihydrate and zinc powder); and the oxidation of a sulfide to a sulfoxide or to a sulfone (e.g. conversion of a —$SCH_3$ substituent to a —$S(O)CH_3$ or —$S(O)_2CH_3$ substituent in the presence of a suitable oxidising agent such as Oxone or meta-chloroperbenzoic acid (mCPBA)), or the reverse reduction in the presence of a suitable reducing agent.

Other transformations that may be mentioned include: the conversion of a halo group (preferably iodo or bromo) to a 1-alkynyl group (e.g. by reaction with a 1-alkyne), which latter reaction may be performed in the presence of a suitable coupling catalyst (e.g. a palladium and/or a copper based catalyst) and a suitable base (e.g. a tri-($C_{1-6}$ alkyl)amine such as triethylamine, tributylamine or ethyldiisopropylamine); the introduction of amino groups and hydroxy groups in accordance with standard conditions using reagents known to those skilled in the art; the conversion of an amino group to a halo, azido or a cyano group, for example via diazotisation (e.g. generated in situ by reaction with $NaNO_2$ and a strong acid, such as HCl or $H_2SO_4$, at low temperature such as at 0° C. or below, e.g. at about −5° C.) followed by reaction with the appropriate reagent/nucleophile e.g. a source of the relevant reagent/anion, for example by reaction in the presence of a reagent that is a source of halogen (e.g. CuCl, CuBr or NaI), or a reagent that is a source of azido or cyanide anions, such as $NaN_3$, CuCN or NaCN; the conversion of —C(O)OH to a —$NH_2$ group, under Schmidt reaction conditions, or variants thereof, for example in the presence of $HN_3$ (which may be formed in by contacting $NaN_3$ with a strong acid such as $H_2SO_4$), or, for variants, by reaction with diphenyl phosphoryl azide (($PhO)_2P(O)N_3$) in the presence of an alcohol, such as tert-butanol, which may result in the formation of a carbamate intermediate; the conversion of —$C(O)NH_2$ to —$NH_2$, for example under Hofmann rearrangement reaction conditions, for example in the presence of NaOBr (which may be formed by contacting NaOH and $Br_2$) which may result in the formation of a carbamate intermediate; the conversion of —$C(O)N_3$ (which compound itself may be prepared from the corresponding acyl hydrazide under standard diazotisation reaction conditions, e.g. in the presence of $NaNO_2$ and a strong acid such as $H_2SO_4$ or HCl) to —$NH_2$, for example under Curtius rearrangement reaction conditions, which may result in the formation of an intermediate isocyanate (or a carbamate if treated with an alcohol); the conversion of an alkyl carbamate to —$NH_2$, by hydrolysis, for example in the presence of water and base or under acidic conditions, or, when a benzyl carbamate intermediate is formed, under hydrogenation reaction conditions (e.g. catalytic hydrogenation reaction conditions in the presence of a precious metal catalyst such as Pd); halogenation of an aromatic ring, for example by an electrophilic aromatic substitution reaction in the presence of halogen atoms (e.g. chlorine, bromine, etc, or an equivalent source thereof) and, if necessary an appropriate catalyst/Lewis acid (e.g. $AlCl_3$ or $FeCl_3$).

Further, the skilled person will appreciate that the $E_1$ to $E_4$-containing ring may be a heterocycle, which moiety may be prepared with reference to a standard heterocyclic chemistry textbook (e.g. "*Heterocyclic Chemistry*" by J. A. Joule, K. Mills and G. F. Smith, $3^{rd}$ edition, published by Chapman & Hall, "*Comprehensive Heterocyclic Chemistry II*" by A. R. Katritzky, C. W. Rees and E. F. V. Scriven, Pergamon Press, 1996 or "*Science of Synthesis*", Volumes 9-17 (Hetarenes and Related Ring Systems), Georg Thieme Verlag, 2006). Hence, the reactions disclosed herein that relate to compounds containing heterocycles may also be performed with compounds that are pre-cursors to heterocycles, and which pre-cursors may be converted to those heterocycles at a later stage in the synthesis.

Further, the skilled person will understand that cyclopropane moieties present in compounds of the invention may be synthesised in accordance with techniques well-known in the art, for example as described in e-EROS Encyclopedia of Reagents for Organic Synthesis (e.g. using ethyl (dimethylsulfuranylidene)acetate).

Compounds of the invention may be isolated (or purified) from their reaction mixtures using conventional techniques (e.g. crystallisations, recrystallisations or chromatographic techniques).

It will be appreciated by those skilled in the art that, in the processes described above and hereinafter, the functional groups of intermediate compounds may need to be protected by protecting groups.

The protection and deprotection of functional groups may take place before or after a reaction in the above-mentioned schemes.

Protecting groups may be removed in accordance with techniques that are well known to those skilled in the art and as described hereinafter. For example, protected compounds/intermediates described herein may be converted chemically to unprotected compounds using standard deprotection techniques. By 'protecting group' we also include suitable alternative groups that are precursors to the actual group that it is desired to protect. For example, instead of a 'standard' amino protecting group, a nitro or azido group may be employed to effectively serve as an amino protecting group, which groups may be later converted (having served the purpose of acting as a protecting group) to the amino group, for example under standard reduction conditions described herein. Protecting groups that may be mentioned include lactone protecting groups (or derivatives thereof), which may serve to protect both a hydroxy group and an ca-carboxy group (i.e. such that the cyclic moiety is formed between the two functional groups.

The type of chemistry involved will dictate the need, and type, of protecting groups as well as the sequence for accomplishing the synthesis.

The use of protecting groups is described in e.g. *"Protective Groups in Organic Synthesis"*, $3^{rd}$ edition, T. W. Greene & P. G. M. Wutz, Wiley-Interscience (1999).

Medical and Pharmaceutical Uses

Compounds of the invention are indicated as pharmaceuticals. Therefore, according to a further aspect of the invention there is provided a compound of the invention, as hereinbefore defined, for use as a pharmaceutical and/or for use in medicine.

Although compounds of the invention may possess pharmacological activity as such, certain pharmaceutically-acceptable (e.g. "protected") derivatives of compounds of the invention may exist or be prepared which may not possess such activity, but may be administered parenterally or orally and thereafter be metabolised in the body to form compounds of the invention. Such compounds (which may possess some pharmacological activity, provided that such activity is appreciably lower than that of the "active" compounds to which they are metabolised) may therefore be described as "prodrugs" of compounds of the invention.

By "prodrug of a compound of the invention", we include compounds that form a compound of the invention, in an experimentally-detectable amount, within a predetermined time (e.g. about 1 hour), following oral or parenteral administration. All prodrugs of the compounds of the invention are included within the scope of the invention. Particular prodrugs of compounds of the invention that may be mentioned include pharmaceutically acceptable esters (for example, compounds of formula I wherein $Y^1$ represents —C(O)OR$^{1a}$, in which $R^{1a}$ is other than hydrogen).

Compounds of the invention may inhibit leukotriene (LT) $C_4$ synthase, for example as may be shown in the biological test described below, and may therefore be useful in the treatment of those conditions in which such inhibition is desired and/or required. Thus, compounds of the invention may be useful in the treatment of those conditions in which it is desired and/or required that the formation of e.g. one or more of $LTC_4$, $LTD_4$ and $LTE_4$ (such as $LTC_4$) is inhibited or decreased (or where it is required that the activation of a Cys-LT receptor (e.g. Cys-LT$_1$, Cys-LT$_2$, or CysLT$_3$) is inhibited or attenuated) and/or where it is required that the formation of one or more of eoxin (EX) $C_4$, $EXD_4$ and $EXE_4$ (such as $EXC_4$) is inhibited or decreased.

Compounds of the invention are thus expected to be useful in the treatment of disorders that may benefit from inhibition of $LTC_4$ synthase and/or inhibition of the production (i.e. synthesis and/or biosynthesis) of cysteinyl-leukotrienes (such as $LTC_4$) and/or eoxins (such as $EXC_4$), for example a respiratory disease/disorder and/or inflammation and/or a disease that has an inflammatory component.

The term "inflammation" will be understood by those skilled in the art to include any condition characterised by a localised or a systemic protective response, which may be elicited by physical trauma, infection, chronic diseases, such as those mentioned hereinbefore, and/or chemical and/or physiological reactions to external stimuli (e.g. as part of an allergic response). Any such response, which may serve to destroy, dilute or sequester both the injurious agent and the injured tissue, may be manifest by, for example, heat, swelling, pain, redness, dilation of blood vessels and/or increased blood flow, invasion of the affected area by white blood cells, loss of function and/or any other symptoms known to be associated with inflammatory conditions.

The term "inflammation" will thus also be understood to include any inflammatory disease, disorder or condition per se, any condition that has an inflammatory component associated with it, and/or any condition characterised by inflammation as a symptom, including inter alia acute, chronic, ulcerative, specific, allergic and necrotic inflammation, and other forms of inflammation known to those skilled in the art. The term thus also includes, for the purposes of this invention, inflammatory pain, pain generally and/or fever.

Accordingly, compounds of the invention may be useful in the treatment of respiratory diseases/disorders, inflammation and/or disease/disorders having an inflammatory component, for example allergic disorders, asthma, childhood wheezing, chronic obstructive pulmonary disease, bronchopulmonary dysplasia, cystic fibrosis, interstitial lung disease (e.g. sarcoidosis, pulmonary fibrosis, scleroderma lung disease, and usual interstitial in pneumonia), ear nose and throat diseases (e.g. rhinitis, nasal polyposis, and otitis media), eye diseases (e.g. conjunctivitis and giant papillary conjunctivitis), skin diseases (e.g. psoriasis, dermatitis, and eczema), rheumatic diseases (e.g. rheumatoid arthritis, arthrosis, psoriasis arthritis, osteoarthritis, systemic lupus erythematosus, systemic sclerosis), vasculitis (e.g. Henoch-Schonlein purpura, Löffler's syndrome and Kawasaki disease), cardiovascular diseases (e.g. atherosclerosis, cerebrovascular diseases, acute ischemic heart attacks and post-heart attack treatment), gastrointestinal diseases (e.g. eosinophilic diseases in the gastrointestinal system, inflammatory bowel disease, irritable bowel syndrome, colitis, celiaci and gastric haemorrhagia), urologic diseases (e.g. glomerulonephritis, interstitial cystitis, nephritis, nephropathy, nephrotic syndrome, hepatorenal syndrome, and nephrotoxicity), diseases of the central nervous system (e.g. cerebral ischemia, spinal cord injury, migraine, multiple sclerosis, and sleep-disordered breathing), endocrine diseases (e.g. autoimmune thyreoiditis, diabetes-related inflammation), urticaria, anaphylaxis, angioedema, oedema in Kwashiorkor, dysmenorrhoea, burn-induced oxidative injury, multiple trauma, pain (inflammatory and neuropathic), endotoxin shock, sepsis, bacterial infections (e.g. from *Helicobacter pylori, Pseudomonas aerugiosa* or *Shigella dysenteriae*), fungal infections (e.g. vulvovaginal candidasis), viral infections (e.g. hepatitis, meningitis, parainfluenza and respiratory syncytial virus), hypereosinofilic syndrome, and malignancies (e.g. Hodgkins lymphoma, leukemia (e.g. eosinophil leukemia and chronic myelogenous leukemia), mastocytos, polycytemi vera, and ovarian carcinoma). In particular, compounds of the invention may be useful in treating allergic disorders, asthma, rhinitis, conjunctivitis, COPD, cystic fibrosis, dermatitis, urticaria, eosinophilic gastrointestinal diseases, inflammatory bowel disease, rheumatoid arthritis, osteoarthritis and pain. Most particularly, compounds of the invention may be useful in treating asthma.

Accordingly, compounds of the invention may be useful in the treatment of cardiovascular disease in a mammal, particularly a human. Cardiovascular disease includes, but is not limited to, conditions associated with cardiac dysfunction and/or microvascular dysfunction and/or macrovascular pathology, such as atherosclerosis, arteriosclerosis, coronary artery disease including stable and high risk coronary artery disease (defined as recent acute coronary syndrome (ACS) or by biomarkers of microvascular and cardiac function), myocardial infarction, restenosis following revascularization procedures, heart failure, abdominal aortic aneurysm (AAA), peripheral artery disease (PAD) including erectile dysfunction due to vascular disease, stroke, transient ischemic attack (TIA) and reversible ischemic neurologic disease (RIND), multi-infarct dementia and renal arterial disease.

Treatment with the compounds of the invention are expected to lower the cardiovascular and/or cerebrovascular and/or renal and/or peripheral arterial disease morbidity and mortality associated with cardiac dysfunction and/or microvascular dysfunction and/or macrovascular pathology due to their anti-inflammatory properties and influence on vasoactive mechanisms.

Compounds of the invention are indicated both in the therapeutic and/or prophylactic treatment of the above-mentioned conditions.

According to a further aspect of the present invention, there is provided a method of treatment of a disease which is associated with, and/or which can be modulated by inhibition of, $LTC_4$ synthase and/or a method of treatment of a disease in which inhibition of the synthesis of cysteinyl-leukotrienes and/or eoxins (i.e. inhibition or decrease of the formation of one or more of $LTC_4$, $LTD_4$ and $LTE_4$ and/or $EXC_4$, $EXD_4$ and $EXE_4$) is desired and/or required (e.g. respiratory disorders and/or inflammation), which method comprises administration of a therapeutically effective amount of a compound of the invention, as hereinbefore defined, to a patient suffering from, or susceptible to, such a condition.

"Patients" include mammalian (including human) patients.

The term "effective amount" refers to an amount of a compound, which confers a therapeutic effect on the treated patient. The effect may be objective (i.e. measurable by some test or marker) or subjective (i.e. the subject gives an indication of or feels an effect).

Compounds of the invention will normally be administered orally, intravenously, subcutaneously, buccally, rectally, dermally, nasally, tracheally, bronchially, sublingually, by any other parenteral route or via inhalation, in a pharmaceutically acceptable dosage form.

Compounds of the invention may be administered alone, but are preferably administered by way of known pharmaceutical formulations, including tablets, capsules or elixirs for oral administration, suppositories for rectal administration, sterile solutions or suspensions for parenteral or intramuscular administration, and the like.

Such formulations may be prepared in accordance with standard and/or accepted pharmaceutical practice.

According to a further aspect of the invention there is thus provided a pharmaceutical formulation including a compound of the invention, as hereinbefore defined, in admixture with a pharmaceutically acceptable adjuvant, diluent or carrier.

Depending on e.g. potency and physical characteristics of the compound of the invention (i.e. active ingredient), pharmaceutical formulations that may be mentioned include those in which the active ingredient is present in at least 1% (or at least 10%, at least 30% or at least 50%) by weight. That is, the ratio of active ingredient to the other components (i.e. the addition of adjuvant, diluent and carrier) of the pharmaceutical composition is at least 1:99 (or at least 10:90, at least 30:70 or at least 50:50) by weight.

The invention further provides a process for the preparation of a pharmaceutical formulation, as hereinbefore defined, which process comprises bringing into association a compound of the invention, as hereinbefore defined, with a pharmaceutically-acceptable adjuvant, diluent or carrier.

Compounds of the invention may also be combined with other therapeutic agents that are useful in the treatment of a respiratory disorder (e.g. leukotriene receptor antagonists (LTRAs), glucocorticoids, antihistamines, beta-adrenergic drugs, anticholinergic drugs and $PDE_4$ inhibitors and/or other therapeutic agents that are useful in the treatment of a respiratory disorder) and/or other therapeutic agents that are useful in the treatment of inflammation and disorders with an inflammatory component (e.g. NSAIDs, coxibs, corticosteroids, analgesics, inhibitors of 5-lipoxygenase, inhibitors of FLAP (5-lipoxygenase activating protein), immunosuppressants and sulphasalazine and related compounds and/or other therapeutic agents that are useful in the treatment of inflammation).

According to a further aspect of the invention, there is provided a combination product comprising:
   a compound of the invention, as hereinbefore defined; and
   another therapeutic agent that is useful in the treatment of
      a respiratory disorder and/or inflammation,
wherein each of components (A) and (B) is formulated in admixture with a pharmaceutically-acceptable adjuvant, diluent or carrier.

Such combination products provide for the administration of a compound of the invention in conjunction with the other therapeutic agent, and may thus be presented either as separate formulations, wherein at least one of those formulations comprises a compound of the invention, and at least one comprises the other therapeutic agent, or may be presented (i.e. formulated) as a combined preparation (i.e. presented as a single formulation including a compound of the invention and the other therapeutic agent).

Thus, there is further provided:
   a pharmaceutical formulation including a compound of
      the invention, as hereinbefore defined, another therapeutic agent that is useful in the treatment of a respiratory disorder and/or inflammation, and a pharmaceutically-acceptable adjuvant, diluent or carrier; and
   a kit of parts comprising components:
      a pharmaceutical formulation including a compound of
         the invention, as hereinbefore defined, in admixture
         with a pharmaceutically-acceptable adjuvant, diluent
         or carrier; and
      a pharmaceutical formulation including another therapeutic agent that is useful in the treatment of a respiratory disorder and/or inflammation in admixture with a pharmaceutically-acceptable adjuvant, diluent or carrier,
which components (a) and (b) are each provided in a form that is suitable for administration in conjunction with the other.

The invention further provides a process for the preparation of a combination product as hereinbefore defined, which process comprises bringing into association a compound of the invention, as hereinbefore defined, with the other therapeutic agent that is useful in the treatment of a respiratory disorder and/or inflammation, and at least one pharmaceutically-acceptable adjuvant, diluent or carrier.

By "bringing into association", we mean that the two components are rendered suitable for administration in conjunction with each other.

Thus, in relation to the process for the preparation of a kit of parts as hereinbefore defined, by bringing the two components "into association with" each other, we include that the two components of the kit of parts may be:

provided as separate formulations (i.e. independently of one another), which are subsequently brought together for use in conjunction with each other in combination therapy; or packaged and presented together as separate components of a "combination pack" for use in conjunction with each other in combination therapy.

Compounds of the invention may be administered at varying doses. Oral, pulmonary and topical dosages may range from between about 0.01 mg/kg of body weight per day (mg/kg/day) to about 100 mg/kg/day, preferably about 0.01 to about 10 mg/kg/day, and more preferably about 0.1 to about 5.0 mg/kg/day. For e.g. oral administration, the compositions typically contain between about 0.01 mg to about 500 mg, and preferably between about 1 mg to about 100 mg, of the active ingredient. Intravenously, the most preferred doses will range from about 0.001 to about 10 mg/kg/hour during constant rate infusion. Advantageously, compounds may be administered in a single daily dose, or the total daily dosage may be administered in divided doses of two, three or four times daily.

In any event, the physician, or the skilled person, will be able to determine the actual dosage which will be most suitable for an individual patient, which is likely to vary with the route of administration, the type and severity of the condition that is to be treated, as well as the species, age, weight, sex, renal function, hepatic function and response of the particular patient to be treated. The above-mentioned dosages are exemplary of the average case; there can, of course, be individual instances where higher or lower dosage ranges are merited, and such are within the scope of this invention.

Compounds of the invention may have the advantage that they are effective inhibitors of $LTC_4$ synthase. Thus, compounds of the invention may have the advantage that they are able to inhibit or decrease the formation of one or more of $LTC_4$, $LTD_4$ and $LTE_4$ and/or $EXC_4$, $EXD_4$ and $EXE_4$, and therefore, are useful in the treatment of respiratory diseases/disorders, inflammation and/or disease/disorders having an inflammatory component.

Compounds of the invention may also have the advantage that they are able to effectively inhibit $LTC_4$ synthase in a human whole blood assay, mimicking the situation in humans, and may therefore be expected to have therapeutic potential in treating respiratory diseases/disorders, inflammation and/or disease/disorders having an inflammatory component. In particular, compounds of the invention may show greater inhibition of $LTC_4$ synthase in a human whole blood assay than compounds of the prior art.

In addition, compounds of the invention may have the advantage that they may be more efficacious than, be less toxic than, be longer acting than, be more potent than, produce fewer side effects than, be more easily absorbed than, and/or have a better pharmacokinetic profile (e.g. higher oral bioavailability and/or lower clearance) than, and/or have other useful pharmacological, physical, or chemical properties over, compounds known in the prior art, whether for use in the above-stated indications or otherwise.

BRIEF DESCRIPTION OF THE DRAWINGS

FIG. 1 shows the X-ray powder diffraction pattern for Example 62: (1S,2S)-2-({5-[(5-Chloro-2,4-difluorophenyl)(2-fluoro-2-methylpropyl)amino]-3-methoxypyrazin-2-yl})carbonyl)cyclopropanecarboxylic acid.

EXAMPLES

In the event that there is a discrepancy between nomenclature and any compounds depicted graphically, then it is the latter that presides (unless contradicted by any experimental details that may be given or unless it is clear from the context).

Abbreviations
aq aqueous
BINAP 2,2'-bis(diphenylphosphino)-1,1'-binaphthyl
Boc tert-butoxycarbonyl
brine saturated aqueous solution of NaClDBU 1,8-diazabicyclo[5.4.0]undec-7-ene
DEA diethylamine
DCM dichloromethaneDIEA N,N-diisopropylethylamine
DMAP 4-dimethylaminopyridine
DMF dimethylformamide
DMS dimethylsulfide
DMSO dimethylsulfoxide
EDC.HCl N-(3-dimethylaminopropyl)-N'-ethylcarbodiimide hydrochloride
ESI Electrospray Ionization
EtOAc ethyl acetate
EtOH ethanol
Ex example
FA Formic Acid
HATU O-(7-azabenzotriazolyl)-N,N,N',N'-tetramethyluronium hexafluorophosphate
HOBt 1-hydroxybenzotriazole
HPLC High Performance Liquid Chromatography
Int intermediate
KHMDS potassium bis(trimethylsilyl)amide
LAH lithium aluminium hydride
LC/MS Liquid Chromatography-Mass Spectroscopy
MeCN acetonitrile
MeOH methanolNBS N-bromosuccinimide
n-BuLi n-butyllithiumNMR nuclear magnetic resonance
$Pd_2(dba)_3$ tris(dibenzylideneacetone)dipalladium(0)
rac racemic
rt room temperature
SFC supercritical fluid chromatography
sat. saturated
tBuOK potassium tert-butoxide
tBuONa sodium tert-butoxide
TEA triethylamine
TFA trifluoroacetic acid
THF tetrahydrofuran
T3P 2,4,6-tripropyl-1,3,5,2,4,6-trioxatriphosphosphorinane-2,4,6-trioxide
Xantphos 4,5-bis(diphenylphosphino)-9,9-dimethylxanthene Experimental Procedures Unless stated otherwise, starting materials were commercially available or previously described in the literature. All solvents and commercial reagents were of laboratory grade and were used as received unless otherwise stated.

Experiments were generally carried out under inert atmosphere (nitrogen or argon), particularly in cases where oxygen- or moisture-sensitive reagents or intermediates were used. Mass spectrometry data are reported from liquid chromatography-mass spectrometry (LC-MS) using electrospray ionization. Chemical shifts for NMR data are expressed in parts per million (ppm, δ) referenced to residual peaks from the deuterated solvent used.

NMR spectra were recorded on a Bruker Avance, Avance II or Avance III spectrometer at a proton frequency of 400, 500 or 600 MHz. A JEOL EX-270 spectrometer was used if a proton frequency of 270 MHz is reported. The central peaks of $CDCl_3$ (H 7.26 ppm), acetone (H 2.04 ppm), dichloromethane-$d_2$ (H 5.32 ppm), $CH_3OD$ (H 3.30 ppm) or DMSO-$d_6$ (H 2.50 ppm) were used as internal references.

LC/MS experiments were performed using a Waters Acquity UPLC system combined with a Waters Xevo Q-ToF Mass Spectrometer in ESI mode. LC was run in two set ups: 1) BEH C18 column (1.7 μm 2.1×50 mm) in combination with a gradient (2-95% B in 5 min) of aqueous 46 mM ammonium carbonate/ammonia buffer at pH 10 (A) and MeCN (B) at a flow rate of 1.0 mL/min. 2) HSS C18 column (1.8 μm 2.1×50 mm) with a gradient (2-95% B in 5 min) of aqueous 10 mM FA/1 mM ammonium formate buffer at pH 3 (A) and MeCN (B) at a flow rate of 1.0 ml/min.

Optical purity, indicated as enantiomeric excess (% ee), was determined by chiral HPLC using an Agilent 1100 series chromatograph. Method A: System equipped with Chiralpak IC 250×4.6 mm; 5 μm. As mobile phase heptane/iPrOH/ethanolamine (60:40:0.1) with a flow rate of 1 mL/min was used. The injection volume was 10 μL and compound detection was performed by UV at 268 nm. Method B: System quipped with Chiralpak IC 150×4.6 mm, 3 μm. As mobile phase $CO_2$, 120 bar (A) and MeOH (0.5% DEA) (B) was used in a ratio A/B of 80/20 with a flow rate of 4 mL/min. The injection volume was 5 μL.

Preparative HPLC was performed with a Waters FractionLynx system with intergrated MS detection and equipped with Prep C18 OBD 5 μm 19×150 mm columns from X-Bridge or Sunfire. Alternatively Gilson GX-281 with intergrated UV detection was used, equipped with either Kromasil C8 10 μm, 20×250 ID or 50×250 ID mm. As eluent gradients of water/MeCN/AcOH (95/5/0.1) or water/0.05% TFA or water/0.1% $NH_4HCO_3$ (A) and MeCN (B) were applied.

Preparative SCF was performed with a Waters Prep 100 SCF system with intergrated MS detection, equipped with Waters Viridis 2-EP or Phenomenex Luna Hilic, 30×250 mm, 5 μm. As eluent gradients of $CO_2$ (100 g/min, 120 bar, 40° C.) (A) and MeOH/$NH_3$ (20 mM) or MeOH (5% FA) or MeOH (B) were applied.

For syntheses referencing procedures in other Examples, reaction conditions (such as length of reaction or temperature) may vary. In general, reactions were followed by thin layer chromatography or LC-MS, and subjected to work-up when appropriate. Purifications may vary between experiments: in general, solvents and the solvent ratios used for eluents/gradients were chosen to provide an appropriate $R_f$ and/or retention time.

Unless otherwise stated, example compounds described herein containing a $Y^1$ substituent on the essential cyclopropyl ring are thought to have trans configuration in respect of the $Y^1$ and ketone substituents on the relevant cyclopropyl ring.

The X-ray diffraction analysis was performed according to standard methods, which can be found in e.g. Kitaigorodsky, A. I. (1973), Molecular Crystals and Molecules, Academic Press, New York; Bunn, C. W. (1948), Chemical Crystallography, Clarendon Press, London; or Klug, H. P. & Alexander, L. E. (1974), X-ray Diffraction Procedures, John Wiley & Sons, New York.

Samples were mounted on single silicon crystal (SSC) wafer mounts and powder X-ray diffraction was recorded with a PANalytical X'Pert PRO (reflection geometry, wavelength of X-rays 1.5418 Å nickel-filtered Cu radiation, Voltage 45 kV, filament emission 40 mA). Automatic variable divergence and anti scatter slits were used and the samples were rotated during measurement. Samples were scanned from 2-50°2Theta using a 0.013° step width and 2362 seconds per step using a PIXCEL detector (active length 3.35°2Theta).

It is known that an X-ray powder diffraction pattern may be obtained which has one or more measurement errors depending on measurement conditions (such as equipment, sample preparation or machine used). In particular, it is generally known that intensities in an X-ray powder diffraction pattern may fluctuate depending on measurement conditions and sample preparation. For example, persons skilled in the art of X-ray powder diffraction will realise that the relative intensities of peaks may vary according to the orientation of the sample under test and on the type and setting of the instrument used. The skilled person will also realise that the position of reflections can be affected by the precise height at which the sample sits in the diffractometer and the zero calibration of the diffractometer. The surface planarity of the sample may also have a small effect. Hence a person skilled in the art will appreciate that the diffraction pattern data presented herein is not to be construed as absolute and any crystalline form that provides a power diffraction pattern substantially identical to those disclosed herein fall within the scope of the present disclosure (for further information see Jenkins, R & Snyder, R. L. 'Introduction to X-Ray Powder Diffractometry' John Wiley & Sons, 1996).

Generally, a measurement error of a diffraction angle in an X-ray powder diffractogram may be approximately +/−0.1°2-theta, and such a degree of a measurement error should be taken into account when considering the X-ray powder diffraction data.

Where applicable, compound names indicated in respect of examples 1-61 have been generated using the structure naming function of ChemBioDraw Ultra, Version 12.0, and the names for the examples 62-65 have been generated using the IUPAC name program ACD/Name 2014 from Acdlabs.

Preparation of intermediates used in the synthesis of compounds of the invention Scheme A

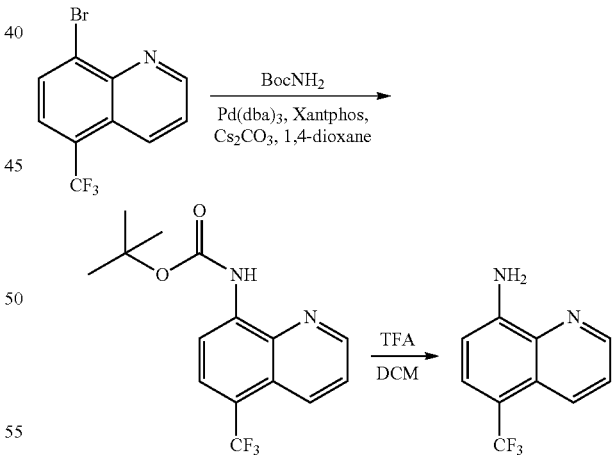

Int 1:1 5-(Trifluoromethyl)quinolin-8-amine tert-Butyl (5-(trifluoromethyl)quinolin-8-yl)carbamate 8-Bromo-5-trifluoromethyl-quinoline (50 mg, 0.18 mmol), carbamic acid tert-butyl ester (32 mg, 0.27 mmol), $Pd_2(dba)_3$ (8.2 mg, 0.010 mmol), Xantphos (15.6 mg, 0.027 mmol) and $Cs_2CO_3$ (117 mg, 0.36 mmol) were mixed in 1,4-dioxane (1 mL) and stirred at 105-110° C. for 44 h in a sealed tube. The reaction mixture was diluted (EtOAc), filtered through a celite pad and concentrated. Purification by column chromatography afforded the sub-title compound. Yield: 39 mg (69%).

5-(Trifluoromethyl)quinolin-8-amine

A solution of tert-butyl (5-(trifluoromethyl)quinolin-8-yl) carbamate (65 mg, 0.21 mmol) in DCM (2 mL) and TFA (1 mL) was stirred at rt for 1.5 h, concentrated and redissolved in EtOAc. Extractive workup (saturated aq NaHCO$_3$, water, brine) and concentration of the EtOAc extracts afforded the title compound. Yield: 47 mg (100%).

Scheme B-1

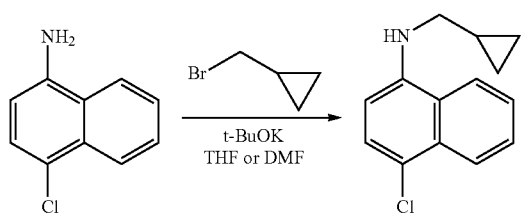

Int 2:1
4-Chloro-N-(cyclopropylmethyl)naphthalen-1-amine

To solution of 4-chloro-naphthalen-1-ylamine (1.00 g, 5.63 mmol) in THF (7 mL), tBuOK (695 mg, 6.19 mmol) was added at 0° C. in one portion. After stirring at 0° C. for 30 min, (bromomethyl)cyclopropane (0.58 mL, 5.91 mmol) was added. The reaction mixture was stirred at 0° C. for 30 min and then quenched with water. Extractive workup (EtOAc, water, brine) and concentration of the EtOAc extracts followed by column chromatography afforded the title compound. Yield 8.26 g (51%).

Scheme B-2

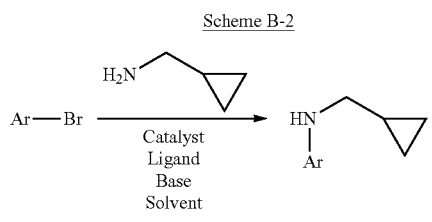

A detailed illustrative synthetic procedure for the general procedure shown in Scheme B-2 is described for synthesis of Int 2:2 below.

Int 2:2
N-(Cyclopropylmethyl)-4-methylnaphthalen-1-amine

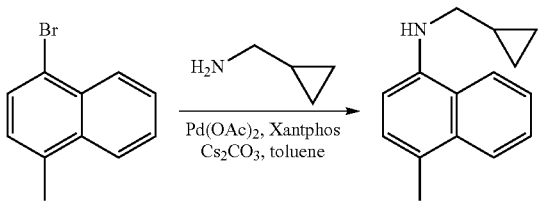

To a 100 mL round-bottom flask were added 1-bromo-4-methylnaphthalene (3.32 g, 15.0 mmol), cyclopropylmethanamine (2.67 mg, 37.5 mmol) and toluene (50 mL) to give a slightly turbid mixture. A premixed solution of Pd(OAc)$_2$ (168 mg, 0.75 mmol) and Xantphos (651 mg, 1.12 mmol) in toluene (25 mL) was added to the reaction mixture followed by Cs$_2$CO$_3$ (9.78 g, 30.0 mmol). The round-bottom flask was sealed with a rubber septum and heated at 110° C. under stirring over night. The solvent was evaporated in vacuo and the product was purified by silica chromatography (isohexane:EtOAc 95:5) to provide 2.35 g (74% yield) of the desired product as a colorless oil.

The following intermediates were prepared in analogy to Int 2:2 described above in detail unless otherwise indicated.

TABLE 1

| Int | Structure | Name | Reaction conditions according to Scheme B-2 |
|---|---|---|---|
| 2:3 | (HN-cyclopropylmethyl on 4-fluoronaphthalen-1-yl) | N-(Cyclopropylmethyl)-4-fluoronaphthalen-1-amine | Pd(OAc)$_2$, BINAP, Cs$_2$CO$_3$, toluene, 90° C. |
| 2:4 | (HN-cyclopropylmethyl on 4-methylquinolin-8-yl) | N-(Cyclopropylmethyl)-4-methylquinolin-8-amine | Pd(OAc)$_2$, Xantphos, Cs$_2$CO$_3$, toluene, 90° C. |

Scheme B-3

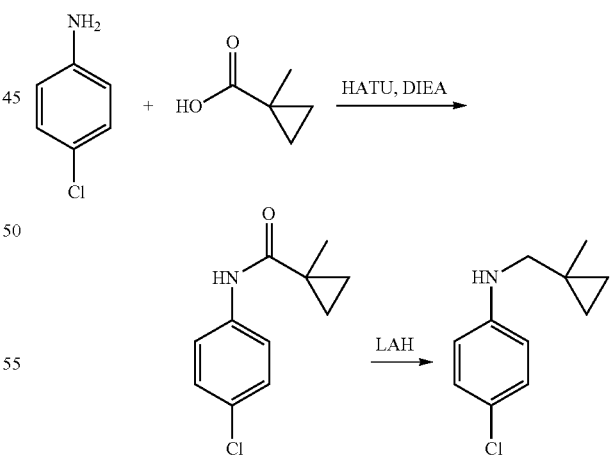

Int 2:5
4-Chloro-N-((1-methylcyclopropyl)methyl)aniline

N-(4-Chlorophenyl)-1-methylcyclopropanecarboxamide

1-Methylcyclopropanecarboxylic acid (1.04 g, 10.4 mmol), 4-chloroaniline (1.92 g, 15.1 mmol), HATU (4.28 g, 11.3 mmol), DIEA (4.0 mL, 23.0 mmol) and DCM (18 mL) was stirred overnight in a sealed reaction tube. The mixture was concentrated and the residue purified by column chromatography to afford the sub-title compound. Yield: 2.01 g (94%).

4-Chloro-N-((1-methylcyclopropyl)methyl)aniline

LAH (0.69 g, 18.2 mmol) was added in portions to a stirred solution of N-(4-chlorophenyl)-1-methylcyclopropanecarboxamide (2.01 g, 9.60 mmol) in THF (35 mL) at 0° C. After stirring at temperatures between 22-40° C. for 42 h the reaction mixture was cooled to 0° C. and quenched by addition of $H_2O$ (0.7 mL), 15% aqueous NaOH (0.7 mL) and $H_2O$ (2.1 mL). The mixture was filtered and concentrated, and the resulting residue was purified by column chromatography to afford the title compound. Yield: 1.26 g (67%).

The following intermediates were prepared in analogy to Int 2:5 described above in detail.

TABLE 2

| Int | Structure | Name |
|---|---|---|
| 2:6 | 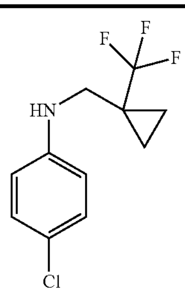 | 4-Chloro-N-((1-(trifluoromethyl)cyclopropyl)methyl)aniline |
| 2:7 | 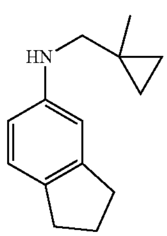 | N-((1-Methylcyclopropyl)methyl)-2,3-dihydro-1H-inden-5-amine |

Scheme B-4

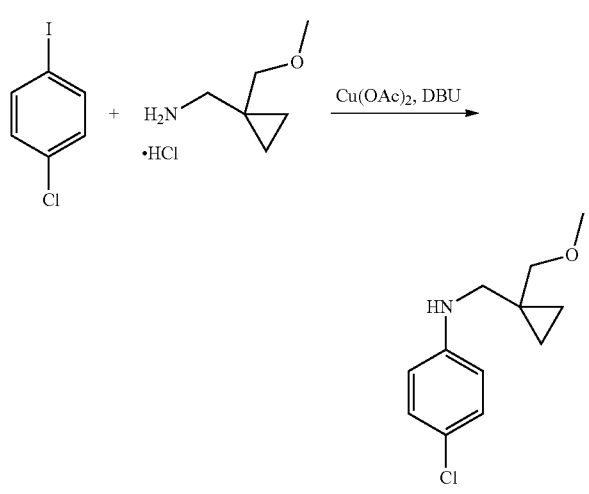

Int 2:8 4-Chloro-N-((1-(methoxymethyl)cyclopropyl)methyl)aniline

A solution of (1-(methoxymethyl)cyclopropyl)methanamine hydrochloride (385 mg, 2.54 mmol) and DBU (0.79 mL, 5.28 mmol) in DMSO (1.5 mL) was added in one portion to a mixture of 1-chloro-4-iodobenzene (373 mg, 1.56 mmol) and $Cu(OAc)_2$ (311 mg, 1.71 mmol) in DMSO (2.5 mL). The reaction mixture was heated to 150° C. for 1 h, and then cooled to rt. Extractive workup (toluene, water) and concentration of the toluene extracts followed by column chromatography afforded the title compound. Yield: 140 mg (40%).

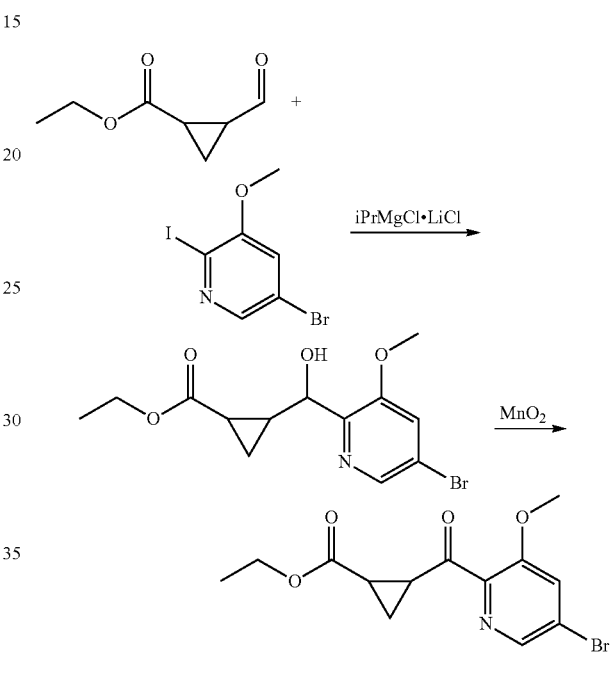

Int 3:1 Ethyl 2-(5-bromo-3-methoxypicolinoyl)cyclopropanecarboxylate

Ethyl 2-((5-bromo-3-methoxypyridin-2-yl)(hydroxy)methyl)cyclopropanecarboxylate

To an oven-dried 250 mL round-bottom flask were added 5-bromo-2-iodo-3-methoxypyridine (12.6 g, 40.0 mmol) and THF (100 mL). The reaction mixture was stirred at rt until all solid material was completely dissolved. The round-bottom flask was transferred to a cooling bath and cooled to −70° C. After cooling for 1 h at −70° C., iPrMgCl.LiCl complex in THF (1.3 M, 33.9 mL, 44.1 mmol) was added dropwise over 30 min. The temperature was slowly raised to −20° C. and kept constant for 1 h after which it was lowered to −70° C. After cooling the reaction mixture at −70° C. for 30 min ethyl 2-formylcyclopropanecarboxylate (5.80 g, 41.0 mmol) was added dropwise to the reaction mixture. The reaction mixture was allowed to slowly reach rt over night. After addition of HOAc (5 mL) under stirring, the reaction mixture was filtered through a short silica column and the column was thoroughly washed with EtOAc. The solvent was evaporated from the reaction mixture in vacuo. The crude reaction mixture was dissolved in DCM and purified by silica chromatography (isohexane:EtOAc 4:1) to give 9.34 g (71% yield) of a yellow-orange solid.

Ethyl 2-(5-bromo-3-methoxypicolinoyl)cyclopropanecarboxylate

Ethyl 2-((5-bromo-3-methoxypyridin-2-yl)(hydroxy)methyl)cyclopropanecarboxylate (9.34 g, 28.3 mmol) was dissolved in THF (200 mL) and MnO$_2$ (24.6 g, 283 mmol) was added under stirring. The reaction mixture was stirred at rt over night. The reaction mixture was filtered and the filter was thoroughly washed with EtOAc. The filtrate was concentrated in vacuo and subjected to silica chromatography (isohexane:EtOAc 1:1) to provide 8.68 g (94% yield) of the title product as a pale yellow solid.

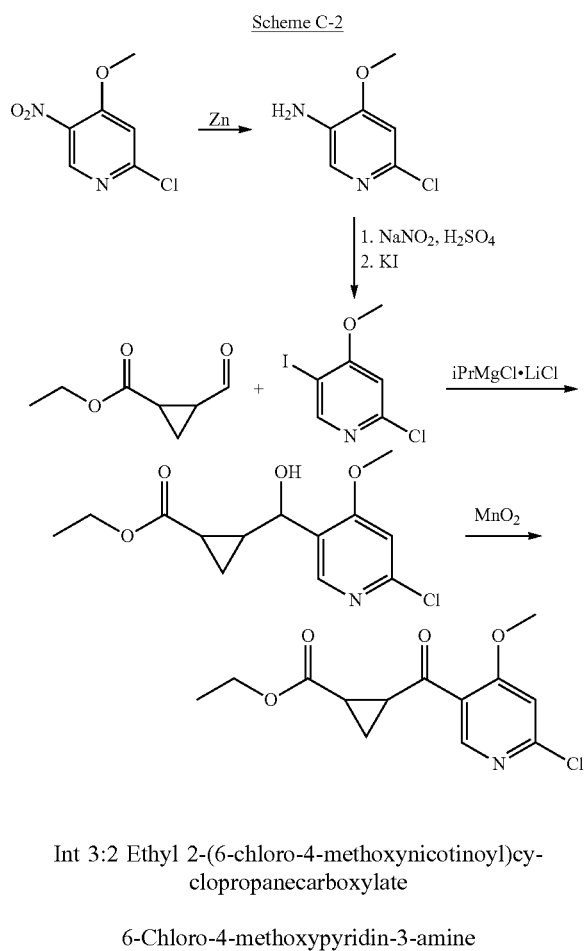

Int 3:2 Ethyl 2-(6-chloro-4-methoxynicotinoyl)cyclopropanecarboxylate

6-Chloro-4-methoxypyridin-3-amine

To solution of 2-chloro-4-methoxy-5-nitropyridine (2.00 g, 10.6 mmol) in THF (66 mL), Zn dust (3.5 g, 53 mmol) and aq NH$_4$OH (24%, 22 mL) was added at 0° C. The mixture was stirred at 7° C. for 4 h, and then filtered through a celite pad. Extractive workup of the filtrate (EtOAc, water, brine) and concentration of the EtOAc extracts followed by column chromatography afforded the sub-title compound. Yield: 1.50 g (89%).

2-Chloro-5-iodo-4-methoxypyridine

A solution of NaNO$_2$ (0.72 g, 10.5 mmol) in H$_2$O (3 mL) was added dropwise to a solution of 6-chloro-4-methoxypyridin-3-amine (1.39 g, 8.75 mmol) in H$_2$O (60 mL) and H$_2$SO$_4$ (8.7 mL) at 0° C. After stirring at 0° C. for 1 h a solution of KI (1.89 g, 11.4 mmol) in H$_2$O (9 mL) was added dropwise. The reaction mixture was stirred at rt for 1.5 h. Extractive workup (EtOAc, 1M NaOH, 10% Na$_2$S$_2$O$_3$, 1M HCl, brine) and concentration of the EtOAc extracts followed by column chromatography afforded the sub-title compound. Yield: 1.46 g (62%).

Ethyl 2-((6-chloro-4-methoxypyridin-3-yl)(hydroxy)methyl)cyclopropanecarboxylate A solution of iPrMgCl.LiCl complex in THF (1.3 M, 3.80 mL, 4.97 mmol) was added dropwise to a solution of 2-chloro-5-iodo-4-methoxypyridine (1.03 g, 3.82 mmol) in THF (6 mL) at −20° C. After stirring at −20° C. for 2 h, ethyl 2-formylcyclopropanecarboxylate (0.66 mL, 4.97 mmol) was added dropwise at −20° C. The reaction mixture was allowed to reach rt, then quenched with saturated aq NH$_4$Cl. Extractive workup (EtOAc, water, brine) and concentration of the EtOAc extracts followed by column chromatography afforded the sub-title compound. Yield: 1.20 g (94%).

Ethyl 2-(6-chloro-4-methoxynicotinoyl)cyclopropanecarboxylate

MnO$_2$ (3.65 g, 40.2 mmol) was added to a solution of ethyl 2-((6-chloro-4-methoxypyridin-3-yl)(hydroxy)methyl)cyclopropanecarboxylate (1.20 g, 4.20 mmol) in toluene (3 mL). After stirring at 70° C. for 18 h, the reaction mixture was filtered through a silicagel pad. Concentration of the filtrate followed by column chromatography afforded the sub-title compound. Yield: 0.77 g (65%).

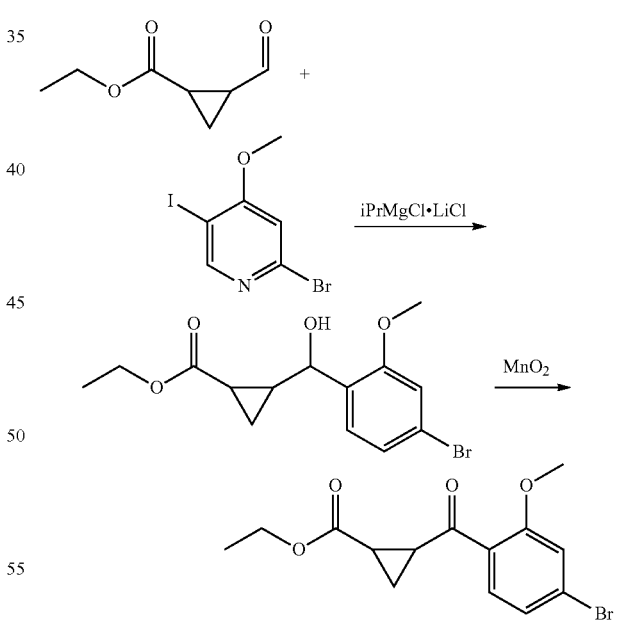

Int 3:3 Ethyl 2-(4-bromo-2-methoxybenzoyl)cyclopropanecarboxylate

Ethyl 2-((4-bromo-2-methoxyphenyl)(hydroxy)methyl)cyclopropanecarboxylate

A solution of iPrMgCl.LiCl complex in THF (1.3 M, 10.3 mL, 13.4 mmol) was added dropwise to a solution of 4-bromo-1-iodo-2-methoxybenzene (4.00 g, 12.8 mmol) in THF (25 mL) at −50° C. After stirring at −50° C. for 2 h, the reaction mixture was cooled to −70° C. and ethyl 2-formylcyclopropanecarboxylate (1.80 mL, 13.4 mmol) was added dropwise at −70° C. The reaction mixture was allowed to reach rt, then quenched with saturated aq NH$_4$Cl. Extractive workup (EtOAc, water, brine) and concentration of the EtOAc extracts followed by column chromatography afforded the sub-title compound. Yield: 3.14 g (75%).

Ethyl 2-(4-bromo-2-methoxy-benzoyl)cyclopropanecarboxylate

MnO$_2$ (8.29 g, 95.4 mmol) was added to a solution of ethyl 2-((4-bromo-2-methoxyphenyl)(hydroxy)methyl)cyclopropanecarboxylate (3.14 g, 9.54 mmol) in toluene (12 mL). After stirring at 80° C. for 16 h, the reaction mixture was filtered through a silicagel pad. Concentration of the filtrate followed by column chromatography afforded the sub-title compound. Yield: 2.40 g (77%).

Scheme C-4

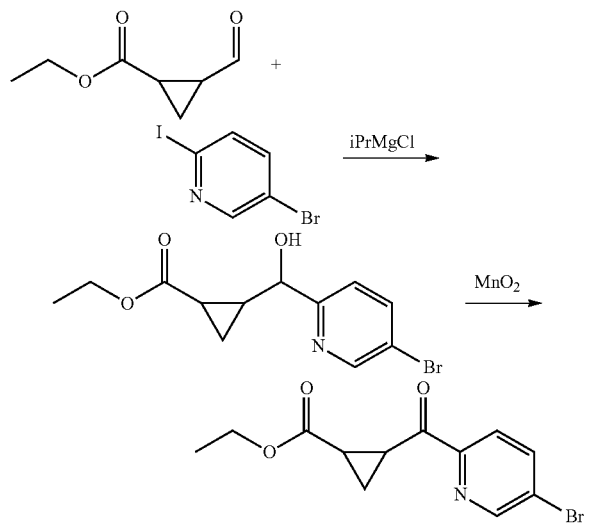

Int 3:4 Ethyl 2-(5-bromopicolinoyl)cyclopropanecarboxylate

Ethyl 2-((5-bromopyridin-2-yl)(hydroxy)methyl)cyclopropanecarboxylate

Prepared in analogy to Int 3:3 (step a) using 5-bromo-2-iodopyridine (0.60 g, 2.11 mmol), ethyl 2-formylcyclopropanecarboxylate (0.30 mL, 2.30 mmol), iPrMgCl (2 M, 1.11 mL, 2.22 mmol) and THF (15 mL) at −30° C. Yield: 0.30 g (47%).

Ethyl 2-(5-bromopicolinoyl)cyclopropanecarboxylate

Prepared in analogy to Int 3:3 (step b) using ethyl 2-((5-bromopyridin-2-yl)(hydroxy)methyl)cyclopropanecarboxylate (0.30 g, 0.95 mmol), MnO$_2$ (285 mg, 3.29 mmol) and toluene (8 mL) at 50° C. for 16 h. Yield: 0.22 g (78%).

Scheme C-5

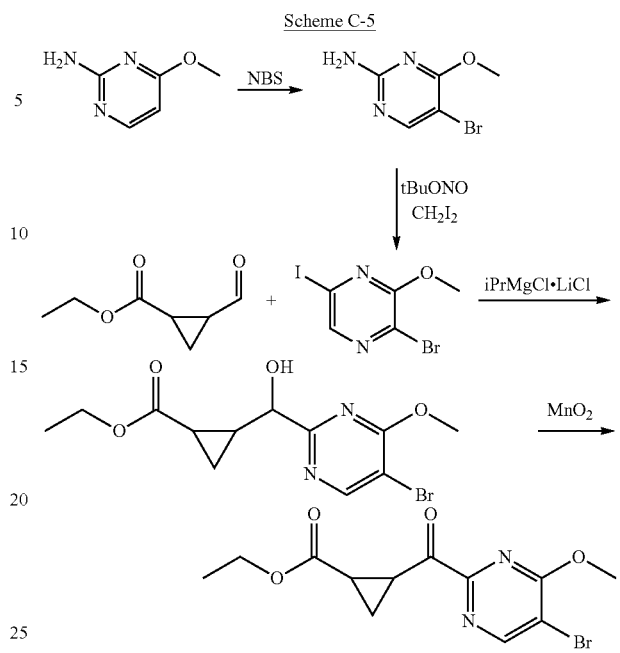

Int 3:5 Ethyl 2-(5-bromo-4-methoxypyrimidine-2-carbonyl)cyclopropanecarboxylate

5-Bromo-4-methoxypyrimidin-2-amine

N-Bromosuccinimide (6.05 g, 34.0 mmol) was added to a solution of 4-methoxypyrimidin-2-amine (3.87 g, 30.9 mmol) in MeCN (50 mL). The mixture was stirred at 80° C. for 2 h, and then the MeCN was partly evaporated. Extractive workup (DCM, water, brine) and concentration of the DCM extracts afforded the sub-title compound. Yield: 5.73 g (91%).

5-Bromo-2-iodo-4-methoxypyrimidine tert-Butylnitrite (5.87 mL, 49.0 mmol) was added to a solution of 5-bromo-4-methoxypyrimidin-2-amine (2.00 g, 9.80 mmol) in MeCN (1 mL) and diiodomethane (5 mL) and the reaction mixture was stirred at 80° C. for 2 h. Extractive workup (EtOAc, water, brine) and concentration of the EtOAc extracts followed by column chromatography afforded the sub-title compound. Yield: 1.02 g (33%).

Ethyl 2-((5-bromo-4-methoxypyrimidin-2-yl)(hydroxy)methyl)cyclopropanecarboxylate A solution of iPrMgCl.LiCl complex in THF (1.3 M, 2.62 mL, 3.40 mmol) was added dropwise to a solution of 5-bromo-2-iodo-4-methoxypyrimidine (1.02 g, 3.24 mmol) in THF (5 mL) −60° C. After stirring at −60−−50° C. for 30 min, the reaction mixture was cooled to −60° C. and ethyl 2-formylcyclopropanecarboxylate (1.80 mL, 13.4 mmol) was added dropwise. The reaction mixture was allowed to reach rt, then quenched with saturated aq NH$_4$Cl. Extractive workup (EtOAc, water, brine) and concentration of the EtOAc extracts followed by column chromatography afforded the sub-title compound. Yield: 0.90 g (84%).

Ethyl 2-(5-bromo-4-methoxypyrimidine-2-carbonyl)cyclopropanecarboxylate

MnO$_2$ (1.35 g, 15.5 mmol) was added to a solution of ethyl 2-((5-bromo-4-methoxypyrimidin-2-yl)(hydroxy)methyl)cyclopropanecarboxylate (0.90 g, 2.72 mmol) in toluene (5 mL). After stirring at 80° C. for 24 h, the reaction mixture was filtered through a silicagel pad. Concentration of the filtrate followed by column chromatography afforded the sub-title compound. Yield: 0.67 g (75%).

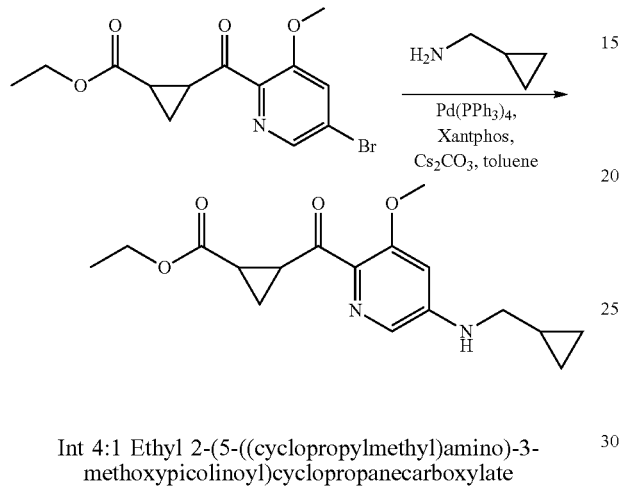

Int 4:1 Ethyl 2-(5-((cyclopropylmethyl)amino)-3-methoxypicolinoyl)cyclopropanecarboxylate To a test tube were added Pd(PPh$_3$)$_4$ (277 mg, 0.24 mmol), Xantphos (208 mg, 0.36 mmol) and toluene (5 mL). The mixture was stirred at rt for 15 min. To a 20 mL microwave vial were added ethyl 2-(5-bromo-3-methoxypicolinoyl)cyclopropanecarboxylate (1.31 g, 4.0 mmol), cyclopropylmethanamine (370 mg, 5.2 mmol), Cs$_2$CO$_3$ (2.61 g, 8.0 mmol) and toluene (10 mL). The mixture was stirred at rt for 5 min before the catalyst slurry from the test tube was transferred to the microwave vial. The vial was sealed with a Teflon fitted septa and heated at 90° C. over night. The reaction mixture was filtered through a short silica column and the filtrate was concentrated in vacuo. The crude solid was dissolved in DCM and purified by silica chromatography (isohexane:EtOAc 1:1) to give 1.04 g (82% yield) of pure product as a pale yellow solid.

Synthesis of Compounds of the Invention

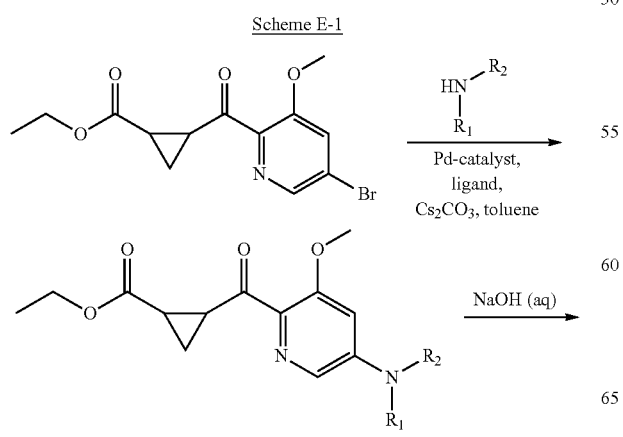

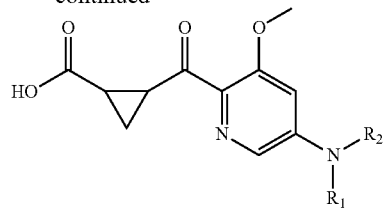

A detailed illustrative synthetic procedure for the general procedure shown in Scheme E-1 is described below.

Example 1

2-(5-((4-Chloronaphthalen-1-yl)(cyclopropylmethyl)amino)-3-methoxypicolinoyl)cyclopropanecarboxylic acid

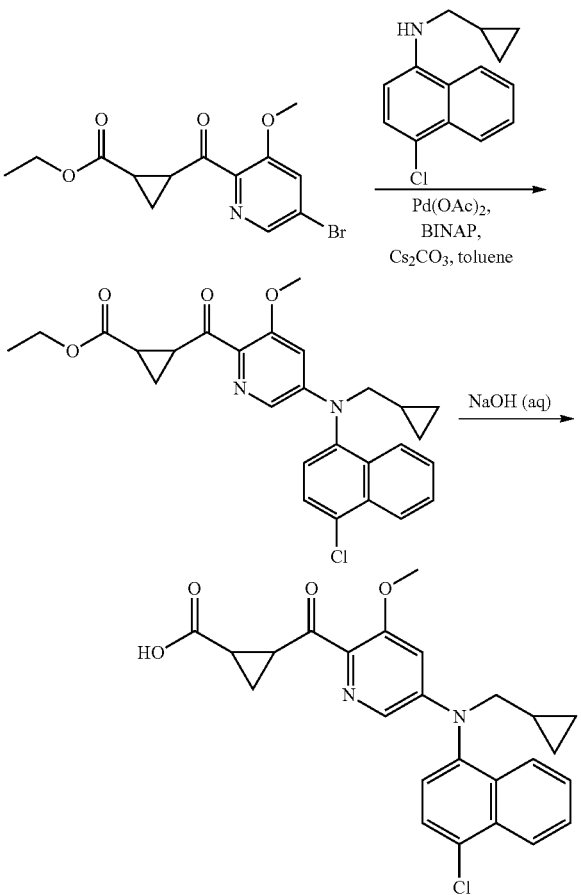

Ethyl 2-(5-((4-chloronaphthalen-1-yl)(cyclopropylmethyl)amino)-3-methoxypicolinoyl)cyclopropanecarboxylate Ethyl 2-(5-bromo-3-methoxypicolinoyl)cyclopropanecarboxylate (118 mg, 0.36 mmol), 4-chloro-N-(cyclopropylmethyl)naphthalen-1-amine (100 mg, 0.43 mmol), Pd(OAc)$_2$ (4.0 mg, 0.018 mmol), rac-BINAP (16 mg, 0.025 mmol) and Cs$_2$CO$_3$ (164 mg, 0.50 mmol) were mixed in toluene (10 mL) and stirred in a sealed tube at 70° C. for 42 h. Extractive workup (EtOAc, water, brine) and concentration of the EtOAc extracts followed by column chromatography afforded the sub-title compound. Yield: 112 mg (81%).

2-(5-((4-Chloronaphthalen-1-yl)(cyclopropylmethyl)amino)-3-methoxypicolinoyl)cyclopropanecarboxylic acid A mixture of ethyl 2-(5-((4-chloronaphthalen-1-yl)(cyclopropylmethyl)amino)-3-methoxypicolinoyl)cyclopropanecarboxylate (75 mg, 0.16 mmol) and NaOH (31 mg, 0.78 mmol) in EtOH (2 mL) and water (1 mL) was stirred at 70° C. for 30 min. Acidification with 1M aq HCl (pH~3), extraction (EtOAc), washing (water and brine), drying ($Na_2SO_4$), filtration and evaporation furnished the title compound. Yield: 66 mg (93%). MS [M+H]$^+$451. $^1$H-NMR 400 MHz (DMSO-d$_6$, ppm) δ 8.36 (1H, d, J=8.5 Hz), 7.76-7.70 (2H, m), 7.69-7.63 (2H, m), 7.57-7.50 (1H, m), 7.42 (1H, d, J=7.8 Hz), 6.31-6.27 (1H, m), 4.04-3.76 (2H, m), 3.64 (3H, s), 3.62-3.30 (1H, m), 2.27-2.19 (1H, m), 1.61-1.55 (1H, m), 1.54-1.47 (1H, m), 1.24-1.14 (1H, m), 0.57-0.44 (2H, m), 0.16-0.03 (2H, m).

The following compounds were prepared in analogy to Example 1 described above in detail unless otherwise indicated.

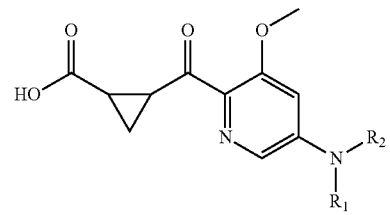

TABLE 3

| Ex. | R$_1$ | R$_2$ | MS [M+H]$^+$ Name $^1$H-NMR | Pd-catalyst and ligand according to Scheme E-1 |
|---|---|---|---|---|
| 2 | 4-chlorophenyl | cyclopropylmethyl | 401 | Pd(PPh$_3$)$_4$, Xantphos |

2-(5-((4-Chlorophenyl)(cyclopropylmethyl)amino)-3-methoxypicolinoyl)cyclopropanecarboxylic acid
400 MHz (DMSO-d$_6$, ppm) δ 12.42 (1H, br s), 7.68 (1H, d, J = 2.3 Hz), 7.55-7.51 (2H, m), 7.39-7.35 (2H, m), 6.76 (1H, d, J = 2.4 Hz), 3.75 (3H, s), 3.72 (2H, d, J = 6.7 Hz), 3.59 (1H, ddd, J = 7.8, 6.7, 3.9 Hz), 1.87 (1H, ddd, J = 7.4, 6.5, 3.9 Hz), 1.32-1.28 (2H, m), 1.15-1.05 (1H, m), 0.47-0.42 (2H, m), 0.17-0.13 (2H, m)

| 3 | 4-chlorophenyl | (1-(trifluoromethyl)cyclopropyl)methyl | 469 | Pd(OAc)$_2$, BINAP |

2-(5-((4-Chlorophenyl)((1-(trifluoromethyl)cyclopropyl)methyl)amino)-3-methoxypicolinoyl)cyclopropanecarboxylic acid
400 MHz (DMSO-d$_6$, ppm) δ 12.52 (1H, br s), 7.63 (1H, d, J = 2.3 Hz), 7.58-7.54 (2H, m), 7.41-7.36 (2H, m), 6.78 (1H, d, J = 2.3 Hz), 4.26 (2H, app s), 3.74 (3H, s), 3.58-3.53 (1H, m), 1.90-1.85 (1H, m), 1.33-1.28 (2H, m), 0.95-0.91 (2H, m), 0.60-0.55 (2H, m)

| 4 | 4-chlorophenyl | (1-(methoxymethyl)cyclopropyl)methyl | 445 | Pd(OAc)$_2$, BINAP |

2-(5-((4-Chlorophenyl)((1-(methoxymethyl)cyclopropyl)methyl)amino)-3-methoxypicolinoyl)cyclopropanecarboxylic acid
400 MHz (DMSO-d$_6$, ppm) δ 7.59 (1H, d, J = 2.3 Hz), 7.54-7.50 (2H, m), 7.42-7.37 (2H, m), 6.98 (1H, d, J = 2.3 Hz), 3.90 (1H, d, J = 15.7 Hz), 3.85 (1H, d, J = 15.5 Hz), 3.77 (3H, s), 3.57 (1H, ddd, J = 8.0, 6.7, 3.9 Hz), 3.24 (3H, s), 3.21 (1H, d, J = 10.2 Hz), 3.18 (1H, d, J = 10.3 Hz), 1.89-1.84 (1H, m), 1.31-1.27 (2H, m), 0.37-0.34 (2H, m), 0.19-0.16 (2H, m)

TABLE 3-continued

| Ex. | R₁ | R₂ | MS [M+H]⁺ Name ¹H-NMR | Pd-catalyst and ligand according to Scheme E-1 |
|---|---|---|---|---|
| 5 | 4-chlorophenyl | (1-methylcyclopropyl)methyl | 415 | Pd(OAc)₂, BINAP |

2-(5-((4-Chlorophenyl)((1-methylcyclopropyl)methyl)amino)-3-methoxypicolinoyl)cyclopropanecarboxylic acid
400 MHz (DMSO-d₆, ppm) δ 12.47 (1H, br s), 7.69 (1H, d, J = 2.3 Hz), 7.5-7.51 (2H, m), 7.42-7.37 (2H, m), 6.78 (1H, d, J = 2.3 Hz), 3.83 (2H, app s), 3.74 (3H, s), 3.59 (1H, ddd, J = 7.9, 6.7, 3.9 Hz), 1.89-1.84 (1H, m), 1.33-1.27 (2H, m), 1.11 (3H, s), 0.23-0.14 (4H, m)

| 6 | 2,3-dihydro-1H-inden-5-yl | (1-methylcyclopropyl)methyl | 421 | Pd(OAc)₂, BINAP |

2-(5-((2,3-Dihydro-1H-inden-5-yl)((1-methylcyclopropyl)methyl)amino)-3-methoxypicolinoyl)cyclopropanecarboxylic acid
400 MHz (CDCl₃, ppm) δ 7.76 (1H, d, J = 2.3 Hz), 7.26 (1H, d, J = 8.0 Hz), 7.05 (1H, d, J = 2.2 Hz), 6.96 (1H, dd, J = 7.9, 2.0 Hz), 6.48 (1H, J = 2.4 Hz), 3.85 (1H, ddd, J = 8.8, 6.1, 3.9 Hz), 3.76 (3H, s), 3.71 (2H, app s), 2.96-2.90 (4H, m), 2.25 (1H, ddd, J = 8.5, 5.7, 3.9 Hz), 2.17-2.09 (2H, m), 1.59 (2H, ddd, J = 8.5, 6.0, 3.2 Hz), 1.51 (1H, ddd, J = 8.8, 5.7, 3.2 Hz), 1.17 (3H, s), 0.32-0.23 (4H, m)

| 7 | 4-fluoronaphthalen-1-yl | cyclopropylmethyl | 435 | Pd(OAc)₂, BINAP |

2-(5-((Cyclopropylmethyl)(4-fluoronaphthalen-1-yl)amino)-3-methoxypicolinoyl)cyclopropanecarboxylic acid
400 MHz (DMSO-d₆, ppm) δ 8.19 (1H, d, J = 8.4 Hz), 7.73-7.67 (2H, m), 7.60 (1H, t, J = 7.6 Hz), 7.56-7.50 (1H, m), 7.42 (1H, dd, J = 8.2 4.9 Hz), 7.25-7.19 (1H, m), 6.27 (1H, m), 3.98-3.78 (2H, m), 3.65 (3H, s), 3.58-3.39 (1H, m), 2.27-2.19 (1H, m), 1.61-1.55 (1H, m), 1.54-1.47 (1H, m), 1.24-1.14 (1H, m), 0.58-0.42 (2H, m), 0.16-0.03 (2H, m)

| 8 | 8-methylquinolin-5-yl | cyclopropylmethyl | 432 | Pd(OAc)₂, Xantphos |

2-(5-((Cyclopropylmethyl)(8-methylquinolin-5-yl)amino)-3-methoxypicolinoyl)cyclopropanecarboxylic acid
400 MHz (CDCl₃, ppm) δ 9.00 (1H, dd, J = 4.2, 1.5 Hz), 8.06 (1H, dd, J = 8.6, 1.5 Hz), 7.74-7.68 (1H, m), 7.68-7.63 (1H, m), 7.45 (1H, d, J = 7.5 Hz), 7.40 (1H, dd, J = 8.6, 4.2 Hz), 6.31-6.20 (1H, m), 3.86-3.54 (6H, m), 2.87 (3H, s), 2.28-2.20 (1H, m), 1.62-1.55 (1H, m), 1.55-1.47 (1H, m), 1.23-1.12 (1H, m), 0.57-0.42 (2H, m), 0.16-0.01 (2H, m)

TABLE 3-continued

| Ex. | R₁ | R₂ | MS [M+H]⁺ Name ¹H-NMR | Pd-catalyst and ligand according to Scheme E-1 |
|---|---|---|---|---|
| 9 | naphthalen-1-yl | cyclopropylmethyl | 417 | Pd(OAc)₂, BINAP |

2-(5-((Cyclopropylmethyl)(naphthalen-1-yl)amino)-3-methoxypicolinoyl)cyclopropanecarboxylic acid
400 MHz (CDCl₃, ppm) δ 7.95 (1H, d, J = 8.2 Hz), 7.92 (1H, d, J = 8.2 Hz), 7.78-7.71 (2H, m) 7.59-7.46 (4H, m) 6.29 (1H, s) 4.06-3.87 (1H, m) 3.86-3.81 (1H, m) 3.64 (3H, s) 3.60-3.38 (1H, m) 2.27-2.22 (1H, m) 1.62-1.57 (1H, m) 1.54-1.49 (1H, m) 1.28-1.18 (1H, m) 0.56-0.44 (2H, m) 0.16-0.04 (2H, m)

| 10 | 4-methylquinolin-8-yl | cyclopropylmethyl | 431 | Pd(OAc)₂, Xantphos |

2-(5-((Cyclopropylmethyl)(4-methylquinolin-8-yl)amino)-3-methoxypicolinoyl)cyclopropanecarboxylic acid
400 MHz (CDCl₃, ppm) δ 8.79-9.10 (1H, d, J = 4.4 Hz), 8.07 (1H, dd, J = 8.4, 1.4 Hz), 7.74 (1H, dd, J = 7.4, 1.4 Hz) 7.66-7.60 (2H, m), 7.31-7.28 (1H, m), 6.43 (1H, d, J = 2.1 Hz), 3.81-3.75 (3H, m), 3.71 (3H, s), 2.77 (3H, s), 2.23-2.16 (1H, m), 1.55-1.49 (1H, m), 1.46-1.40 (1H, m), 1.20-1.09 (1H, m), 0.49-0.36 (2H, m), 0.08-0.00 (2H, m)

Scheme E-2

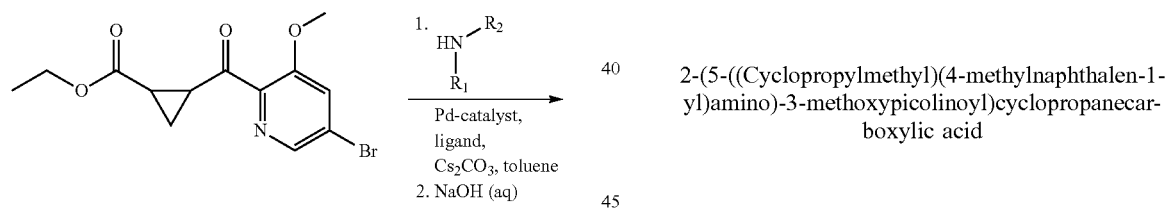

A detailed illustrative synthetic procedure for the general procedure shown in Scheme E-2 is described below.

Example 11

2-(5-((Cyclopropylmethyl)(4-methylnaphthalen-1-yl)amino)-3-methoxypicolinoyl)cyclopropanecarboxylic acid

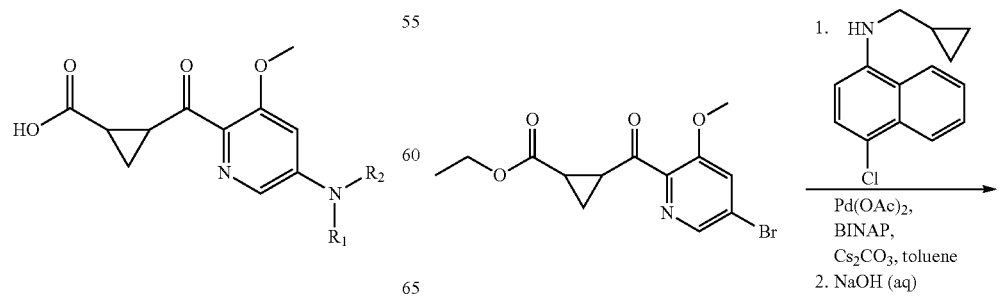

-continued

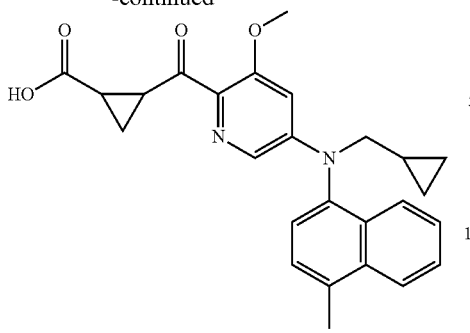

To a 20 mL vial were added Pd(OAc)$_2$ (225 mg, 1.0 mmol), rac-BINAP (747 mg, 1.2 mmol) and toluene (15 mL). The mixture was sealed and stirred at 80° C. for 15 min. To a 250 mL round-bottom flask were added ethyl 2-(5-bromo-3-methoxypicolinoyl)cyclopropanecarboxylate (3.28 g, 10.0 mmol), N-(cyclopropylmethyl)-4-methylnaphthalen-1-amine (2.33 g, 11.0 mmol) and toluene (150 mL). The reaction mixture was stirred at rt for 15 min and Cs$_2$CO$_3$ (6.52 g, 20.0 mmol) was added. To the round-bottom flask was added the catalyst mixture and the round-bottom flask was sealed with a rubber septum and heated at 100° C. for 48 h. The reaction mixture was filtered through a short silica column and the filtrate was concentrated in vacuo. The crude solid was dissolved in DCM and purified by silica chromatography (isohexane:EtOAc 95:5). The purified ester product was dissolved in THF/water and the pH was adjusted to 13 with addition of 2 M aq NaOH, and the reaction mixture was stirred at rt. Complete ester hydrolysis was obtained in 72 h. The reaction mixture was acidified with HOAc to pH 3 and EtOAc was added followed by extractive workup. The organic phases were collected and concentrated in vacuo to give a yellow residue. The crude product was purified by silica chromatography (isohexane:EtOAc 1:1, 1% HOAc) and washing (water/MeOH/MeCN 10:4:1, followed by 3× water) to provide 1.04 g (24% yield) of the pure product as a pale yellow solid. MS [M+H]$^+$ 431. $^1$H-NMR 400 MHz (DMSO-d$_6$, ppm) δ 12.38 (1H, br s), 8.13 (1H, d, J=8.4 Hz), 7.72 (1H, d, J=8.2 Hz), 7.62 (1H, ddd, J=8.3, 6.8, 1.4 Hz), 7.55-7.47 (3H, m), 7.30-7.25 (1H, m), 6.66-6.60 (1H, m), 4.03-3.90 (1H, m), 3.70 (3H, s), 3.62-3.52 (2H, m), 2.72 (3H, s), 1.84 (1H, ddd, J=8.2, 5.9, 3.9 Hz), 1.29-1.23 (2H, m), 1.18-1.08 (1H, m), 0.42-0.35 (2H, m), 0.14-0.07 (2H, m).

Scheme F

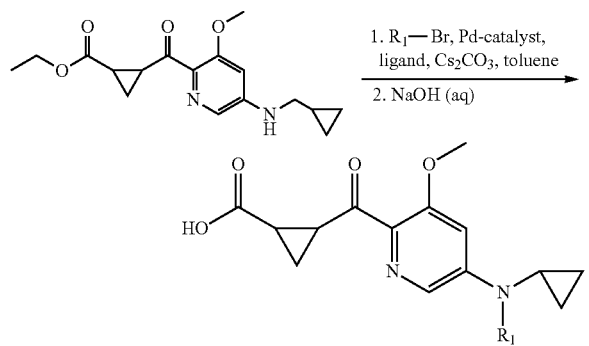

A detailed illustrative synthetic procedure for the general procedure shown in Scheme F is described below.

Example 12

2-(5-(((Cyclopropylmethyl)(naphthalen-2-yl)amino)-3-methoxypicolinoyl)cyclopropanecarboxylic acid

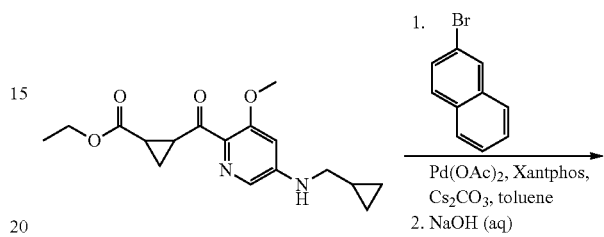

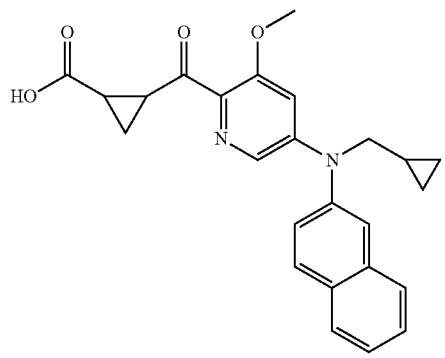

To a test tube were added Pd(OAc)$_2$ (5.6 mg, 0.025 mmol), Xantphos (21.7 mg, 0.038 mmol) and toluene (1 mL). The mixture was stirred at rt for 15 min. To a 5 mL microwave vial were added ethyl 2-(5-((cyclopropylmethyl)amino)-3-methoxypicolinoyl)cyclopropanecarboxylate (80 mg, 0.25 mmol), 2-bromonaphthalene (104 mg, 0.50 mmol), Cs$_2$CO$_3$ (163 mg, 0.50 mmol) and toluene (1 mL). The mixture was stirred at rt for 5 min before the catalyst slurry from the test tube was transferred to the microwave vial. The vial was sealed with a Teflon fitted septa and heated at 100° C. for 48 h. The reaction mixture was filtered through a short silica column and the filtrate was concentrated in vacuo. The crude solid was dissolved in DCM and purified by silica chromatography (isohexane:EtOAc 1:1) to give 49 mg of a pale yellow solid. The solid was dissolved in THF:MeOH and 2 M aq NaOH was added to reach pH 14. After stirring at rt for 2 h complete ester hydrolysis was achieved and the reaction mixture was acidified with 2 M aq HCl to pH 1. The solvent was evaporated in vacuo and the crude was dissolved in DMSO:MeOH and purified by HPLC to provide 38 mg (83% yield) of pure product as a pale yellow solid. MS [M+H]$^+$ 417. $^1$H NMR 400 MHz (DMSO-d$_6$, ppm) δ 12.47 (1H, br s), 8.02 (1H, d, J=8.7 Hz), 7.97-7.92 (2H, m), 7.90 (1H, d, J=2.2 Hz), 7.74 (1H, d, J=2.3 Hz), 7.57-7.50 (2H, m), 7.47 (1H, dd, J=8.8, 2.2 Hz), 6.82 (1H, d, J=2.3 Hz), 3.85 (2H, app d, J=6.7 Hz), 3.73 (3H, s), 3.62-3.57 (1H, m), 1.88 (1H, ddd, J=7.7, 6.6, 3.9 Hz), 1.32-1.28 (2H, m), 1.23-1.13 (1H, m), 0.48-0.43 (2H, m), 0.19-0.15 (2H, m).

Scheme G

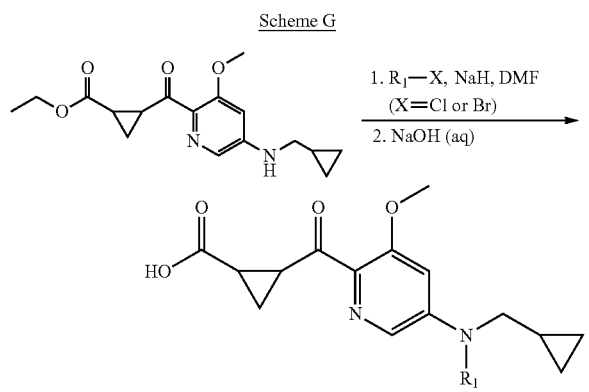

A detailed illustrative synthetic procedure for the general procedure shown in Scheme G is described below.

Example 13

2-(5-((4-Chlorobenzyl)(cyclopropylmethyl)amino)-3-methoxypicolinoyl)cyclopropanecarboxylic acid

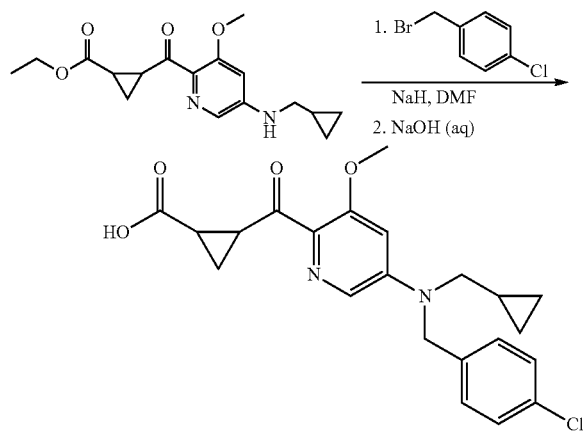

To a 5 mL microwave vial were added ethyl 2-(5-((cyclopropylmethyl)amino)-3-methoxypicolinoyl)cyclopropanecarboxylate (159 mg, 0.50 mmol), NaH (60% in mineral oil, 40 mg, 1.00 mmol) and DMF (2 mL). The vial was sealed with a Teflon fitted septa and heated at 60° C. After 5 min heating, 4-cholorobenzylbromide (411 mg, 2.00 mmol) dissolved in DMF (1 mL) was added with a syringe. The reaction mixture was stirred and heated at 60° C. over night. The reaction mixture was reduced in vacuo and the crude was dissolved in THF:MeOH. To the reaction mixture was added 2 M aq NaOH to reach pH 14. After stirring for 2 h at rt complete ester hydrolysis was achieved and the reaction mixture was acidified to pH 1 with 2 M aq HCl. The solvent was evaporated in vacuo and the crude mixture was dissolved in DMSO:MeOH and purified by HPLC to give 87 mg (42% yield) of product as a pale yellow solid. MS [M+H]$^+$ 415. $^1$H NMR 400 MHz (DMSO-d$_6$, ppm) δ 12.41 (1H, br s), 7.84 (1H, d, J=2.4 Hz), 7.41-7.37 (2H, m), 7.31-7.27 (2H, m), 6.62 (1H, d, J=2.4 Hz), 4.82 (2H, app s), 3.72 (3H, s), 3.62 (1H, ddd, J=8.0, 6.8, 3.9 Hz), 3.52 (2H, app d, J=6.7 Hz), 1.87-1.82 (1H, m), 1.29-1.25 (2H, m), 1.22-1.11 (1H, m), 0.52-0.47 (2H, m), 0.34-0.30 (2H, m).

The following compounds were prepared in analogy to Example 13 described above in detail unless otherwise indicated.

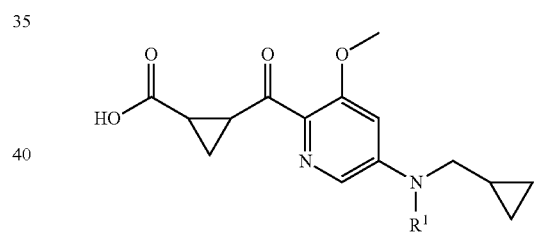

TABLE 4

| Ex. | R$_1$ Name $^1$H-NMR | MS [M + H]$^+$ | X in R$_1$-X according to Scheme G |
|---|---|---|---|
| 14 | <br>2-(5-((Cyclopropylmethyl)(4-methylbenzyl)amino)-3-methoxypicolinoyl)cyclopropanecarboxylic acid<br>400 MHz (DMSO-d$_6$, ppm) δ 12.40 (1H, br s), 7.83 (1H, d, J = 2.4 Hz), 7.17-7.12 (4H, m), 6.62 (1H, d, J = 2.4 Hz), 4.77 (2H, app s), 3.72-3.71 (3H, m), 3.62 (1H, ddd, J = 8.1, 6.7, 3.9 Hz), 3.52 (2H, app d, J = 6.6 Hz), 2.26 (3H, s), 1.86-1.81 (1H, m), 1.29-1.25 (2H, m), 1.22-1.12 (1H, m), 0.52-0.48 (2H, m), 0.34-0.30 (2H, m) | 396 | Br |

TABLE 4-continued

| Ex. | R₁ | MS [M + H]⁺ Name ¹H-NMR | X in R₁-X according to Scheme G |
|---|---|---|---|
| 15 | 3-methylbenzyl | 396 | Br |

2-(5-((Cyclopropylmethyl)(3-methylbenzyl)amino)-3-methoxypicolinoyl)cyclopropanecarboxylic acid
400 MHz (DMSO-d₆, ppm) δ 12.37 (1H, br s), 7.84 (1H, d, J = 2.4 Hz), 7.23-7.19 (1H, m), 7.11-7.08 (1H, m), 7.08-7.03 (2H, m), 6.63 (1H, d, J = 2.4 Hz), 4.77 (2H, app s), 3.72 (3H, s), 3.63 (1H, ddd, J = 8.0, 6.7, 3.9 Hz), 3.53 (2H, app d, J = 6.6 Hz), 2.27 (3H, s), 1.87-1.82 (1H, m), 1.29-1.25 (2H, m), 1.22-1.13 (2H, m), 0.53-0.48 (2H, m), 0.35-0.31 (2H, m)

| 16 | 2,6-dichlorobenzyl | 450 | Br |

2-(5-((Cyclopropylmethyl)(2,6-dichlorobenzyl)amino)-3-methoxypicolinoyl)cyclopropanecarboxylic acid
400 MHz (DMSO-d₆, ppm) δ 12.42 (1H, br s), 8.07 (1H, d, J = 2.1 Hz), 7.56-7.54 (2H, m), 7.44-7.39 (1H, m), 6.79 (1H, d, J = 2.2 Hz), 4.96 (2H, app s), 3.79 (3H, s), 3.69-3.64 (1H, m), 3.29 (2H, app d, J = 6.3 Hz), 1.90-1.85 (1H, m), 1.32-1.28 (2H, m), 1.07-0.97 (1H, m), 0.42-0.37 (2H, m), 0.13-0.08 (2H, m)

| 17 | naphthalen-2-ylmethyl | 431 | Br |

2-(5-((Cyclopropylmethyl)(naphthalen-2-ylmethyl)amino)-3-methoxypicolinoyl)cyclopropanecarboxylic acid
400 MHz (DMSO-d₆, ppm) δ 12.42 (1H, br s), 7.96-7.82 (4H, m), 7.77 (1H, s), 7.51-7.42 (3H, m), 6.71 (1H, s), 4.99 (2H, app s), 3.71 (3H, s), 3.65-3.57 (3H, m), 1.86-1.81 (1H, m), 1.30-1.14 (3H, m), 0.56-0.48 (2H, m), 0.39-0.32 (2H, m)

| 18 | 3-chlorobenzyl | 415 | Br |

2-(5-((3-Chlorobenzyl)(cyclopropylmethyl)amino)-3-methoxypicolinoyl)cyclopropanecarboxylic acid
400 MHz (DMSO-d₆, ppm) δ 12.39 (1H, br s), 7.84 (1H, app s), 7.40-7.30 (3H, m), 7.23 (1H, d, J = 7.6 Hz), 6.63 (1H, app s), 4.84 (2H, app s), 3.72 (3H, s), 3.65-3.58 (1H, m), 3.54 (2H, app d, J = 6.7 Hz), 1.87-1.82 (1H, m), 1.30-1.25 (2H, m), 1.23-1.13 (1H, m), 0.52-0.48 (2H, m), 0.36-0.31 (2H, m)

| 19 | 4-fluorobenzyl | 399 | Br |

2-(5-((Cyclopropylmethyl)(4-fluorobenzyl)amino)-3-methoxypicolinoyl)cyclopropanecarboxylic acid
400 MHz (DMSO-d₆, ppm) δ 12.43 (1H, br s), 7.85 (1H, d, J = 2.3 Hz), 7.33-7.28 (2H, m), 7.19-7.13 (2H, m), 6.62 (1H, d, J = 2.4 Hz), 4.80 (2H, app s), 3.72 (3H, TABLE 4-continued

| Ex. | R₁ / Name / ¹H-NMR | MS [M + H]⁺ | X in R₁-X according to Scheme G |
|---|---|---|---|
| | s), 3.65-3.58 (1H, m), 3.52 (2H, app d, J = 6.6 Hz), 1.87-1.82 (1H, m), 1.30-1.21 (2H, m), 1.21-1.12 (1H, m), 0.52-0.47 (2H, m), 0.34-0.30 (2H, m) | | |
| 20 | 2-methyl-3-(trifluoromethyl)benzyl group | 463 | Br |
| | 2-(5-((Cyclopropylmethyl)(2-methyl-3-(trifluoromethyl)benzyl)amino)-3-methoxypicolinoyl)cyclopropanecarboxylic acid | | |
| | 400 MHz (DMSO-d₆, ppm) δ 12.43 (1H, br s), 7.75 (1H, d, J = 2.3 Hz), 7.59 (1H, d, J = 7.9 Hz), 7.34-7.29 (1H, dd, J = 7.9, 7.9 Hz), 7.21 (1H, d, J = 7.9 Hz), 6.63 (1H, d, J = 2.3 Hz), 4.86 (2H, app s), 3.74 (3H, s), 3.63-3.58 (1H, m), 3.51 (2H, app d, J = 6.7 Hz), 2.43 (3H, s), 1.86-1.81 (1H, m), 1.29-1.14 (3H, m), 0.50-0.45 (2H, m), 0.33-0.29 (2H, m) | | |
| 21 | 2-fluoro-4-(trifluoromethyl)benzyl group | 468 | Br |
| | 2-(5-((Cyclopropylmethyl)(2-fluoro-4-(trifluoromethyl)benzyl)amino)-3-methoxypicolinoyl)cyclopropanecarboxylic acid | | |
| | 400 MHz (DMSO-d₆, ppm) δ 12.42 (1H, br s), 7.85 (1H, d, J = 2.3 Hz), 7.72 (1H, d, J = 10.1 Hz), 7.53 (1H, d, J = 8.1 Hz), 7.39-7.35 (1H, m), 6.69 (1H, d, J = 2.3 Hz), 4.96 (2H, app s), 3.75 (3H, s), 3.65-3.60 (1H, m), 3.53 (2H, app d, J = 6.7 Hz), 1.88-1.83 (1H, m), 1.30-1.27 (2H, m), 1.21-1.11 (1H, m), 0.50-0.45 (2H, m), 0.32-0.28 (2H, m) | | |
| 22 | 2-chloro-3-(trifluoromethyl)benzyl group | 485 | Br |
| | 2-(5-((2-Chloro-3-(trifluoromethyl)benzyl)(cyclopropylmethyl)amino)-3-methoxypicolinoyl)cyclopropanecarboxylic acid | | |
| | 400 MHz (DMSO-d₆, ppm) δ 12.41 (1H, br s), 7.79 (1H, dd, J = 7.9, 1.6 Hz), 7.77 (1H, d, J = 2.4 Hz), 7.50 (1H, t, J = 7.8 Hz), 7.40 (1H, dd, J = 7.7, 1.5 Hz), 6.65 (1H, d, J = 2.4 Hz), 4.95 (2H, app s), 3.74 (3H, s), 3.64-3.59 (1H, m), 3.55 (2H, app d, J = 6.7 Hz), 1.88-1.83 (1H, m), 1.31-1.26 (2H, m), 1.23-1.12 (1H, m), 0.50-0.45 (2H, m), 0.32-0.27 (2H, m) | | |
| 23 | (2-methylnaphthalen-1-yl)methyl group | 445 | Cl |
| | 2-(5-((Cyclopropylmethyl)((2-methylnaphthalen-1-yl)methyl)amino)-3-methoxypicolinoyl)cyclopropanecarboxylic acid | | |
| | 400 MHz (DMSO-d₆, ppm) δ 12.43 (1H, br s), 8.17 (1H, d, J = 2.3 Hz), 8.00 (1H, d, J = 8.5 Hz), 7.92 (1H, dd, J = 7.9, 1.6 Hz), 7.86 (1H, d, J = 8.4 Hz), 7.54-7.42 (3H, m), 6.90 (1H, d, J = 2.4 Hz), 5.13 (2H, app s), 3.75 (3H, s), 3.70 (1H, ddd, | | |

TABLE 4-continued

| Ex. | R₁ | MS [M + H]⁺ Name ¹H-NMR | X in R₁-X according to Scheme G |
|---|---|---|---|

J = 8.0, 6.7, 3.9 Hz), 3.12 (2H, app d, J = 6.1 Hz), 2.51 (3H, s), 1.91-1.86 (1H, m), 1.34-1.29 (2H, m), 0.92-0.82 (1H, m), 0.27-0.22 (2H, m), −0.13−−0.19 (2H, m)

| 24 | [biphenyl-4-ylmethyl structure] | 458 | Cl |

2-(5-(([1,1'-Biphenyl]-4-ylmethyl)(cyclopropylmethyl)amino)-3-methoxypicolinoyl)cyclopropanecarboxylic acid
400 MHz (DMSO-d₆, ppm) δ 12.36 (1H, br s), 7.87 (1H, d, J = 2.3 Hz), 7.67-7.61 (4H, m), 7.47-7.42 (2H, m), 7.38-7.32 (3H, m), 6.69 (1H, d, J = 2.4 Hz), 4.88 (2H, app s), 3.74 (3H, s), 3.63 (1H, ddd, J = 7.7, 6.7, 3.9 Hz), 3.57 (2H, app d, J = 6.6 Hz), 1.85 (1H, ddd, J = 7.5, 6.4, 3.9 Hz), 1.31-1.25 (2H, m), 1.26-1.15 (1H, m), 0.55-0.50 (2H, m), 0.38-0.34 (2H, m)

| 25 | [naphthalen-1-ylmethyl structure] | 432 | Cl |

2-(5-((Cyclopropylmethyl)(naphthalen-1-ylmethyl)amino)-3-methoxypicolinoyl)cyclopropanecarboxylic acid
400 MHz (DMSO-d₆, ppm) δ 12.38 (1H, br s), 8.11 (1H, dd, J = 8.0, 1.3 Hz), 7.98 (1H, dd, J = 7.4, 2.1 Hz), 7.85 (1H, d, J = 8.2 Hz), 7.81 (1H, d, J = 2.4 Hz), 7.64-7.56 (2H, m), 7.43 (1H, dd, J = 8.2, 7.1 Hz), 7.19 (1H, dd, J = 7.2, 1.2 Hz), 6.68 (1H, d, J = 2.4 Hz), 5.30 (2H, app s), 3.68 (3H, s), 3.64-3.59 (1H, m), 3.57 (2H, app d, J = 6.6 Hz), 1.84 (1H, ddd, J = 8.0, 6.4, 3.9 Hz), 1.30-1.18 (3H, m), 0.51-0.46 (2H, m), 0.34-0.30 (2H, m)

| 26 | [6-fluoro-4H-benzo[d][1,3]dioxin-8-ylmethyl structure] | 458 | Cl |

2-(5-((Cyclopropylmethyl)((6-fluoro-4H-benzo[d][1,3]dioxin-8-yl)methyl)amino)-3-methoxypicolinoyl)cyclopropanecarboxylic acid
400 MHz (DMSO-d₆, ppm) δ 12.41 (1H, br s), 7.76 (1H, d, J = 2.4 Hz), 6.89 (1H, dd, J = 8.6, 3.1 Hz), 6.72 (1H, dd, J = 9.5, 3.1 Hz), 6.63 (1H, d, J = 2.4 Hz), 5.34 (2H, app s), 4.91 (2H, app s), 4.71 (2H, app s), 3.75 (3H, s), 3.65-3.60 (1H, m), 3.53 (2H, d, J = 6.7 Hz), 1.88-1.83 (1H, m), 1.30-1.25 (2H, m), 1.21-1.13 (1H, m), 0.52-0.47 (2H, m), 0.34-0.29 (2H, m)

| 27 | [6-chlorobenzo[d][1,3]dioxol-4-ylmethyl structure] | 460 | Cl |

2-(5-(((6-Chlorobenzo[d][1,3]dioxol-4-yl)methyl)(cyclopropylmethyl)amino)-3-methoxypicolinoyl)cyclopropanecarboxylic acid
400 MHz (DMSO-d₆, ppm) δ 12.40 (1H, s), 7.75 (1H, d, J = 2.4 Hz), 7.14 (1H, s), 6.68 (1H, s), 6.59 (1H, d, J = 2.4 Hz), 6.04-6.03 (2H, m), 4.73 (2H, app s), 3.75 (3H, s), 3.65-3.60 (1H, m), 3.53 (2H, app d, J = 6.7 Hz), 1.89-1.83 (1H, m), 1.30-1.26 (2H, m), 1.22-1.12 (1H, m), 0.52-0.48 (2H, m), 0.34-0.29 (2H, m)

TABLE 4-continued

| Ex. | R₁ | MS [M + H]⁺ Name ¹H-NMR | X in R₁-X according to Scheme G |
|---|---|---|---|
| 28 | (2,3-dimethylbenzyl) | 409 | Br |

2-(5-((Cyclopropylmethyl)(2,3-dimethylbenzyl)amino)-3-methoxypicolinoyl)cyclopropanecarboxylic acid
400 MHz (DMSO-d₆, ppm) δ 12.38 (1H, br s), 7.73 (1H, d, J = 2.4 Hz), 7.06 (1H, d, J = 7.4 Hz), 6.99 (1H, dd, J = 7.6, 7.4 Hz), 6.79 (1H, d, J = 7.6 Hz), 6.62 (1H, d, J = 2.4 Hz), 4.76 (2H, app s), 3.73 (3H, s), 3.65-3.60 (1H, m), 3.47 (2H, app d, J = 6.6 Hz), 2.28 (3H, s), 2.20 (3H, s), 1.86-1.81 (1H, m), 1.30-1.24 (2H, m), 1.22-1.12 (1H, m), 0.51-0.46 (2H, m), 0.32-0.28 (2H, m)

| 29 | (2,3,4-trifluorobenzyl) | 435 | Br |

2-(5-((Cyclopropylmethyl)(2,3,4-trifluorobenzyl)amino)-3-methoxypicolinoyl)cyclopropanecarboxylic acid
400 MHz (DMSO-d₆, ppm) δ 12.40 (1H, br s), 7.87 (1H, d, J = 2.4 Hz), 7.30-7.21 (1H, m), 7.05-6.98 (1H, m), 6.69 (1H, d, J = 2.4 Hz), 4.89 (2H, app s), 3.76 (3H, s), 3.66-3.60 (1H, m), 3.50 (2H, app d, J = 6.7 Hz), 1.88-1.83 (1H, m), 1.31-1.27 (2H, m), 1.20-1.09 (1H, m), 0.50-0.45 (2H, m), 0.32-0.28 (2H, m)

| 30 | (3-chloro-2,4-difluorobenzyl) | 451 | Br |

2-(5-((3-Chloro-2,4-difluorobenzyl)(cyclopropylmethyl)amino)-3-methoxypicolinoyl)cyclopropanecarboxylic acid
400 MHz (DMSO-d₆, ppm) δ 12.41 (1H, br s), 7.87 (1H, d, J = 2.4 Hz), 7.25 (1H, ddd, J = 8.7, 8.7, 1.5 Hz), 7.21-7.14 (1H, m), 6.69 (1H, d, J = 2.4 Hz), 4.89 (2H, app s), 3.76 (3H, s), 3.63 (1H, ddd, J = 7.6, 6.8, 3.9 Hz), 3.50 (2H, app d, J = 6.7 Hz), 1.85 (1H, ddd, J = 7.6, 6.4, 3.8 Hz), 1.31-1.27 (2H, m), 1.20-1.09 (1H, m), 0.50-0.45 (2H, m), 0.32-0.28 (2H, m)

| 31 | (2-fluoro-3-(trifluoromethyl)benzyl) | 467 | Br |

2-(5-((Cyclopropylmethyl)(2-fluoro-3-(trifluoromethyl)benzyl)amino)-3-methoxypicolinoyl)cyclopropanecarboxylic acid
400 MHz (DMSO-d₆, ppm) δ 12.40 (1H, s), 7.88 (1H, d, J = 2.4 Hz), 7.72-7.67 (1H, m), 7.50-7.45 (1H, m), 7.37-7.32 (1H, m), 6.69 (1H, d, J = 2.4 Hz), 4.96 (2H, app s), 3.75 (3H, s), 3.63 (1H, ddd, J = 7.7, 6.7, 3.9 Hz), 3.53 (2H, app d, J = 6.7 Hz), 1.86 (1H, ddd, J = 7.5, 6.4, 3.8 Hz), 1.31-1.26 (2H, m), 1.21-1.11 (1H, m), 0.49-0.44 (2H, m), 0.32-0.28 (2H, m)

TABLE 4-continued

| Ex. | R₁ | MS [M + H]⁺<br>Name<br>¹H-NMR | X in R₁-X according to Scheme G |
|---|---|---|---|
| 32 | ![structure: 2,6-difluoro-3-methylbenzyl] | 431 | Br |

2-(5-((Cyclopropylmethyl)(2,6-difluoro-3-methylbenzyl)amino)-3-
methoxypicolinoyl)cyclopropanecarboxylic acid
400 MHz (DMSO-d₆, ppm) δ 12.44 (1H, br s), 7.99 (1H, d, J = 2.4 Hz), 7.33-7.26
(1H, m), 7.06-7.00 (1H, m), 6.76 (1H, d, J = 2.4 Hz), 4.83 (2H, app s), 3.78 (3H,
s), 3.64 (1H, ddd, J = 8.4, 6.4, 3.9 Hz), 3.43 (2H, app d, J = 6.6 Hz), 2.21-2.18
(3H, m), 1.86 (1H, ddd, J = 7.9, 6.0, 3.9 Hz), 1.31-1.25 (2H, m), 1.15-1.05 (1H,
m), 0.50-0.45 (2H, m), 0.29-0.25 (2H, m)

| 33 | ![structure: 2,3-difluoro-4-methylbenzyl] | 431 | Br |

2-(5-((Cyclopropylmethyl)(2,3-difluoro-4-methylbenzyl)amino)-3-
methoxypicolinoyl)cyclopropanecarboxylic acid
400 MHz (DMSO-d₆, ppm) δ 12.40 (1H, br s), 7.86 (1H, d, J = 2.4 Hz), 7.05-7.00
(1H, m), 6.91-6.86 (1H, m), 6.68 (1H, d, J = 2.4 Hz), 4.87 (2H, app s), 3.75 (3H,
s), 3.63 (1H, ddd, J = 7.9, 6.8, 3.9 Hz), 3.50 (2H, app d, J = 6.7 Hz), 2.25-2.24
(3H, m), 1.85 (1H, ddd, J = 7.4, 6.4, 3.9 Hz), 1.31-1.26 (2H, m), 1.20-1.10 (1H,
m), 0.51-0.46 (2H, m), 0.33-0.28 (2H, m)

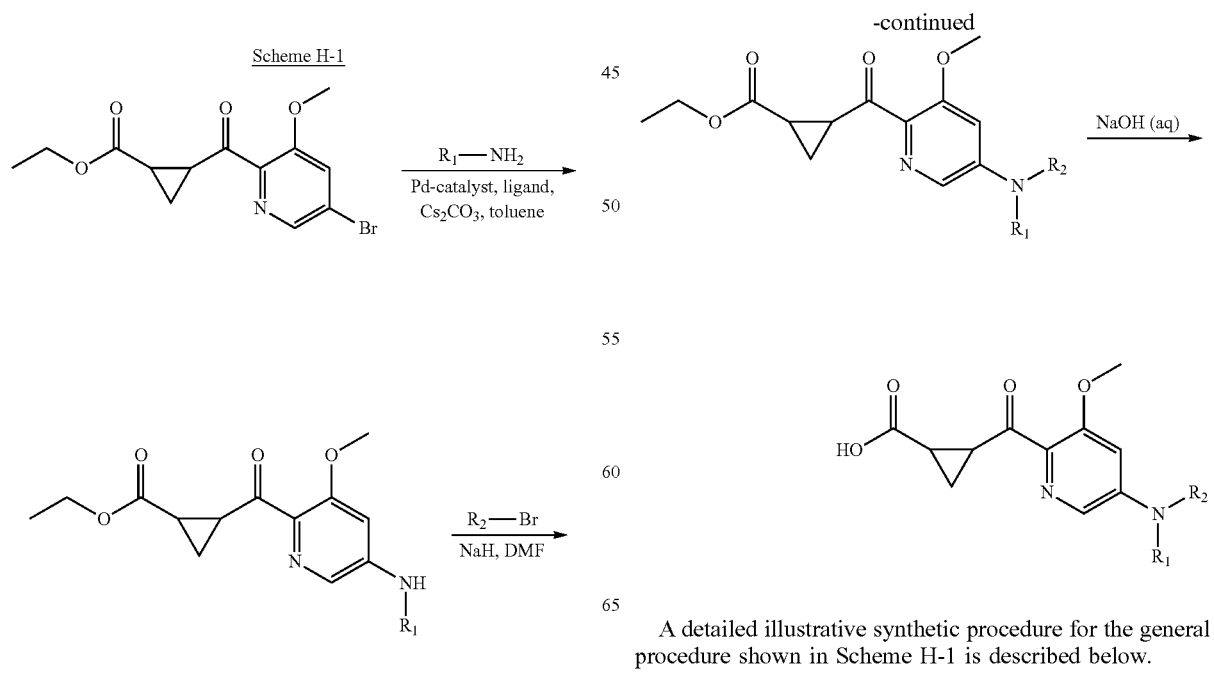

Scheme H-1

A detailed illustrative synthetic procedure for the general procedure shown in Scheme H-1 is described below.

Example 34

2-(5-((Cyclopropylmethyl)(4-(trifluoromethyl)naphthalen-1-yl)amino)-3-methoxypicolinoyl)cyclopropanecarboxylic acid

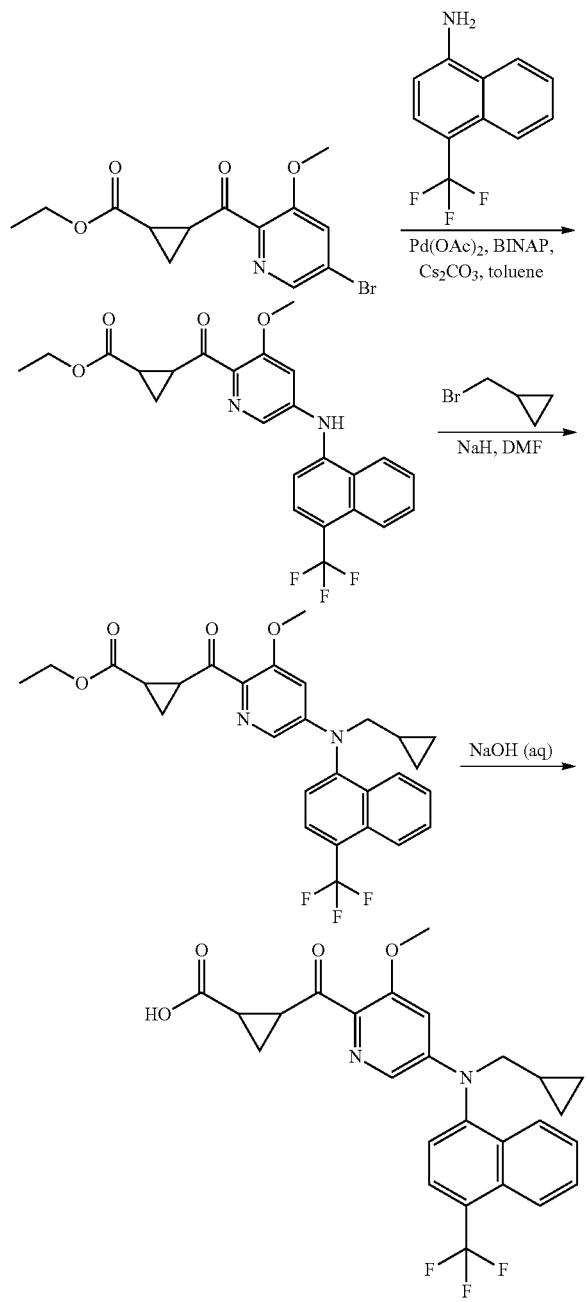

Ethyl 2-(3-methoxy-5-((4-(trifluoromethyl)naphthalen-1-yl)amino)picolinoyl)cyclopropanecarboxylate Ethyl 2-(5-bromo-3-methoxypicolinoyl)cyclopropanecarboxylate (164 mg, 0.50 mmol), 4-(trifluoromethyl)naphthalen-1-amine (127 mg, 0.60 mmol), Pd(OAc)$_2$ (6.0 mg, 0.025 mmol), rac-BINAP (22 mg, 0.035 mmol) and Cs$_2$CO$_3$ (228 mg, 0.70 mmol) were mixed in toluene (4 mL) and stirred at 90-95° C. for 18 h in a sealed tube. The reaction mixture was diluted (EtOAc), filtered through a celite pad, and concentrated. Purification by column chromatography afforded the sub-title compound. Yield: 80 mg (46%).

Ethyl 2-(5-((cyclopropylmethyl)(4-(trifluoromethyl)naphthalen-1-yl)amino)-3-methoxypicolinoyl)cyclopropanecarboxylate NaH (60% dispersion in mineral oil, 7.0 mg, 0.18 mmol) was added in one portion to a stirred solution of ethyl 2-(3-methoxy-5-((4-(trifluoromethyl)naphthalen-1-yl)amino)picolinoyl)cyclopropanecarboxylate (75 mg, 0.16 mmol) in DMF (2 mL) at 0° C. After stirring at 0° C. for 10 min, (bromomethyl)cyclopropane (32 µL, 0.33 mmol) was added. The reaction mixture was stirred at rt for 18 h and then quenched with water. Extractive workup (EtOAc, water and brine) and concentration of the EtOAc extracts followed by column chromatography afforded the sub-title compound contaminated with a small amount of the corresponding cyclopropylmethylester. Yield: 73 mg (84%).

2-(5-((Cyclopropylmethyl)(4-(trifluoromethyl)naphthalen-1-yl)amino)-3-methoxypicolinoyl)cyclopropanecarboxylic acid A solution of NaOH (25 mg, 0.63 mmol) in water (4 mL) was added to a solution of ethyl 2-(5-((cyclopropylmethyl)(4-(trifluoromethyl)naphthalen-1-yl)amino)-3-methoxypicolinoyl)cyclopropanecarboxylate (65 mg, 0.13 mmol) in EtOH (3 mL), and the reaction mixture was stirred at 80° C. for 20 min. Acidification with 1M aq HCl (pH~3), extraction (EtOAc), washing (water and brine), drying (Na$_2$SO$_4$), filtration and evaporation furnished the title compound. Yield: 61 mg (99%). MS [M+H]$^+$ 485. $^1$H NMR 400 MHz (CDCl$_3$, ppm) δ 8.32-8.25 (1H, m), 7.99-7.95 (1H, m), 7.87-7.81 (1H, m), 7.72-7.65 (2H, m), 7.60-7.50 (2H, m), 6.35-6.28 (1H, m), 3.85-3.79 (1H, m), 3.78-3.60 (5H, m), 2.27-2.20 (1H, m), 1.62-1.55 (1H, m), 1.54-1.47 (1H, m), 1.25-1.17 (1H, m), 0.55-0.48 (2H, m), 0.13-0.06 (2H, m).

The following compound was prepared in analogy to Example 34 described above in detail with the exception that Xantphos was used instead of rac-BINAP.

TABLE 5

| Ex. | Structure<br>Name<br>$^1$H-NMR | MS<br>[M + H]$^+$ |
|---|---|---|
| 35 | ![structure] 2-(5-((Cyclopropylmethyl)(5-(trifluoromethyl)quinolin-8-yl)amino)-3-methoxypicolinoyl)cyclopropanecarboxylic acid | 486 |

TABLE 5-continued

| Ex. | Structure<br>Name<br>¹H-NMR | MS<br>[M + H]⁺ |
|---|---|---|
| | 400 MHz (DMSO-d₆, ppm) δ 12.38 (1H, s), 8.97 (1H, dd, J = 4.0 1.6 Hz), 8.61-8.55 (1H, m) 8.21 (1H, d, J = 7.9 Hz), 8.00 (1H, d, J = 7.9 Hz), 7.78 (1H, dd, J = 8.8, 4.0 Hz), 7.33 (1H, d, J = 2.4 Hz), 6.78 (1H, d, J = 2.4 Hz), 3.87 (2H, app d, J = 6.7 Hz), 3.76 (3H, s), 3.57-3.51 (1H, m), 1.88-1.82 (1H, m), 1.31-1.22 (2H, m), 1.12-1.04 (1H, m), 0.37-0.32 (2H, m), 0.08-0.03 (2H, m) | |

Scheme H-2

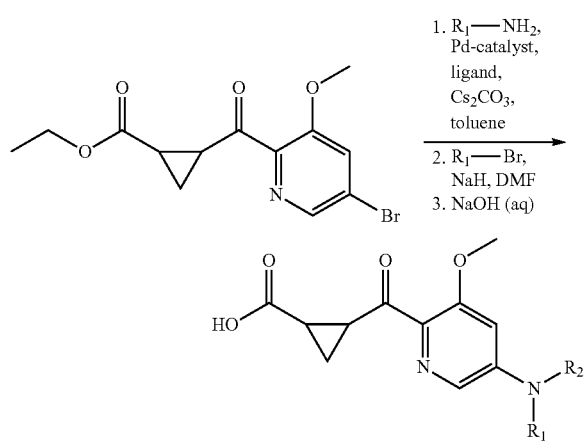

A detailed illustrative synthetic procedure for the general procedure shown in Scheme H-2 is described below.

Example 36

2-(5-((Cyclopropylmethyl)(1,2-dihydroacenaphth-ylen-5-yl)amino)-3-methoxypicolinoyl)cyclopropanecarboxylic acid

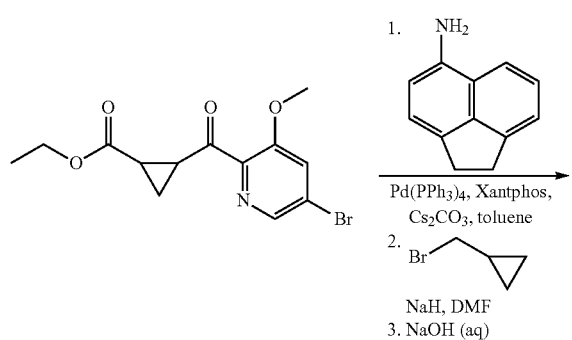

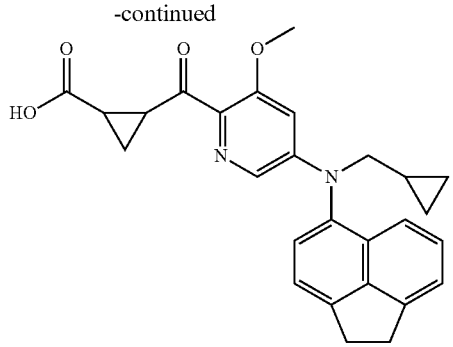

Ethyl 2-(5-bromo-3-methoxypicolinoyl)cyclopropanecarboxylate (164 mg, 0.50 mmol), 1,2-dihydroacenaphthylen-5-amine (127 mg, 0.75 mmol), Pd(PPh₃)₄ (29 mg, 0.025 mmol), Xantphos (22 mg, 0.038 mmol) and Cs₂CO₃ (326 mg, 1.00 mmol) were mixed in toluene (10 mL) and stirred at 110° C. over night in a sealed tube. The reaction mixture was diluted (EtOAc), filtered through a celite pad and concentrated. The crude product was purified by column chromatography and treatment with activate carbon followed by filtration through a short silica column. The purified product (146 mg, 0.35 mmol) was mixed with (bromomethyl)cyclopropane (95 mg, 0.70 mmol) and NaH (60% in mineral oil, 35 mg, 0.88 mmol) in DMF (6 mL) and the reaction mixture was stirred at rt over night. After evaporation of the solvent the crude mixture was dissolved in MeOH:THF and 2M aq NaOH (pH~13) was added. The reaction mixture was stirred at rt until complete hydrolysis. Acidification with 2M aq HCl (pH~2), evaporation and purification by HPLC afforded the title compound. Yield: 95 mg (43%). MS [M+H]⁺ 443. ¹H NMR 400 MHz (DMSO-d₆, ppm) δ 12.40 (1H, br s), 7.52-7.42 (3H, m), 7.39-7.31 (3H, m), 6.64 (1H, s), 3.79 (2H, br s), 3.69 (3H, s), 3.55 (1H, ddd, J=8.3, 6.2, 3.9 Hz), 3.47-3.39 (4H, m), 1.84 (1H, ddd, J=8.2, 5.9, 3.9 Hz), 1.29-1.23 (2H, m), 1.18-1.08 (1H, m), 0.41-0.36 (2H, m), 0.12-0.08 (2H, m).

The following compounds were prepared in analogy to Example 36 described above in detail with the exception that Pd(OAc)₂ was used instead of Pd(PPh₃)₄.

TABLE 6

| Ex. | Structure<br>Name<br>¹H-NMR | MS<br>[M + H]+ |
|---|---|---|
| 37 | 2-(5-((Cyclopropylmethyl)(5-(trifluoromethyl)naphthalen-1-yl)amino)-3-methoxypicolinoyl)cyclopropanecarboxylic acid<br>400 MHz (DMSO-d₆, ppm) δ 12.38 (1H, s), 8.19 (1H, dd, J = | 485 |

TABLE 6-continued

| Ex. | Structure<br>Name<br>¹H-NMR | MS<br>[M + H]+ |
|---|---|---|
| | 8.6, 1.5 Hz), 8.11-8.05 (2H, m), 7.91 (1H, dd, J = 8.7, 7.4 Hz), 7.79 (1H, dd, J = 7.3, 1.0 Hz), 7.68 (1H, t, J = 7.9 Hz), 7.29-7.21 (1H, m), 6.74-6.67 (1H, m), 3.91 (1H, br s), 3.76-3.58 (4H, m), 3.53 (1H, ddd, J = 8.5, 6.1, 3.9 Hz), 1.84 (1H, ddd, J = 8.3, 5.8, 3.9 Hz), 1.27 (2H, tdd, J = 5.7, 3.7, 2.9 Hz), 1.18-1.06 (1H, m), 0.44-0.31 (2H, m), 0.15-0.03 (2H, m) | |
| 38 | 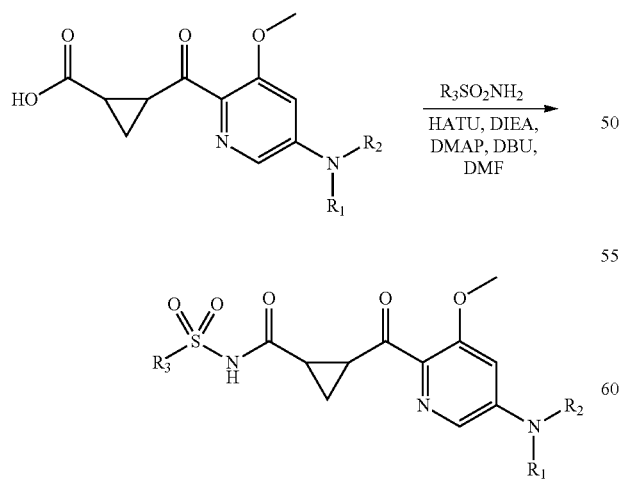<br>2-(5-((Cyclopropylmethyl)(1,2-dihydroacenaphthylen-3-yl)amino)-3-methoxypicolinoyl)cyclopropanecarboxylic acid<br>400 MHz (DMSO-$d_6$, ppm) δ 12.37 (1H, s), 7.80 (1H, dd, J = 8.6, 0.9 Hz), 7.70 (1H, dd, J = 8.3, 0.9 Hz), 7.56-7.49 (2H, m), 7.41 (1H, d, J = 8.6 Hz), 7.38-7.34 (1H, m), 6.64 (1H, d, J = 2.3 Hz), 3.76 (2H, app d, J = 6.8 Hz), 3.72 (3H, s), 3.64-3.58 (1H, m), 3.40-3.34 (2H, m), 3.17-3.10 (2H, m), 1.87 (1H, ddd, J = 8.0, 6.4, 3.9 Hz), 1.33-1.24 (2H, m), 1.20-1.08 (1H, m), 0.48-0.39 (2H, m), 0.15-0.07 (2H, m) | 443 |

Scheme I

A detailed illustrative synthetic procedure for the general procedure shown in Scheme I is described below.

Example 39

2-(5-((4-Chlorophenyl)(cyclopropylmethyl)amino)-3-methoxypicolinoyl)-N-(phenylsulfonyl)cyclopropanecarboxamide

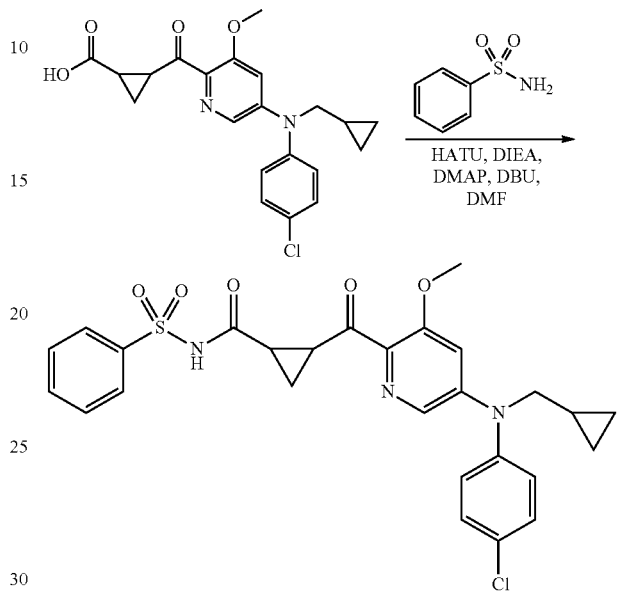

2-(5-((4-Chlorophenyl)(cyclopropylmethyl)amino)-3-methoxypicolinoyl)cyclopropanecarboxylic acid (20 mg, 0.05 mmol), HATU (21 mg, 0.06 mmol) and DIEA (23 mg, 0.18 mmol) were dissolved in DMF (1 mL). The mixture was stirred at rt for 1.5 h before the addition of benzenesulfonamide (28 mg, 0.18 mmol), DMAP (23 mg, 0.19 mmol) and DBU (29 mg, 0.19 mmol) in DMF. The reaction mixture was stirred at rt over weekend. The solvent was evaporated and the crude product was dissolved in DMSO: MeOH and purified by HPLC to give the title compound. Yield: 20 mg (82%). MS [M+H]+ 540. ¹H NMR 400 MHz (DMSO-$d_6$, ppm) δ 12.47 (1H, br s), 7.90-7.87 (2H, m), 7.69-7.64 (2H, m), 7.61-7.56 (2H, m), 7.54-7.50 (2H, m), 7.37-7.34 (2H, m), 6.73 (1H, d, J=2.3 Hz), 3.72 (3H, s), 3.70 (2H, app d, J=6.7 Hz), 3.49-3.44 (1H, m), 2.16-2.10 (1H, m), 1.28-1.18 (2H, m), 1.13-1.04 (1H, m), 0.46-0.41 (2H, m), 0.16-0.12 (2H, m).

The following compounds were prepared in analogy to Example 39 described above in detail.

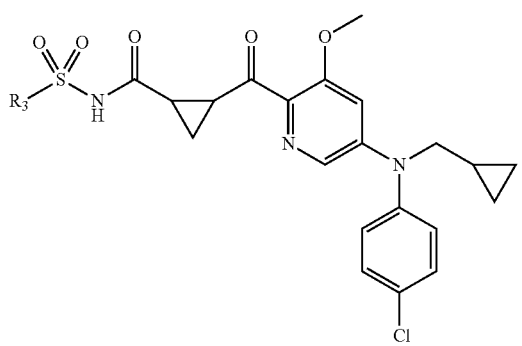

TABLE 7

| Ex. | R$_3$ | MS [M + H]$^+$ $^1$H-NMR | Name |
|---|---|---|---|
| 40 | cyclopropyl | 504 | 2-(5-((4-Chlorophenyl)(cyclopropylmethyl)amino)-3-methoxypicolinoyl)-N-(cyclopropylsulfonyl)-cyclopropanecarboxamide |

400 MHz (DMSO-d$_6$, ppm) δ 12.02 (1H, s), 7.69 (1H, d, J = 2.3 Hz), 7.55-7.51 (2H, m), 7.39-7.35 (2H, m), 6.75 (1H, d, J = 2.3 Hz), 3.76 (3H, s), 3.72 (2H, app d, J = 6.7 Hz), 3.66-3.61 (1H, m), 2.98-2.91 (1H, m), 2.24-2.19 (1H, m), 1.37-1.33 (2H, m), 1.13-1.04 (5H, m), 0.47-0.42 (2H, m), 0.17-0.13 (2H, m)

| 41 | 4-methoxyphenyl | 570 | 2-(5-((4-Chlorophenyl)(cyclopropylmethyl)amino)-3-methoxypicolinoyl)-N-((4-methoxyphenyl)sulfonyl)-cyclopropanecarboxamide |

400 MHz (DMSO-d$_6$, ppm) δ 12.31 (1H, s), 7.85-7.81 (2H, m), 7.65 (1H, d, J = 2.3 Hz), 7.54-7.50 (2H, m), 7.37-7.33 (2H, m), 7.12-7.08 (2H, m), 6.73 (1H, d, J = 2.4 Hz), 3.84 (3H, s), 3.72 (3H, s), 3.70 (2H, app d, J = 6.7 Hz), 3.47 (1H, ddd, J = 8.7, 6.0, 3.8 Hz), 2.16-2.11 (1H, m), 1.29-1.19 (2H, m), 1.13-1.03 (1H, m), 0.46-0.41 (2H, m), 0.16-0.12 (2H, m)

| 42 | 4-(trifluoromethoxy)phenyl | 624 | 2-(5-((4-Chlorophenyl)(cyclopropylmethyl)amino)-3-methoxypicolinoyl)-N-((4-(trifluoromethoxy)phenyl)-sulfonyl)cyclopropanecarboxamide |

400 MHz (DMSO-d$_6$, ppm) δ 12.63 (1H, br s), 8.05-8.01 (2H, m), 7.64 (1H, d, J = 2.3 Hz), 7.61-7.57 (2H, m), 7.54-7.50 (2H, m), 7.37-7.33 (2H, m), 6.73 (1H, d, J = 2.3 Hz), 3.73 (3H, s), 3.70 (2H, app d, J = 6.7 Hz), 3.48 (1H, ddd, J = 8.7, 6.1, 3.9 Hz), 2.18-2.12 (1H, m), 1.31-1.21 (2H, m), 1.13-1.03 (1H, m), 0.46-0.41 (2H, m), 0.16-0.12 (2H, m)

| 43 | 2-fluorophenyl | 558 | 2-(5-((4-Chlorophenyl)(cyclopropylmethyl)amino)-3-methoxypicolinoyl)-N-((2-fluorophenyl)sulfonyl)-cyclopropanecarboxamide |

400 MHz (DMSO-d$_6$, ppm) δ 12.86 (1H, br s), 7.91-7.85 (1H, m), 7.77-7.69 (1H, m), 7.65 (1H, d, J = 2.3 Hz), 7.55-7.50 (2H, m), 7.46-7.34 (4H, m), 6.74 (1H, d, J = 2.3 Hz), 3.74 (3H, s), 3.71 (2H, app d, J = 6.7 Hz), 3.50-3.44 (1H, m), 2.25-2.14 (1H, m), 1.31-1.18 (2H, m), 1.14-1.04 (1H, m), 0.47-0.42 (2H, m), 0.16-0.12 (2H, m)

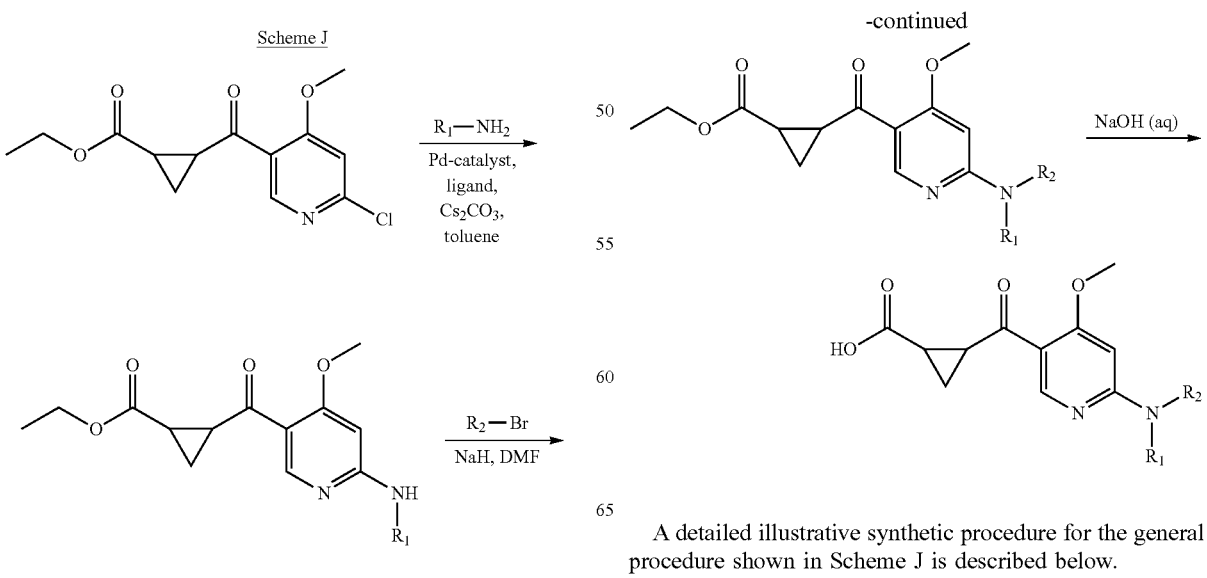

Scheme J

A detailed illustrative synthetic procedure for the general procedure shown in Scheme J is described below.

Example 44

2-(6-(Cyclopropylmethyl)(4-methylnaphthalen-1-yl)amino)-4-methoxynicotinoyl)cyclopropanecarboxylic acid

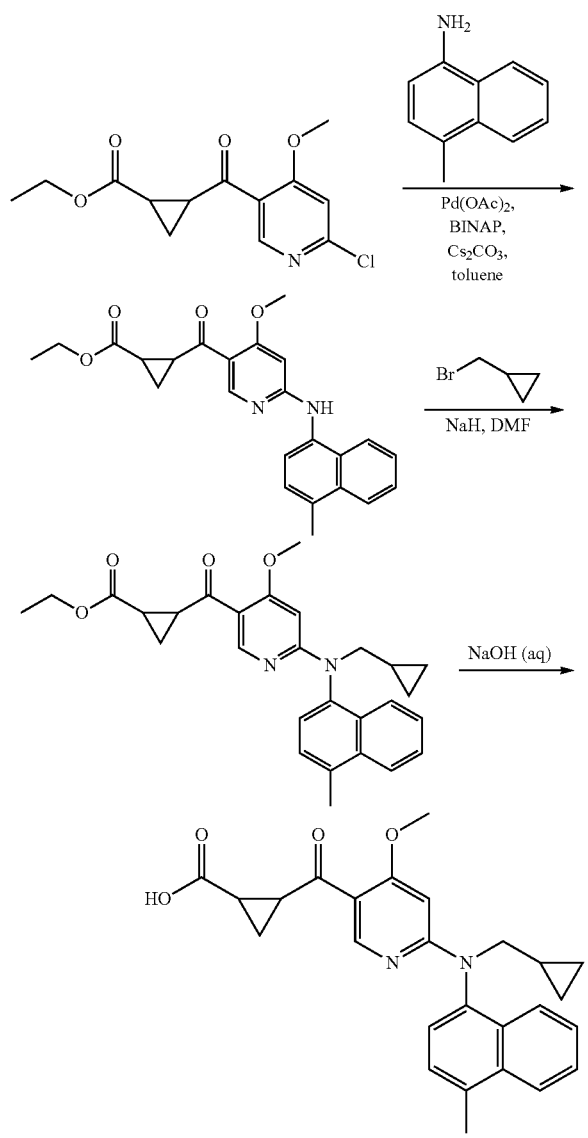

Ethyl 2-(4-methoxy-6-((4-methylnaphthalen-1-yl)amino)nicotinoyl)cyclopropanecarboxylate Ethyl 2-(6-chloro-4-methoxynicotinoyl)cyclopropanecarboxylate (110 mg, 0.39 mmol), 4-methylnaphthalen-1-amine (122 mg, 0.78 mmol), Pd(OAc)$_2$ (4.4 mg, 0.019 mmol), rac-BINAP (19 mg, 0.031 mmol) and Cs$_2$CO$_3$ (177 mg, 0.54 mmol) were mixed in toluene (2.5 mL) and stirred at 95° C. for 16 h in a sealed tube. The reaction mixture was diluted (EtOAc), filtered through a celite pad and concentrated. Purification by column chromatography afforded the sub-title compound. Yield: 35 mg (23%).

Ethyl 2-(6-((cyclopropylmethyl)(4-methylnaphthalen-1-yl)amino)-4-methoxynicotinoyl)cyclopropanecarboxylate NaH (60% dispersion in mineral oil, 9 mg, 0.3 mmol) was added in one portion a to solution of ethyl 2-(4-methoxy-6-((4-methylnaphthalen-1-yl)amino)nicotinoyl)cyclopropanecarboxylate (98 mg, 0.24 mmol) and (bromomethyl)cyclopropane (59 µL, 0.73 mmol) in DMF (3 mL) at 0° C. The reaction mixture stirred at rt for 18 h then quenched with water. Extractive workup (EtOAc, water, brine) and concentration of the EtOAc extracts followed by column chromatography afforded sub-title compound. Yield: 50 mg (45%).

2-(6-(Cyclopropylmethyl)(4-methylnaphthalen-1-yl)amino)-4-methoxynicotinoyl)cyclopropanecarboxylic acid A mixture of ethyl 2-(6-((cyclopropylmethyl)(4-methylnaphthalen-1-yl)amino)-4-methoxynicotinoyl)cyclopropanecarboxylate (70 mg, 0.15 mmol) and NaOH (31 mg, 0.76 mmol) in EtOH (3 mL) and water (1 mL) was stirred at rt for 4 h. The reaction mixture was acidified with 1M aq HCl (pH~5) and EtOH was partly evaporated. Extraction with EtOAc, drying (Na$_2$SO$_4$) and concentration afforded the title compound. Yield: 30 mg (46%). MS [M+H]$^+$ 431. $^1$H-NMR 400 MHz (CDCl$_3$, ppm) δ 8.63 (1H, s), 8.07 (1H, d, J=8.4 Hz), 7.78 (1H, d, J=8.4 Hz), 7.59-7.55 (1H, m), 7.49-7.45 (1H, m), 7.40 (2H, s), 5.28 (1H, s), 4.31 (1H, dd, J=14.1, 6.6 Hz), 3.64-3.59 (1H, m), 3.35 (3H, s), 3.24-3.19 (1H, m), 2.76 (3H, s), 2.22-2.18 (1H, m), 1.67-1.63 (1H, m), 1.47-1.43 (1H, m), 1.20-1.10 (1H, m), 0.44-0.32 (2H, m), 0.16-0.06 (2H, m).

Scheme K

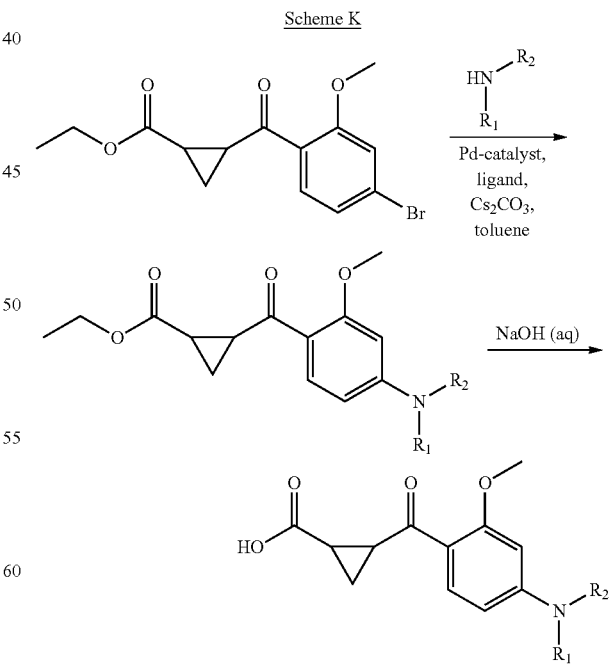

A detailed illustrative synthetic procedure for the general procedure shown in Scheme K is described below.

Example 45

2-(4-((Cyclopropylmethyl)(4-methylnaphthalen-1-yl)amino)-2-methoxybenzoyl)cyclopropanecarboxylic acid

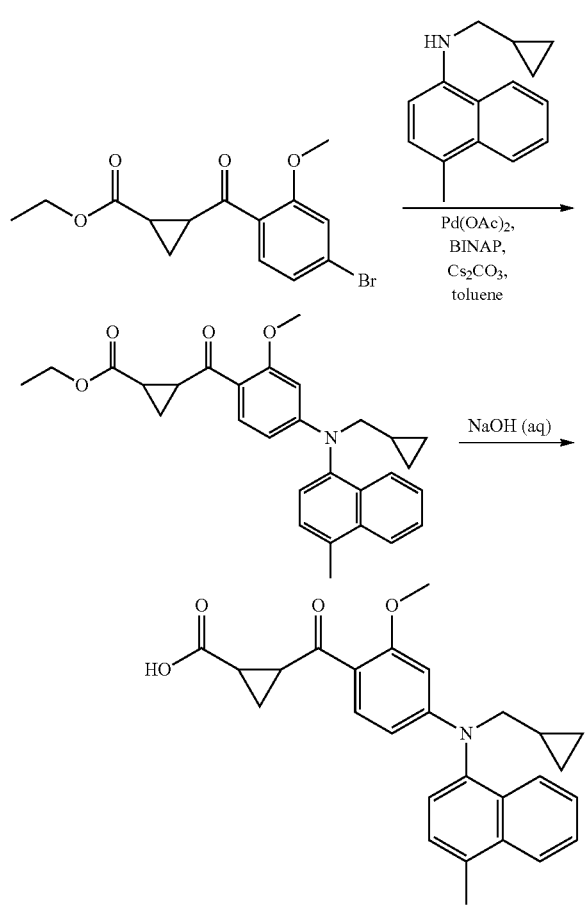

Ethyl 2-(4-((cyclopropylmethyl)(4-methylnaphthalen-1-yl)amino)-2-methoxybenzoyl)cyclopropanecarboxylate Ethyl 2-(4-bromo-2-methoxybenzoyl)cyclopropanecarboxylate (193 mg, 0.59 mmol), N-(cyclopropylmethyl)-4-methylnaphthalen-1-amine (150 mg, 0.71 mmol), Pd(OAc)$_2$ (6.7 mg, 0.030 mmol), rac-BINAP (28 mg, 0.044 mmol) and Cs$_2$CO$_3$ (288 mg, 0.89 mmol) were mixed in toluene (3 mL) and stirred at 80° C. for 16 h in a sealed tube. The reaction mixture was diluted (EtOAc), filtered through a celite pad and concentrated. Purification by column chromatography afforded the sub-title compound. Yield: 145 mg (54%).

2-(4-((Cyclopropylmethyl)(4-methylnaphthalen-1-yl)amino)-2-methoxybenzoyl)cyclopropanecarboxylic acid A mixture of ethyl 2-(4-((cyclopropylmethyl)(4-methylnaphthalen-1-yl)amino)-2-methoxybenzoyl)cyclopropanecarboxylate (145 mg, 0.32 mmol) and NaOH (63 mg, 1.58 mmol) in EtOH (2 mL) and water (1 mL) was stirred at rt for 2 h. The EtOH was partly evaporated and the reaction mixture was acidified with 1M aq HCl (pH~3) at 0° C. Filtration of the precipitate followed by washing (H$_2$O) and drying afforded the title compound. Yield: 100 mg (74%). MS [M+H]$^+$ 430. $^1$H-NMR 400 MHz (CDCl$_3$, ppm) δ 10.8 (1H, br s), 8.06 (1H, d, J=8.4 Hz), 7.75 (1H, d, J=8.4 Hz), 7.62 (1H, d, J=9.0 Hz), 7.57-7.53 (1H, m), 7.47-7.42 (1H, m), 7.39-7.35 (2H, m), 6.20 (1H, d, J=8.4 Hz), 6.01 (1H, s), 3.98-3.86 (1H, m), 3.62 (3H, s), 3.42-3.37 (2H, m), 2.75 (3H, s), 2.21-2.17 (1H, m), 1.69-1.64 (1H, m), 1.48-1.43 (1H, m), 1.27-1.17 (1H, m), 0.50-0.42 (2H, m), 0.13-0.06 (2H, m).

The following compounds were prepared in analogy to Example 45 described above in detail unless otherwise indicated.

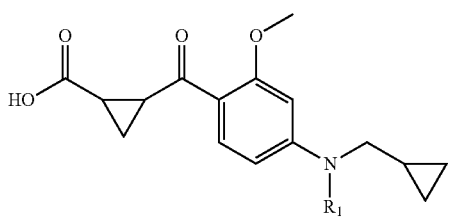

TABLE 8

| Ex. | R$_1$ | MS [M + H]$^+$<br>Name<br>$^1$H-NMR | Pd-catalyst and ligand according to Scheme K |
|---|---|---|---|
| 46 | 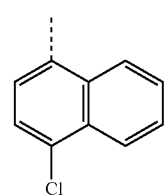 | 434 | Pd(OAc)$_2$, BINAP |
|  | 2-(4-((Cyclopropylmethyl)(4-fluoronaphthalen-1-yl)amino)-2-methoxybenzoyl)cyclopropanecarboxylic acid | | |
|  | 400 MHz (CDCl$_3$, ppm) δ 10.3 (1H, br s), 8.17 (1H, d, J = 8.4 Hz), 7.73 (1H, d, J = 8.4 Hz), 7.63 (1H, d, J = 8.8 Hz), 7.60-7.56 (1H, m), 7.52-7.48 (1H, m), 7.42-7.19 (2H, m), 6.21 (1H, d, J = 8.4 Hz), 5.98 (1H, s), 4.00-3.63 (1H, m), 3.62 (3H, s), 3.61-3.33 (1H, m), 3.41-3.36 (1H, m), 2.21-2.17 (1H, m), 1.69-1.64 (1H, m), 1.48-1.44 (1H, m), 1.23-1.15 (1H, m), 0.50-0.42 (2H, m), 0.13-0.01 (2H, m) | | |
| 47 |  | 450 | Pd(OAc)$_2$, BINAP |
|  | 2-(4-((4-Chloronaphthalen-1-yl)(cyclopropylmethyl)amino)-2-methoxybenzoyl)cyclopropanecarboxylic acid | | |
|  | 400 MHz (CDCl$_3$, ppm) δ 8.34 (1H, d, J = 8.8 Hz), 7.78 (1H, d, J = 8.4 Hz), 7.66-7.62 (3H, m), 7.53-7.49 (1H, m), 7.40 (1H, d, J = 8.4 Hz), 6.21 (1H, d, J = 8.4 Hz), 5.99 (1H, s), 3.85-3.43 (2H, m), 3.63 (3H, s), 3.40-3.36 (1H, m), 2.22-2.17 (1H, m), 1.69-1.65 (1H, m), 1.49-1.44 (1H, m), 1.24-1.15 (1H, m), 0.49-0.44 (2H, m), 0.07-0.03 (2H, m) | | |

TABLE 8-continued

| Ex. | R₁ | MS [M + H]⁺ Name ¹H-NMR | Pd-catalyst and ligand according to Scheme K |
|---|---|---|---|
| 48 | naphthalen-1-yl | 416 | Pd(OAc)₂, BINAP |

2-(4-((Cyclopropylmethyl)(naphthalen-1-yl)amino)-2-methoxybenzoyl)cyclopropanecarboxylic acid
400 MHz (CDCl₃, ppm) δ 7.92 (1H, d, J = 7.2 Hz), 7.87 (1H, d, J = 8.0 Hz), 7.74 (1H, d, J = 8.0 Hz), 7.63 (1H, d, J = 8.0 Hz), 7.57-7.42 (4H, m), 6.21 (1H, d, J = 8.6 Hz), 6.00 (1H, s), 3.87-3.47 (2H, m), 3.61 (3H, s), 3.41-3.36 (1H, m), 2.21-2.16 (1H, m), 1.68-1.64 (1H, m), 1.48-1.43 (1H, m), 1.27-1.17 (1H, m), 0.48-0.44 (2H, m), 0.08-0.04 (2H, m)

| 49 | 4-chlorophenyl | 400 | Pd(OAc)₂, BINAP |

2-(4-((4-Chlorophenyl)(cyclopropylmethyl)amino)-2-methoxybenzoyl)cyclopropanecarboxylic acid
400 MHz (DMSO-d₆, ppm) δ 12.4 (1H, br s), 7.53-7.49 (2H, m), 7.47 (1H, d, J = 8.8 Hz), 7.33-7.29 (2H, m), 6.41 (1H, d, J = 2.1 Hz), 6.33 (1H, dd, J = 8.8, 2.1 Hz), 3.79 (3H, s), 3.68 (2H, d, J = 6.5 Hz), 3.23-3.16 (1H, m), 1.95-1.89 (1H, m), 1.47-1.40 (1H, m), 1.36-1.30 (1H, m), 1.15-1.06 (1H, m), 0.48-0.42 (2H, m), 0.17-0.11 (2H, m)

| 50 | 3,4-dimethylphenyl | 394 | Pd(OAc)₂, BINAP |

2-(4-((Cyclopropylmethyl)(3,4-dimethylphenyl)amino)-2-methoxybenzoyl)cyclopropanecarboxylic acid
400 MHz (DMSO-d₆, ppm) δ 7.44 (1H, d, J = 8.9 Hz), 7.23 (1H, d, J = 7.9 Hz), 7.07 (1H, d, J = 2.0 Hz), 7.01 (1H, dd, J = 7.9, 2.0 Hz), 6.33 (1H, d, J = 2.0 Hz), 6.19 (1H, dd, J = 8.9, 2.0 Hz), 3.77 (3H, s), 3.63 (2H, app d, J = 6.5 Hz), 3.23-3.17 (1H, m), 2.26 (3H, s), 2.25 (3H, s), 1.93-1.86 (1H, m), 1.45-1.38 (1H, m), 1.34-1.27 (1H, m), 1.15-1.06 (1H, m), 0.49-0.42 (2H, m), 0.18-0.12 (2H, m)

| 51 | 4-chlorobenzyl | 414 | Pd(OAc)₂, BINAP |

2-(4-((4-Chlorobenzyl)(cyclopropylmethyl)amino)-2-methoxybenzoyl)cyclopropanecarboxylic acid
400 MHz (DMSO-d₆, ppm) δ 12.4 (1H, br s), 7.48 (1H, d, J = 8.9 Hz), 7.42-7.37 (2H, m), 7.30-7.25 (2H, m), 6.38 (1H, dd, J = 8.9, 2.0 Hz), 6.27 (1H, d, J = 2.0 Hz), 4.76 (2H, s), 3.77 (3H, s), 3.46 (2H, app d, J = 6.5 Hz), 3.23-3.16 (1H, m), 1.92-1.86 (1H, m), 1.43-1.37 (1H, m), 1.32-1.26 (1H, m), 1.20-1.11 (1H, m), 0.52-0.46 (2H, m), 0.34-0.28 (2H, m)

| 52 | 8-methylquinolin-5-yl | 431 | Pd(OAc)₂, Xantphos |

2-(4-((Cyclopropylmethyl)(8-methylquinolin-5-yl)amino)-2-methoxybenzoyl)cyclopropanecarboxylic acid
400 MHz (CDCl₃, ppm) δ 8.99 (1H, dd, J = 4.2, 1.7 Hz), 8.08 (1H, dd, J = 8.5, 1.7 Hz), 7.67-7.59 (2H, m), 7.43 (1H, d, J = 7.5 Hz), 7.36 (1H, dd, J = 8.5, 4.2 Hz), 6.24-6.16 (1H, m), 6.00-5.92 (1H, m), 3.80-3.50 (5H, m), 3.41-3.33 (1H, m), 2.87 (3H, s), 2.23-2.16 (1H, m), 1.70-1.61 (1H, m), 1.50-1.42 (1H, m), 1.22-1.13 (1H, m), 0.50-0.36 (2H, m), 0.11-0.00 (2H, m)

Scheme L

A detailed illustrative synthetic procedure for the general procedure shown in Scheme L is described below.

Example 53

2-(4-((Cyclopropylmethyl)(5-(trifluoromethyl)quinolin-8-yl)amino)-2-methoxybenzoyl)cyclopropanecarboxylic acid

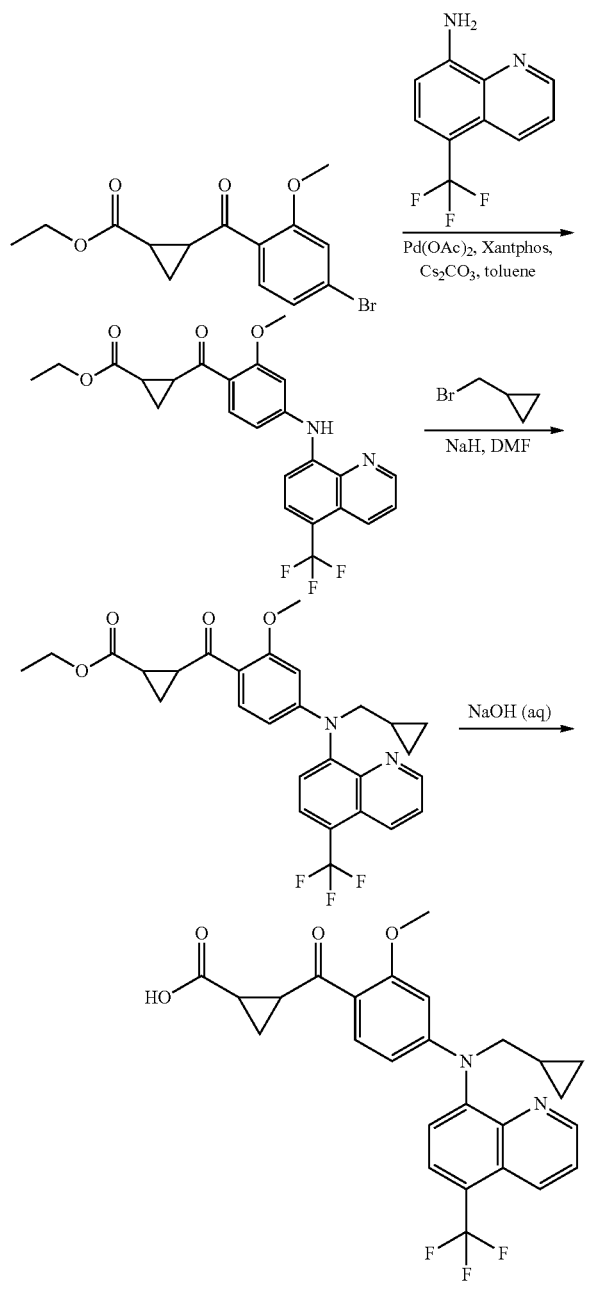

Ethyl 2-(2-methoxy-4-((5-(trifluoromethyl)quinolin-8-yl)amino)benzoyl)cyclopropanecarboxylate Ethyl 2-(4-bromo-2-methoxybenzoyl)cyclopropanecarboxylate (137 mg, 0.42 mmol), 5-(trifluoromethyl)quinolin-8-amine (90 mg, 0.42 mmol), Pd(OAc)$_2$ (9.4 mg, 0.042 mmol), Xantphos (36 mg, 0.062 mmol) and Cs$_2$CO$_3$ (205 mg, 0.63 mmol) were mixed in toluene (3 mL) and stirred at 120° C. for 48 h in a sealed tube. The reaction mixture was diluted (EtOAc), filtered through a celite pad and concentrated. Purification by column chromatography afforded the sub-title compound. Yield: 125 mg (65%).

Ethyl 2-(4-((cyclopropylmethyl)(5-(trifluoromethyl)quinolin-8-yl)amino)-2-methoxybenzoyl)cyclopropanecarboxylate NaH (60% dispersion in mineral oil, 11 mg, 0.28 mmol) was added in one portion to a solution of ethyl 2-(2-methoxy-4-((5-(trifluoromethyl)quinolin-8-yl)amino)benzoyl)cyclopropanecarboxylate (125 mg, 0.27 mmol) in DMF (2 mL) at 0° C. After stirring at 0° C. for 5 min (bromomethyl)cyclopropane (51 μL, 0.52 mmol) was added. The reaction mixture stirred at rt for 72 h then quenched with water. Extractive workup (EtOAc, water, brine) and concentration of the EtOAc extracts followed by column chromatography afforded the sub-title compound. Yield: 50 mg (36%).

2-(4-((Cyclopropylmethyl)(5-(trifluoromethyl)quinolin-8-yl)amino)-2-methoxybenzoyl)cyclopropanecarboxylic acid A mixture of ethyl 2-(4-((cyclopropylmethyl)(5-(trifluoromethyl)quinolin-8-yl)amino)-2-methoxybenzoyl)cyclopropanecarboxylate (40 mg, 0.078 mmol) and NaOH (160 mg, 4.0 mmol) in EtOH (2 mL) and water (2 mL) was stirred at 80° C. for 30 min. The reaction mixture was acidified with 1M aq HCl (pH~3) at 0° C. Filtration of the precipitate followed by washing (H$_2$O) and drying afforded the title compound. Yield: 36 mg (95%). MS [M+H]$^+$ 485. $^1$H-NMR 400 MHz (DMSO-d$_6$, ppm) δ 12.43 (1H, s), 8.98 (1H, dd, J=4.1, 1.6 Hz), 8.58-8.53 (1H, m), 8.19 (1H, d, J=7.9 Hz), 7.93 (1H, d, J=7.9 Hz), 7.77 (1H, dd, J=8.8, 4.1 Hz), 7.34 (1H, d, J=8.8 Hz), 6.37 (1H, d, J=2.1 Hz), 5.99 (1H, dd, J=8.8, 2.1 Hz), 3.83 (2H, app d, J=6.7 Hz), 3.76 (3H, s), 3.21-3.15 (1H, m), 1.91-1.85 (1H, m), 1.43-1.36 (1H, m), 1.33-1.26 (1H, m), 1.14-1.04 (1H, m), 0.38-0.30 (2H, m), 0.06-0.01 (2H, m).

Scheme M

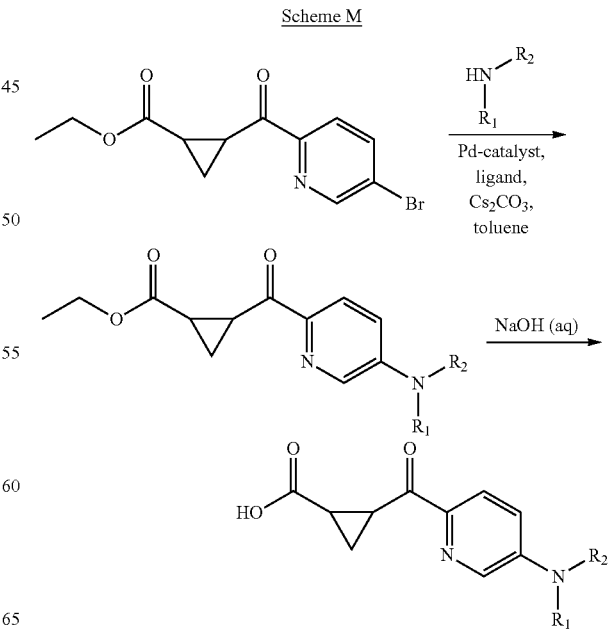

A detailed illustrative synthetic procedure for the general procedure shown in Scheme M is described below.

Example 54

2-(5-((4-Chlorophenyl)(cyclopropylmethyl)amino)picolinoyl)cyclopropanecarboxylic acid

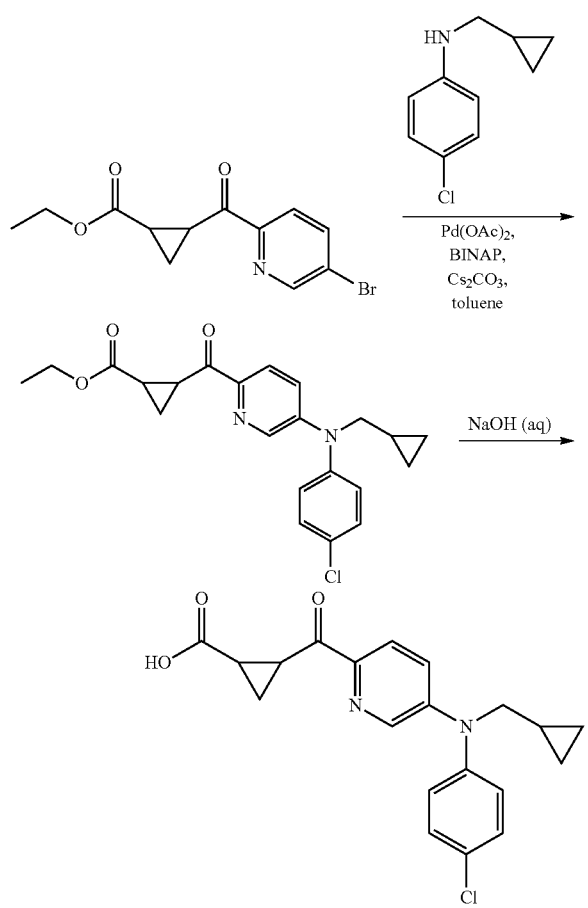

Ethyl 2-(5-((4-chlorophenyl)(cyclopropylmethyl)amino)picolinoyl)cyclopropanecarboxylate Prepared in analogy to example 45 step (a) using ethyl 2-(5-bromopicolinoyl)cyclopropanecarboxylate (109 mg, 0.37 mmol), 4-chloro-N-(cyclopropylmethyl)aniline (80 mg, 0.44 mmol), Pd(OAc)$_2$ (4 mg, 0.018 mmol), rac-BINAP (17 mg, 0.027 mmol), Cs$_2$CO$_3$ (176 mg, 0.54 mmol) and toluene (2 mL) at 80° C. for 24 h. Yield: 120 mg (82%).

2-(5-((4-Chlorophenyl)(cyclopropylmethyl)amino)picolinoyl)cyclopropanecarboxylic acid Prepared in analogy to example 45 step (b) using ethyl 2-(5-((4-chlorophenyl)(cyclopropylmethyl)amino)picolinoyl)cyclopropanecarboxylate (120 mg, 0.30 mmol), NaOH (48 mg, 1.20 mmol), EtOH (4 mL) and water (2 mL) at 60° C. for 3 h followed by column chromatography. Yield: 55 mg (50%). MS [M+H]$^+$ 371. $^1$H-NMR 400 MHz (DMSO-d$_6$, ppm) δ 12.5 (1H, br s), 8.18 (1H, d, J=3.0 Hz), 7.81 (1H, d, J=9.0 Hz), 7.56-7.51 (2H, m), 7.39-7.33 (2H, m), 7.20 (1H, dd, J=9.0, 3.0 Hz), 3.80-3.74 (1H, m), 3.70 (2H, app d, J=6.7 Hz), 2.02-1.95 (1H, m), 1.46-1.34 (2H, m), 1.14-1.03 (1H, m), 0.49-0.38 (2H, m), 0.18-0.09 (2H, m).

The following compound was prepared in analogy to Example 54 described above in detail.

TABLE 9

| Ex. | Structure<br>Name<br>$^1$H-NMR | MS [M + H]+ |
| --- | --- | --- |
| 55 | 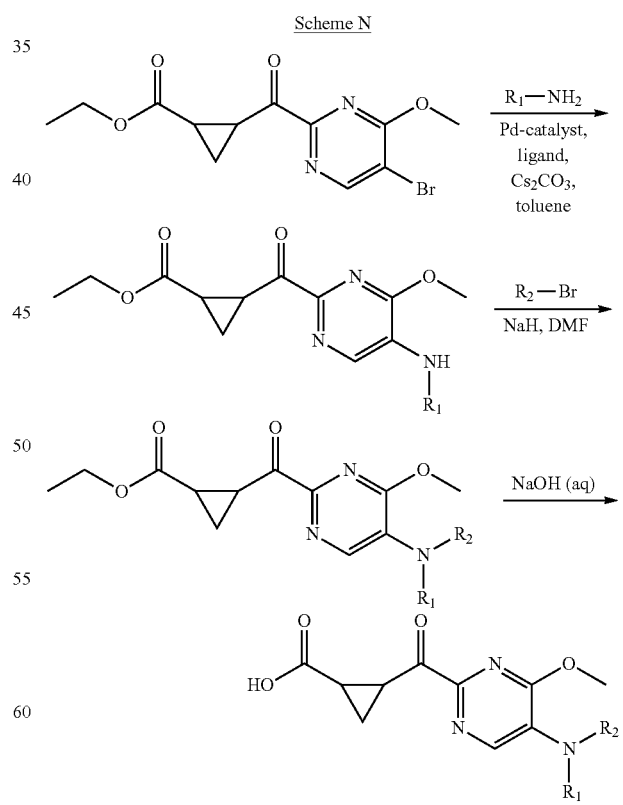<br>2-(5-((4-Chlorobenzyl)(cyclopropylmethyl)amino)picolinoyl)cyclopropanecarboxylic acid<br>400 MHz (DMSO-d$_6$, ppm) δ 12.5 (1H, br s), 8.20 (1H, d, J = 3.0 Hz), 7.78 (1H, d, J = 9.0 Hz), 7.41-7.36 (2H, m), 7.29-7.23 (2H, m), 7.17 (1H, dd, J = 9.0, 3.0 Hz), 4.81 (2H, app s), 3.79-3.72 (1H, m), 3.52 (2H, app d, J = 6.6 Hz), 1.99-1.92 (1H, m), 1.42-1.32 (2H, m), 1.20-1.09 (1H, m), 0.54-0.44 (2H, m), 0.35-0.27 (2H, m) | 385 |

Scheme N

A detailed illustrative synthetic procedure for the general procedure shown in Scheme N is described below.

Example 56

2-(5-((4-Chloronaphthalen-1-yl)(cyclopropylmethyl)amino)-4-methoxypyrimidine-2-carbonyl)cyclopropanecarboxylic acid

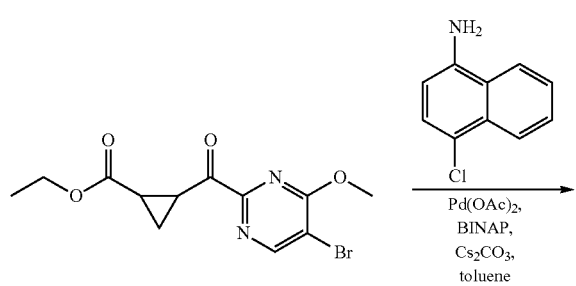

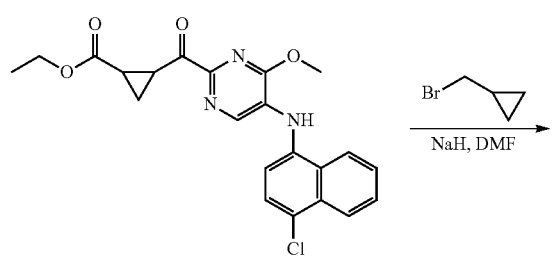

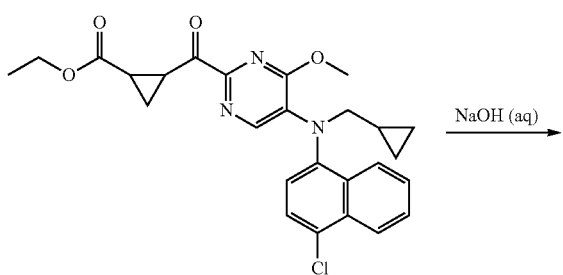

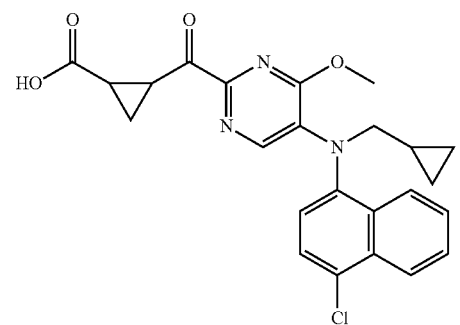

Ethyl 2-(5-((4-chloronaphthalen-1-yl)amino)-4-methoxypyrimidine-2-carbonyl)cyclopropanecarboxylate Ethyl 2-(5-bromo-4-methoxypyrimidine-2-carbonyl)cyclopropanecarboxylate (100 mg, 0.30 mmol), 4-chloronaphthalen-1-amine (65 mg, 0.37 mmol), Pd(OAc)$_2$ (3.4 mg, 0.015 mmol), rac-BINAP (14 mg, 0.023 mmol) and Cs$_2$CO$_3$ (139 mg, 0.43 mmol) were mixed in toluene (1 mL) and stirred at 85° C. for 20 h in a sealed tube. The reaction mixture was diluted (EtOAc), filtered through a celite pad and concentrated. Purification by column chromatography afforded the sub-title compound. Yield: 80 mg (62%).

Ethyl 2-(5-((4-chloronaphthalen-1-yl)(cyclopropylmethyl)amino)-4-methoxypyrimidine-2-carbonyl)cyclopropanecarboxylate NaH (60% dispersion in mineral oil, 8 mg, 0.20 mmol) was added in one portion to solution of ethyl 2-(5-((4-chloronaphthalen-1-yl)amino)-4-methoxypyrimidine-2-carbonyl)cyclopropanecarboxylate (80 mg, 0.19 mmol) and (bromomethyl)cyclopropane (36 µL, 0.38 mmol) in DMF (2 mL) at 0° C. The reaction mixture stirred at 70° C. for 1 h then quenched with water. Extractive workup (EtOAc, water, brine) and concentration of the EtOAc extracts followed by column chromatography afforded the sub-title compound. Yield: 80 mg (89%).

2-(5-((4-Chloronaphthalen-1-yl)(cyclopropylmethyl)amino)-4-methoxypyrimidine-2-carbonyl)cyclopropanecarboxylic acid A mixture of ethyl 2-(5-((4-chloronaphthalen-1-yl)(cyclopropylmethyl)amino)-4-methoxypyrimidine-2-carbonyl)cyclopropanecarboxylate (80 mg, 0.17 mmol) and NaOH (32 mg, 0.83 mmol) in EtOH (4 mL) and water (1 mL) was stirred at 70° C. for 30 min. The reaction mixture was acidified with 1M aq HCl (pH~3) at 0° C. Filtration of the precipitate followed by washing (H$_2$O) and drying afforded the title compound. Yield: 59 mg (78%). MS [M+H]$^+$ 452. $^1$H-NMR 400 MHz (CDCl$_3$, ppm) δ 8.32-8.28 (1H, m), 7.96 (1H, s), 7.95-7.91 (1H, m), 7.63-7.57 (1H, m), 7.54 (1H, d, J=7.9 Hz), 7.52-7.47 (1H, m), 7.25 (1H, d, J=7.9 Hz), 3.88-3.81 (4H, m), 3.72 (2H, app d, J=6.5 Hz), 2.32-2.25 (1H, m), 1.64-1.54 (2H, m), 1.17-1.09 (1H, m), 0.43-0.37 (2H, m), 0.05-0.00 (2H, m).

The following compounds were prepared in analogy to Example 56 described above in detail unless otherwise indicated.

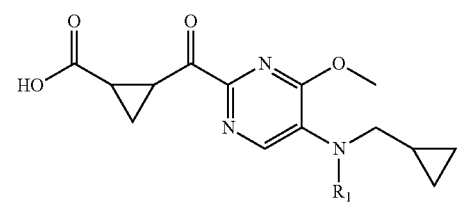

TABLE 10

| Ex. | R₁ | MS [M + H]⁺ | Name<br>¹H-NMR |
|---|---|---|---|
| 57 | naphthalen-1-yl | 418 | 2-(5-((Cyclopropylmethyl)(naphthalen-1-yl)amino)-4-methoxypyrimidine-2-carbonyl)cyclopropanecarboxylic acid |

400 MHz (CDCl₃, ppm) δ 7.90-7.85 (3H, m), 7.81-7.77 (1H, m), 7.52-7.40 (3H, m), 7.36 (1H, dd, J = 7.3, 1.0 Hz), 3.90 (3H, s), 3.90-3.84 (1H, m), 3.78 (2H, app d, J = 6.5 Hz), 2.34-2.28 (1H, m), 1.68-1.56 (2H, m), 1.20-1.12 (1H, m), 0.43-0.37 (2H, m), 0.07-0.01 (2H, m)

| 58 | 4-fluoronaphthalen-1-yl | 436 | 2-(5-((Cyclopropylmethyl)(4-fluoronaphthalen-1-yl)amino)-4-methoxypyrimidine-2-carbonyl)cyclopropanecarboxylic acid |

400 MHz (CDCl₃, ppm) δ 8.17-8.11 (1H, m), 7.91 (1H, s), 7.91-7.86 (1H, m), 7.59-7.53 (1H, m), 7.53-7.47 (1H, m), 7.27 (1H, dd, J = 8.1 4.9 Hz), 7.12 (1H, dd, J = 9.9 8.1 Hz), 3.90-3.84 (1H, m), 3.87 (3H, s), 3.73 (2H, app d, J = 6.5 Hz), 2.35-2.29 (1H, m), 1.69-1.57 (2H, m), 1.18-1.09 (1H, m), 0.44-0.37 (2H, m), 0.05-0.00 (2H, m)

| 59 | 4-methylnaphthalen-1-yl | 432 | 2-(5-((Cyclopropylmethyl)(4-methylnaphthalen-1-yl)amino)-4-methoxypyrimidine-2-carbonyl)cyclopropanecarboxylic acid |

400 MHz (CDCl₃, ppm) δ 8.05-8.00 (1H, m), 7.91-7.87 (1H, m), 7.80 (1H, s), 7.55-7.50 (1H, m), 7.46-7.41 (1H, m), 7.32-7.26 (2H, m), 3.93 (3H, s), 3.90-3.84 (1H, m), 3.77 (2H, app d, J = 6.5 Hz), 2.72 (3H, s), 2.34-2.28 (1H, m), 1.67-1.56 (2H, m), 1.20-1.11 (1H, m), 0.42-0.36 (2H, m), 0.07-0.02 (2H, m)

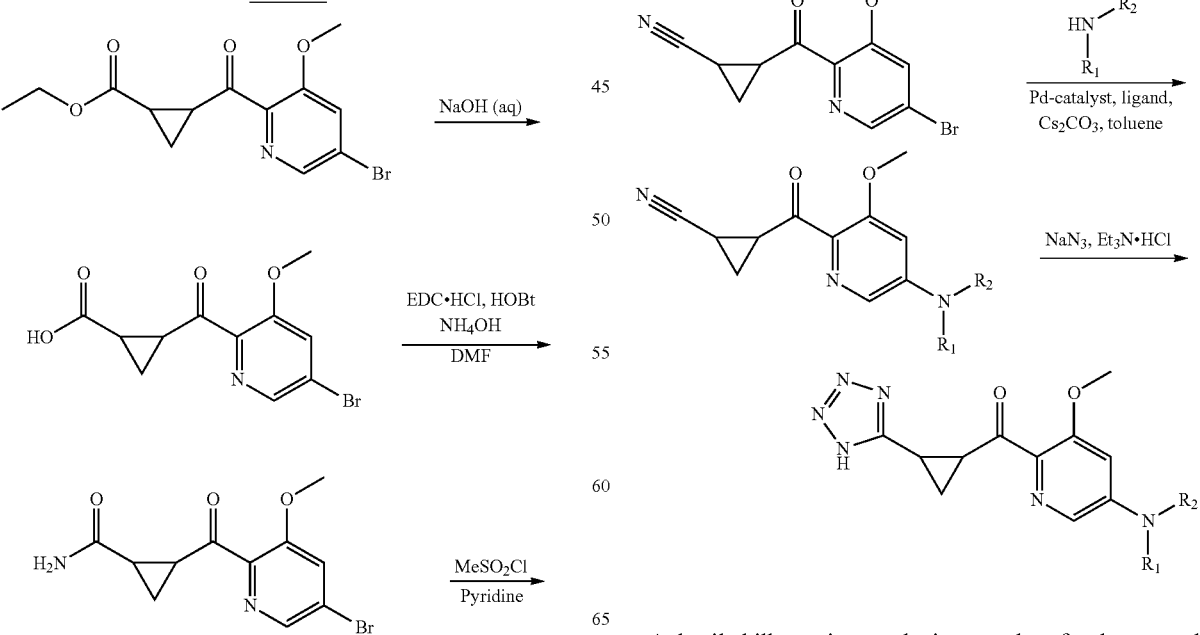

Scheme O

A detailed illustrative synthetic procedure for the general procedure shown in Scheme O is described below.

Example 60

(2-(1H-Tetrazol-5-yl)cyclopropyl)(5-((cyclopropylmethyl)(naphthalen-1-yl)amino)-3-methoxypyridin-2-yl)methanone

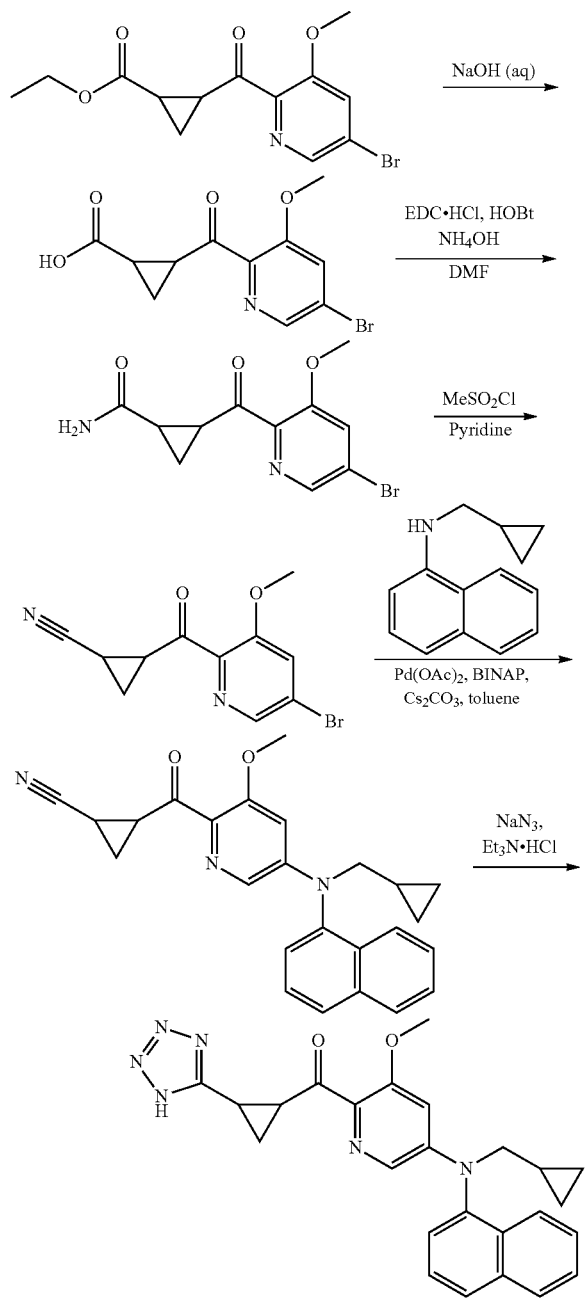

2-(5-Bromo-3-methoxypicolinoyl)cyclopropanecarboxylic acid

A mixture of ethyl 2-(5-bromo-3-methoxypicolinoyl)cyclopropanecarboxylate (1.32 g, 4.01 mmol) and NaOH (803 mg, 20.1 mmol) in EtOH (30 mL) and water (3 mL) was stirred at 80° C. for 30 min. The reaction mixture was acidified with 1M aq HCl (pH~5) and EtOH was partly evaporated. Extraction with EtOAc, drying (Na$_2$SO$_4$) and concentration of EtOAc extracts afforded the sub-title compound. Yield: 1.20 g (99%).

2-(5-Bromo-3-methoxypicolinoyl)cyclopropanecarboxamide

A mixture of 2-(5-bromo-3-methoxypicolinoyl)cyclopropanecarboxylic acid (1.00 g, 3.33 mmol), EDC.HCl (703 mg, 3.66 mmol) and HOBt (495 mg, 3.66 mmol) in DMF (10 ml) was stirred at rt for 6 h. A solution of aq ammonia (25%, 0.65 ml) was added at 0° C., and the reaction mixture was stirred an additional 18 h at rt. Extractive workup (EtOAc, 0.1 M aq HCl, water, brine) and concentration of the EtOAc extracts followed by column chromatography afforded the sub-title compound. Yield: 0.92 g (90%).

2-(5-Bromo-3-methoxypicolinoyl)cyclopropanecarbonitrile

Methanesulfonyl chloride (0.65 mL, 8.35 mmol) was added dropwise to a solution of 2-(5-bromo-3-methoxypicolinoyl)cyclopropanecarboxamid (490 mg, 1.64 mmol) in pyridine (3 mL) at 0° C. The reaction mixture was stirred at rt for 18 h and then poured into water (100 mL). Extractive workup (EtOAc, brine) and concentration of the EtOAc extracts followed by column chromatography afforded the sub-title compound. Yield: 377 mg (82%).

2-(5-((Cyclopropylmethyl)(naphthalen-1-yl)amino)-3-methoxypicolinoyl)cyclopropanecarbonitrile 2-(5-Bromo-3-methoxypicolinoyl)cyclopropanecarbonitrile (200 mg, 0.71 mmol), N-(cyclopropylmethyl)naphthalen-1-amine (158 mg, 0.85 mmol), Pd(OAc)$_2$ (8.1 mg, 0.036 mmol), rac-BINAP (31 mg, 0.040 mmol) and Cs$_2$CO$_3$ (325 mg, 1.00 mmol) were mixed in toluene (3 mL) and stirred at 70° C. for 60 h in a sealed tube. The reaction mixture was diluted with (EtOAc), filtered through celite pad and concentrated. Purification by column chromatography afforded the sub-title compound. Yield: 122 mg (43%).

(2-(1H-Tetrazol-5-yl)cyclopropyl)(5-((cyclopropylmethyl)(naphthalen-1-yl)amino)-3-methoxypyridin-2-yl)methanone 2-(5-((Cyclopropylmethyl)(naphthalen-1-yl)amino)-3-methoxypicolinoyl)cyclopropanecarbonitrile (110 mg, 0.28 mmol), NaN$_3$ (45 mg, 0.69 mmol) and triethylamine hydrochloride (95 mg, 0.69 mmol) were mixed in toluene (2 mL) and stirred at 95-110° C. for 18 h in a sealed tube. After cooling to rt the reaction mixture was acidified with 1M aq HCl (pH~5). Extractive workup (EtOAc, water, brine) and concentration of the EtOAc extracts followed by column chromatography afforded the title compound. Yield: 377 mg (82%). MS [M+H]$^+$ 441. $^1$H-NMR 400 MHz (CDCl$_3$:TFA, ppm) δ 8.60-8.30 (1H, br m), 8.07-7.94 (2H, m), 7.67-7.45 (5H, m), 6.40-6.10 (1H, br m), 4.30-3.22 (6H, m), 3.14-3.00 (1H, m), 2.04-1.87 (2H, m), 1.20-1.08 (1H, m), 0.62-0.46 (2H, m), 0.21-0.05 (2H, m).

The following compound was prepared in analogy to Example 60 described above in detail.

TABLE 11

| Ex. | Structure<br>Name<br>$^1$H-NMR | MS<br>[M + H]+ |
|---|---|---|
| 61 | ![structure]<br>(2-(1H-Tetrazol-5-yl)cyclopropyl)(5-((cyclopropylmethyl)(4-fluoronaphthalen-1-yl)amino)-3-methoxypyridin-2-yl)methanone<br>400 MHz (CDCl$_3$, ppm) δ 8.20 (1H, d, J = 8.5 Hz), 7.80-7.70 (1H, m), 7.68-7.57 (2H, m), 7.55-7.48 (1H, m), 7.44-7.38 (1H, m), 7.25-7.19 (1H, m), 6.33-6.24 (1H, m), 4.09-4.01 (1H, m), 3.97-3.87 (1H, m), 3.78 (3H, s), 3.53-3.42 (1H, m), 3.26-3.17 (1H, m), 2.03-1.95 (1H, m), 1.80-1.73 (1H, m), 1.22-1.12 (1H, m), 0.56-0.44 (2H, m), 0.15-0.05 (2H, m) | 459 |

Example 62

(1S,2S)-2-({5-[(5-Chloro-2,4-difluorophenyl)(2-fluoro-2-methylpropyl)amino]-3-methoxypyrazin-2-yl}carbonyl)cyclopropanecarboxylic acid

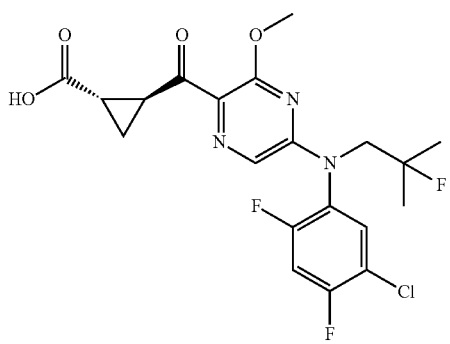 [SMILES: COc1nc(N(CC(C)(C)F)c2cc(Cl)c(F)cc2F)cnc1C(=O)[C@H]1C[C@@H]1C(=O)O]

(2-Ethoxy-2-oxoethyl)(dimethyl)sulfonium bromide

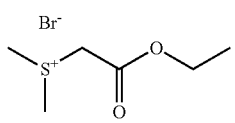

Into a 50-L 4-necked round-bottom flask, was placed acetone (25 L), ethyl 2-bromoacetate (10 kg, 59.88 mol, 1.00 equiv), (methylsulfanyl)methane (4.64 kg, 74.68 mol, 1.20 equiv). The resulting solution was stirred for 24 h at 20-30° C. The solids were collected by filtration. This resulted in 11.5 kg (84%) of (2-ethoxy-2-oxoethyl)(dimethyl)sulfonium bromide as a white solid.

trans-1, 2-Diethyl-cyclopropane-1,2-dicarboxylate $$\text{COOEt} \quad \text{COOEt}$$

Into a 50-L 4-necked round-bottom flask, was placed DMSO (30 L), (2-ethoxy-2-oxoethyl)(dimethyl)sulfonium bromide (11.50 kg, 50.19 mol, 1.00 equiv), potassium carbonate (7.62 kg, 55.14 mol, 1.10 equiv) The mixture was cooled to 15° C., and ethyl prop-2-enoate (7.03 kg, 70.22 mol, 1.40 equiv) was added slowly. The resulting solution was stirred for 14 h at 15-35° C., after which the solids were filtered out. The resulting solution was diluted with 90 L of water and extracted with 3×15 L of ethyl acetate after which the organic layers were combined and washed with 1×10 L of brine. The mixture was dried over anhydrous sodium sulfate. The solids were filtered out. The resulting mixture was concentrated under vacuum. The crude product was purified by distillation. This resulted in 4.9 kg (52%) of trans-1,2-diethyl-cyclopropane-1,2-dicarboxylate as colorless oil.

trans-2-(Ethoxycarbonyl)cyclopropane-1-carboxylic acid $$\text{COOH} \quad \text{COOEt}$$

Into a 50-L 4-necked round-bottom flask, was placed ethanol (18 L), trans-1,2-diethyl-cyclopropane-1,2-dicarboxylate (3750 g, 20.14 mol, 1.00 equiv), a solution of EtONa (1370.5 g, 1.00 equiv) in ethanol (5329 g) and water (725 g, 40.24 mol, 2.00 equiv). The resulting solution was stirred for 14 h at 20-25° C. The mixture was concentrated under vacuum, and the resulting solution diluted with 20 L of water. The resulting solution was extracted with 3×10 L of dichloromethane and the aqueous layers combined. The pH value of the solution was adjusted to 3-4 with hydrogen chloride (12 M). The resulting solution was extracted with 4×8 L of dichloromethane, the organic layers combined and washed with 1×5 L of brine. The mixture was dried over anhydrous sodium sulfate and concentrated under vacuum. The crude product was purified by re-crystallization from petroleum ether. This resulted in 2 kg (63%) of trans-2-(ethoxycarbonyl)cyclopropane-1-carboxylic acid as a yellow solid. $^1$H-NMR (300 MHz, DMSO-d$_6$) δ 1.15-1.34 (5H, m), 1.90-2.12 (2H, m), 4.04-4.13 (2H, m), 12.65 (1H, s).

trans-Ethyl 2-[methoxy(methyl)carbamoyl]cyclopropanecarboxylate

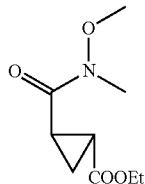

Into a 50-L 4-necked round-bottom flask was placed dichloromethane (24 L), trans 2-(ethoxycarbonyl)cyclopropane-1-carboxylic acid (4780 g, 30.22 mol, 1.00 equiv), (COCl)$_2$ (4200 g, 33.09 mol, 1.10 equiv), DMF (110.5 g, 1.51 mol, 0.05 equiv), DIEA (9750.5 g, 75.44 mol, 2.50 equiv), methoxyammonium chloride (3537 g, 36.26 mol, 1.20 equiv). The resulting solution was stirred for 5-7 h at 0-10° C. The resulting mixture was concentrated under vacuum. The residue was dissolved in 20 L of DCM and the mixture washed with 1×8 L of 1 M HCl, 1×5 L of NaHCO$_3$ (aq) and 1×5 L of brine. The mixture was dried over anhydrous sodium sulfate. The solids were filtered out. The resulting mixture was concentrated under vacuum. The crude product was purified by distillation. This resulted in 4100 g (67%) of trans-ethyl-2-[methoxy(methyl)carbamoyl] cyclopropanecarboxylate as colorless oil. $^1$H-NMR (300 MHz, CDCl$_3$) δ 1.30-1.46 (5H, m), 2.13-2.19 (1H, m), 2.68 (1H, s), 3.17-3.21 (3H, m), 3.74-3.76 (3H, m), 4.13-4.20 (2H, m).

5-bromo-2-iodo-3-methoxypyrazine

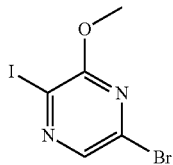

CH$_2$I$_2$ (9.2 kg, 34.3 mol, 2.0 eq), CuI (0.3 kg, 1.7 mol, 0.1 eq) and isopentyl nitrite (6.0 kg, 51.6 mol, 3.0 eq), were charged into a 50 L reactor. The mixture was heated up to 70-80° C. in an oil bath. A solution of 5-bromo-3-methoxypyrazin-2-amine (3.5 kg, 17.2 mol, 1.0 eq) in THF (17.5 L) was added dropwise into the glass flask at 70-80° C. for 150 min. After addition, the solution was stirred for 2 h at 70-80° C. The reaction was monitored by HPLC (starting material: product, 0.6%:63.1%). The mixture was cooled to room temperature and filtered. The filter cake was washed with EtOAc (7.0 L). The filtrates were combined with another batch (3.5 kg) and concentrated under vacuum (temperature: 40° C., vacuum: −0.08 Mpa). The residual was swapped twice with heptane (7.0 L×2). The organic layer was concentrated under vacuum (temperature: 40° C., vacuum: −0.08 Mpa). Heptane (17.5 L) was added to the residue. The mixture was heated to reflux in oil bath and filtered at high temperature to remove not dissolved material. A filter was performed at higher temperature. The filtrate was cooled to 0-10° C. and stirred for 2 h, yellow solid precipitated. The suspension was filtered and washed with heptane (1000 ml). The solid was dried under vacuum (temperature: 30° C., vacuum: −0.08 Mpa). Finally, 3.1 kg of product (purity: 95.3%, yield: 28.9%) was obtained as a yellow solid. $^1$H-NMR: (300 MHz, CDCl$_3$) δ 8.07 (s, 1H), 4.05 (s, 3H). MS ESI, m/z=314.9 (M+H)$^+$.

N-(5-chloro-2,4-difluorophenyl)-2-fluoro-2-methylpropanamide

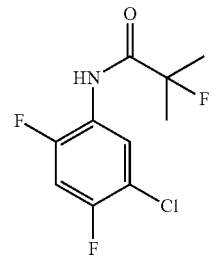 [SMILES: CC(C)(F)C(=O)Nc1cc(Cl)c(F)cc1F]

EtOAc (9.0 L), 5-chloro-2,4-difluorobenzenamine (1.0 kg, 6.1 mol, 1.0 eq), DMAP (820.3 g, 6.7 mol, 1.1 eq), DIEA (2.9 kg, 22.1 mol, 3.3 eq) was placed into a 20 L 4-neck flask. A solution of 2-fluoro-2-methylpropanoic acid (678.9 g, 6.4 mol, 1.05 eq) in EtOAc (1 L) was charged into reaction solution at 20-30° C. T$_3$P (50% in EtOAc, 4.3 kg, 6.7 mol, 1.1 eq) was added dropwise into the reaction solution at 20-30° C., during 20 min. The mixture was stirred for 2 h. The reaction was monitored by HPLC (starting material:product, 1.9%:89.6%). EtOAc (10 L), NaHCO$_3$ (aq) (10 L, 10% w/w) were charged into the reaction solution and stirred for 10-20 min. The mixture was separated and the organic layer was washed with NaHCO$_3$ (aq) (10 L, 10% w/w) once. The organic layer was washed with NaCl (aq) (10 L, 15% w/w) once. The organic layers were combined and concentrated under vacuum (temperature: 40° C., vacuum: −0.08 Mpa). The residual was swapped twice with isopropanol (10 L*2). The organic layers was concentrated under vacuum (temperature: 40° C., vacuum: −0.08 Mpa) until about 2-3 volumes left. The residual was cooled to 5-10° C. and stirred for 2-3 h, when a white solid precipitated. The suspension was filtered and washed with isopropanol (1000 ml). The solid was dried under vacuum (temperature: 30° C., vacuum: −0.08 Mpa) to obtain 1.3 kg of product (purity: 99%, yield: 84.4%) as a white solid. $^1$H-NMR (400 MHz, CDCl$_3$) δ 8.48-8.53 (t, 1H), 8.27 (s, 1H), 6.97-7.04 (m, 1H), 1.64-1.72 (d, 6H). MS ESI, m/z=252.1 (M+H)$^+$.

5-chloro-2,4-difluoro-N-(2-fluoro-2-methylpropyl) aniline

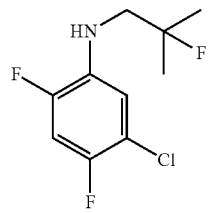

BH$_3$-DMS (1987 mL, 20.9 mol, 5.3 equiv), tetrahydrofuran (2.0 L) were charged into a 20 L 4-neck glass flask. A solution of N-(5-chloro-2,4-difluorophenyl)-2-fluoro-2- methylpropanamide (1000 g, 4.0 mol, 1.0 equiv) in THF (8.0 L) was added dropwise during about 6 h at 30-40° C. The resulting solution was stirred for 1-2 h at 30-40° C. The reaction progress was monitored by HPLC (starting material:product, 1.2%:88.6%). The reaction was then quenched by the addition of 10 L of water/ice. The resulting solution was extracted with 10 L of ethyl acetate and the organic layers were combined. The solution was washed with saturated solution of sodium bicarbonate (5 L, twice) and 5 L of saturated solution of NaCl (aq). The organic layer was combined with another batch (1.0 kg) and dried over anhydrous sodium sulfate and concentrated under vacuum (temperature: 40° C., vacuum: −0.08 Mpa). This resulted in 900 g (purity: 94%, yield: 95%) of 5-chloro-2,4-difluoro-N-(2-fluoro-2-methylpropyl)aniline as light yellow oil. $^1$H-NMR (400 MHz, CDCl$_3$) δ 7.28-7.34 (m, 1H), 6.94-6.98 (t, 1H), 5.67-5.69 (d, 1H), 3.25-3.34 (m, 2H), 1.31-1.36 (d, 6H). MS ESI, m/z=218.1 (M+H)$^+$.

Ethyl-2-[(5-bromo-3-methoxypyrazin-2-yl)carbonyl]cyclopropanecarboxylate

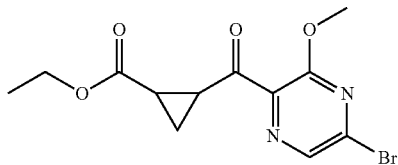 [SMILES: CCOC(=O)C1CC1C(=O)c1ncc(Br)nc1OC]

THF (24 L), 5-bromo-2-iodo-3-methoxypyrazine (2.4 kg, 7.6 mol, 1.0 eq) and racemic trans-ethyl 2-[methoxy(methyl)carbamoyl]cyclopropanecarboxylate (1.5 kg, 7.6 mol, 1.0 eq) were placed in a 50 L reactor. The reaction solution was cooled to −78° C. in an bath of liquid N$_2$ and EtOH. n-BuLi (2.5 M, 3.3 L, 8.4 mol, 1.1 eq) was added dropwise at this temperature during 1 h. The mixture was stirred for 30 min. The reaction was monitored by HPLC (starting material:product, 0.3%:65.8%). The reaction mixture was warmed to −10-0° C. and quenched by sat. NH$_4$Cl (aq) (7.2 L) at −5-5° C. The reaction mixture was extracted with EtOAc (7.2 L). The organic layer was washed with by sat. NH$_4$Cl (aq) (7.2 L) twice. The organic layer was combined with another batch (2.4 kg) and concentrated under vacuum (temperature: 40° C., vacuum: −0.08 Mpa) to obtain the crude product (8.9 kg) as a yellow oil. The crude product was purified by silica gel (EtOAc:petroleum ether=1:25) to obtain 2.2 kg of product (purity: 97.3%, yield: 44.0%) as light yellow solid. $^1$H-NMR: (400 MHz, CDCl$_3$) δ 8.37 (s, 1H), 4.17-4.22 (m, 2H), 4.12 (s, 3H), 3.67-3.72 (m, 1H), 2.35-2.40 (m, 1H), 1.62-1.65 (t, 2H), 1.24-1.32 (m, 3H). MS ESI, m/z=329.0 (M+H)$^+$.

Ethyl 2-({5-[(5-chloro-2,4-difluorophenyl)(2-fluoro-2-methylpropyl)amino]-3-methoxypyrazin-2-yl}carbonyl)cyclopropanecarboxylate

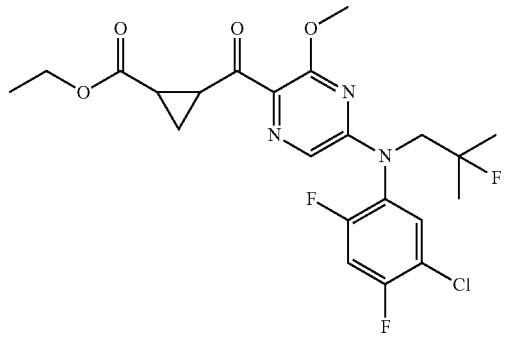 [SMILES: CCOC(=O)C1CC1C(=O)c1ncc(N(CC(C)(C)F)c2cc(Cl)c(F)cc2F)nc1OC]

THF (1000 mL), ethyl-2-[(5-bromo-3-methoxypyrazin-2-yl)carbonyl]cyclopropanecarboxylate (200 g, 607.6 mmol, 1.0 eq), 5-chloro-2,4-difluoro-N-(2-fluoro-2-methylpropyl)aniline (166 g, 698.5 mmol, 1.1 eq) were charged into 5 L 4-necked round-bottom flask, that was purged and maintained with an inert atmosphere of nitrogen. KHMDS (565.2 mL, 565 mmol, 0.9 eq) was added with dropwise at −5-5° C. during about 15 min. The resulting solution was stirred for 20 min at −5-5° C. in an ice/salt bath. The reaction progress was monitored by HPLC (starting material:product 3.1%:75.4%). The reaction was then quenched by the addition of 200 mL saturated solution of NH$_4$Cl (aq). The resulting solution was extracted with 600 mL of ethyl acetate and washed with 500 mL saturated solution of NH$_4$Cl (aq). The organic layer was washed with 500 mL saturated solution of NaCl (aq). The organic layer was dried over anhydrous sodium sulfate and concentrated under vacuum (temperature: 40° C., vacuum: −0.08 Mpa). The residue was purified by silica gel column with ethyl acetate/petroleum ether (1:10). This resulted in 180 g (97.3% purity, 61% yield) of ethyl 2-({5-[(5-chloro-2,4-difluorophenyl)(2-fluoro-2-methylpropyl)amino]-3-methoxypyrazin-2-yl}carbonyl)cyclopropanecarboxylate as a yellow solid. $^1$H-NMR (400 MHz, CDCl$_3$) δ 7.49-7.52 (t, 1H), 7.36 (s, 1H), 7.11-7.15 (t, 1H), 4.12-4.22 (m, 4H), 4.02 (s, 3H), 3.74-3.09 (m, 1H), 2.26-2.31 (m, 1H), 1.51-1.58 (m, 11H). MS ESI, m/z=472.3 (M+H)$^+$.

2-({5-[(5-Chloro-2,4-difluorophenyl)(2-fluoro-2-methylpropyl)amino]-3-methoxypyrazin-2-yl}carbonyl)cyclopropanecarboxylic acid

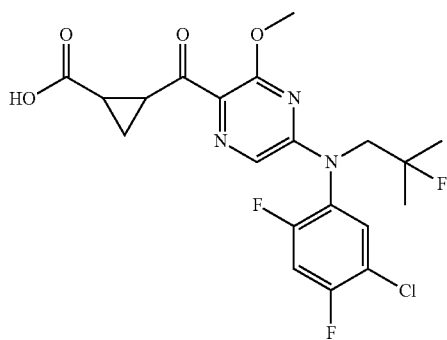 [SMILES: COc1nc(N(CC(C)(C)F)c2cc(Cl)c(F)cc2F)cnc1C(=O)C1CC1C(=O)O]

Tetrahydrofuran (6000 mL), ethyl 2-([5-[(5-chloro-2,4-difluorophenyl)(2-fluoro-2-methylpropyl)amino]-3-methoxypyrazin-2-yl]carbonyl)cyclopropanecarboxylate (2.0 kg, 4.12 mol, 1.0 eq), water (6 L), sodium hydroxide (329.3 g, 8.2 mol, 2.0 eq) were charged into a 20 L 4-necked round-bottom flask. The reaction solution was stirred for 16 h at 15-25° C. The reaction progress was monitored by HPLC (starting material:product=0.4%:98.5%). The pH value of the solution was adjusted to 3~4 with HCl (2 M). The resulting solution was extracted with 5 L of ethyl acetate and the organic layers combined and concentrated under vacuum (temperature: 40° C., vacuum: −0.08 Mpa) to obtain crude product. The crude product (1.98 kg) was charged into a 20 L 4-necked round-bottom flask. EtOAc (6.0 L) and hexane (6.0 L) were charged into the flask, the solid was not dissolved completely. The mixture slurry was stirred at 15-25° C. for 2 h. The solid was filtered and dried at 40-50° C. for 10 h. after that the solid was continued to dry at 70-80° C. for 10 h. This resulted in 1860 g (purity: 98%, yield: 96%) of 2-([5-[(5-chloro-2,4-difluorophenyl)(2-fluoro-2-methylpropyl)amino]-3-methoxypyrazin-2-yl]carbonyl)cyclopropanecarboxylic acid as a light yellow solid.

$^1$H-NMR (300 MHz, CDCl$_3$) δ 7.49 (t, 1H), 7.35 (s, 1H), 7.11 (t, 1H), 4.17 (d, 2H), 4.00 (s, 3H), 3.80 (m, 1H), 2.24 (m, 1H), 1.62 (m, 1H), 1.53 (m, 1H), 1.44 (d, 6H). MS ESI, m/z=458.2 (M+H)$^+$.

(1S,2S)-2-({5-[(5-Chloro-2,4-difluorophenyl)(2-fluoro-2-methylpropyl)amino]-3-methoxypyrazin-2-yl}carbonyl)cyclopropanecarboxylic acid

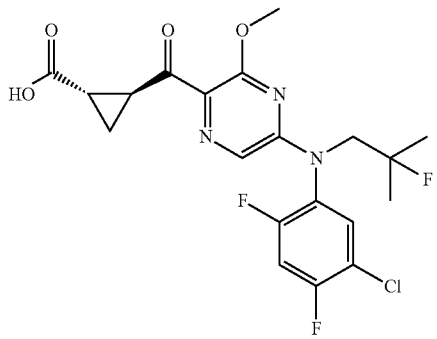 [SMILES: COc1nc(N(CC(C)(C)F)c2cc(Cl)c(F)cc2F)cnc1C(=O)[C@H]1C[C@@H]1C(=O)O]

The two enantiomers of 2-({5-[(5-chloro-2,4-difluorophenyl)(2-fluoro-2-methylpropyl)amino]-3-methoxypyrazin-2-yl}carbonyl)cyclopropanecarboxylic acid (2.3 Kg, 92% w/w, 4.62 mol) were separated on a SuperSep SFC fitted with a Chiralpak IC column (250×50 mm, 5 µm particle size) and 20% EtOH/FA 100/0.5 in CO$_2$, 120 bar as eluent to yield (1S,2S)-2-({5-[(5-chloro-2,4-difluorophenyl)(2-fluoro-2-methylpropyl)amino]-3-methoxypyrazin-2-yl}) carbonyl)cyclopropanecarboxylic acid and (1R,2R)-2-({5-[(5-chloro-2,4-difluorophenyl)(2-fluoro-2-methylpropyl)amino]-3-methoxypyrazin-2-yl}) carbonyl)cyclopropanecarboxylic acid. The enantiomer (1S,2S)-2-({5-[(5-chloro-2,4-difluorophenyl)(2-fluoro-2-methylpropyl)amino]-3-methoxypyrazin-2-yl}carbonyl)cyclopropanecarboxylic acid was suspended in heptane (5 L) and heated to 75° C. under slight reduced pressure (150-200 mbar) and the solvents removed (azeotroping the remaining formic acid from the separation). To the residue was added heptane (4 L) and isobutyl acetate (2 L) and the suspension stirred at 75° C. After stirring for one hour at 75° C. the temperature was decreased stepwise to 14° C. over 20 hours. Stirring continued at this temperature for another 20 hours. The obtained solid was filtered off and washed with heptane (2.5 L). Drying overnight at 40° C. in vacuo yielded (1S,2S)-2-({5-[(5-chloro-2,4-difluorophenyl)(2-fluoro-2-methylpropyl)amino]-3-methoxypyrazin-2-yl}carbonyl)cyclopropanecarboxylic acid [(1008 g, 2.2 mol, 98.9% w/w, LC purity 98.8% @ 230 nm, 99.9% ee, 47.6% yield, $[α]_D^{20}$=+62° (c 1.0, acetonitrile)] as a white solid. $^1$H-NMR (600 MHz, DMSO-d$_6$, 50° C.) δ 1.34 (m, 2H), 1.40 (d, J=21.6 Hz, 6H), 1.92 (ddd, J=8.4, 5.8, 3.9, Hz, 1H), 3.55 (ddd, J=8.6, 6.0, 3.9, Hz, 1H), 3.83 (s, 3H), 4.26 (d, J=21.8 Hz, 2H), 7.65 (br s, 1H), 7.71 (t, J=9.8 Hz, 1H), 7.98 (t, J=7.8 Hz, 1H), 12.34 (br s, 1H). $^{13}$C NMR (151 MHz, DMSO-d$_6$) δ 16.1, 23.9, 24.3 (br d, J=22.4 Hz), 25.3, 53.4, 57.4 (d, J=20.1 Hz), 96.9 (d, J=168.7 Hz), 106.6 (br t, J=27 Hz), 115.8 (br d, J=18.8 Hz), 121.4, 125.6, 127.8, 130.9, 153.7, 156.3 (dd, J=249.3, 11.9 Hz), 156.9 (dd, J=251.9, 11.2 Hz), 157.8, 173.0, 192.4. MS ESI, m/z=458.1105 (M+H)$^+$, (calc. 458.1094).

The solid residue was found to be crystalline by XRPD and a typical diffractogram is displayed in FIG. 1. Characteristic peak positions are listed in Table 12 and Table 13 below.

TABLE 12

| Five most characteristic peaks of Example 62 |
| --- |
| °2-theta |
| 4.8 |
| 19.4 |
| 22.8 |
| 24.6 |

TABLE 13

| Ten most characteristic peaks of Example 62 |
| --- |
| °2-theta |
| 4.8 |
| 9.4 |
| 11.5 |
| 13.3 |
| 16.3 |
| 19.4 |
| 22.8 |
| 24.6 |
| 25.5 |
| 27.7 |

Example 63

(1S,2S)-2-[(5-{(2-Fluoro-2-methylpropyl)[2-fluoro-5-(trifluoromethyl)phenyl]amino}-3-methoxy-pyrazin-2-yl)carbonyl]cyclopropanecarboxylic acid

2-Fluoro-N-(2-fluoro-5-(trifluoromethyl)phenyl)-2-methylpropanamide

T₃P (50% solution in EtOAc) (107 g, 167.49 mmol) was added to 2-fluoro-5-(trifluoromethyl)aniline (10 g, 55.83 mmol), 2-fluoro-2-methylpropanoic acid (6.52 g, 61.41 mmol) and DIPEA (39.0 mL, 223.32 mmol) in butyl acetate (60 mL) at 20° C. The resulting mixture was stirred at 80° C. for 30 min. The reaction mixture was poured into water (100 mL), extracted with EtOAc (2×100 mL), the organic layer was dried over Na₂SO₄, filtered and evaporated to afford brown solid. The crude product was purified by flash silica chromatography, elution gradient 0 to 1% EtOAc in petroleum ether. Pure fractions were evaporated to dryness to afford 2-fluoro-N-(2-fluoro-5-(trifluoromethyl)phenyl)-2-methylpropanamide (12.00 g, 80%) as a yellow solid.

¹H-NMR (400 MHz, CDCl₃) δ 1.68 (s, 3H), 1.73 (s, 3H), 7.20-7.31 (m, 1H), 7.40 (ddd, 1H), 8.48 (s, 1H), 8.77 (dd, 1H). MS ESI, m/z=268 (M+H)⁺.

2-Fluoro-N-(2-fluoro-2-methylpropyl)-5-(trifluoromethyl)aniline

BH₃THF (206 mL, 205.84 mmol) was added dropwise to 2-fluoro-N-(2-fluoro-5-(trifluoromethyl)phenyl)-2-methylpropanamide (11 g, 41.17 mmol) in THF (30 mL) at 0° C. over a period of 2 min under air. The resulting solution was stirred at 60° C. for 3 h. The reaction mixture was quenched with ice-water (50 mL), the reaction mixture was acidified with 2 M HCl. The reaction mixture was adjusted to pH 8-9 with saturated NaHCO₃ and was stirred at rt for 30 min, extracted with DCM (2×100 mL), the organic layer was dried over Na₂SO₄, filtered and evaporated to afford yellow liquid. The residue was purified by preparative TLC (petroleum ether:EtOAc=25:1), to afford 2-fluoro-N-(2-fluoro-2-methylpropyl)-5-(trifluoromethyl)aniline (5.30 g, 50.8%) as a yellow liquid. ¹H-NMR (400 MHz, CDCl₃) δ 1.47 (s, 3H), 1.52 (s, 3H), 3.33 (d, 2H), 6.93 (t, 2H), 7.07 (dd, 1H). MS ESI, m/z=254 (M+H)⁺.

trans-2-(Methoxycarbonyl)cyclopropane-1-carboxylic acid

A solution of LiOH.H₂O (40.6 g, 966.68 mmol) in MeOH (500 mL) was added to a stirred solution of trans-1,2-diethyl-cyclopropane-1,2-dicarboxylate (Example 62(b)) (180 g, 966.68 mmol) in THF (3000 mL) at 0° C. The resulting solution was stirred at 20° C. for 16 hours. The solvent was removed under reduced pressure. The reaction mixture was diluted with H₂O (400 mL). The reaction mixture was adjusted to pH=3-4 with 2 M HCl. The reaction mixture was extracted with DCM (6×500 mL), the organic layer was dried over Na₂SO₄, filtered and evaporated to afford yellow oil. The product was used in the next step directly without further purification. ¹H NMR (400 MHz, CDCl₃, 23° C.) δ 1.47-1.53 (m, 2H), 2.15-2.26 (m, 2H), 3.70 (s, 3H), 11.26 (s, 1H).

trans Methyl 2-(chlorocarbonyl)cyclopropanecarboxylate

Oxalyl dichloride (197 g, 1554.20 mmol) was added to trans-2-(methoxycarbonyl)cyclopropane-1-carboxylic acid (112 g, 777.10 mmol), DMF (8 mL, 103.32 mmol) and in DCM (1200 mL) at 0° C. under nitrogen. The resulting solution was stirred at 20° C. for 5 h. The solvent was removed under reduced pressure. The compound (112 g, 89%) was used in the next step directly without further purification.

Methyl 2-[methoxy(methyl)carbamoyl]cyclopropanecarboxylate

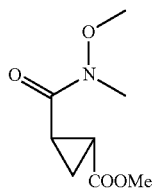

A mixture of trans methyl 2-(chlorocarbonyl)cyclopropanecarboxylate (112 g, 688.93 mmol) in DCM (300 mL) was added dropwise to a stirred mixture of N,O-dimethylhydroxylamine hydrochloride (101 g, 1033.39 mmol) and triethylamine (279 g, 2755.72 mmol) in DCM (2000 mL) at 0° C., over a period of 30 min under nitrogen. The resulting mixture was stirred at 20° C. for 15 h. The reaction mixture was washed with saturated NaHCO$_3$ (500 mL×4). The organic layer was dried over Na$_2$SO$_4$, filtered and evaporated to afford crude product. The crude product was purified by flash silica chromatography, elution gradient 0 to 10% EtOAc in petroleum ether. Pure fractions were evaporated to dryness to afford methyl 2-[methoxy(methyl)carbamoyl] cyclopropanecarboxylate (80 g, 62.3%) as a yellow liquid. $^1$H NMR (300 MHz, CDCl$_3$, 27° C.) δ 1.40-1.48 (m, 2H, 2.15-2.21 (m, 1H), 2.69 (s, 1H), 3.21 (s, 3H), 3.71-3.75 (d, 6H).

Methyl 2-[(5-bromo-3-methoxypyrazin-2-yl)carbonyl]cyclopropanecarboxylate

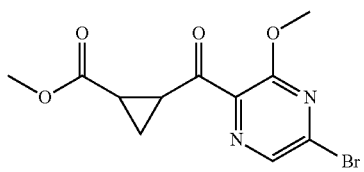 [SMILES: COC(=O)C1CC1C(=O)c1ncc(Br)nc1OC]

Isopropylmagnesium chloride-LiCl complex (242 mL, 314.38 mmol) was added dropwise to 5-bromo-2-iodo-3-methoxypyrazine (90 g, 285.8 mmol) in THF (1500 mL) at −70° C. over a period of 5 min under nitrogen. The resulting solution was stirred at −50° C. for 40 min. Methyl 2-[methoxy(methyl)carbamoyl]cyclopropanecarboxylate (53.5 g, 285.80 mmol) in THF (150 mL) was added at −70° C. The resulting solution was stirred at −10° C. for 1 hour. The reaction mixture was quenched with saturated NH$_4$Cl (300 mL), extracted with DCM (3×500 mL), the organic layer was dried over Na$_2$SO$_4$, filtered and evaporated to afford a red liquid. The crude product was purified by flash silica chromatography, elution gradient 0 to 10% EtOAc in petroleum ether. Pure fractions were evaporated to dryness to afford methyl 2-[(5-bromo-3-methoxypyrazin-2-yl)carbonyl]cyclopropanecarboxylate (37.0 g, 41.1%) as a white solid.

$^1$H NMR (300 MHz, CDCl$_3$, 27° C.) δ 1.56-1.65 (m, 2H), 2.32-2.38 (m, 1H), 3.65-3.72 (m, 4H), 4.09 (s, 3H), 8.35 (s, 1H). MS (ESI): m/z=315 [M+H]$^+$

Methyl 2-[(5-(2-fluoro-2-methylpropyl)[2-fluoro-5-(trifluoromethyl)phenyl]amino-3-methoxypyrazin-2-yl)carbonyl]cyclopropanecarboxylate

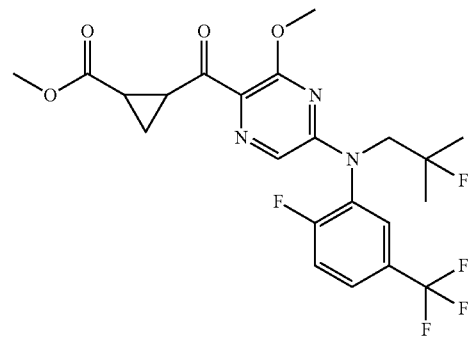 [SMILES: COC(=O)C1CC1C(=O)c1ncc(N(CC(C)(C)F)c2cc(C(F)(F)F)ccc2F)nc1OC]

KHMDS (12.55 mL, 11.42 mmol) was added to 2-fluoro-N-(2-fluoro-2-methylpropyl)-5-(trifluoromethyl)aniline (2.411 g, 9.52 mmol), methyl 2-[(5-bromo-3-methoxy-pyrazin-2-yl)carbonyl]cyclopropanecarboxylate (3 g, 9.52 mmol) in THF (10 mL) at −20° C. over a period of 2 minutes under N$_2$ (g). The resulting solution was stirred at −20° C. for 5 min. The reaction mixture was poured into ice (20 mL), extracted with EtOAc (2×50 mL), the organic layer was dried over Na$_2$SO$_4$, filtered and evaporated to afford orange oil. The residue was purified by preparative TLC (petroleum ether: EtOAc=4:1), to afford methyl 2-[(5-{(2-fluoro-2-methylpropyl) [2-fluoro-5-(trifluoromethyl)phenyl]amino}-3-methoxypyrazin-2-yl)carbonyl]cyclopropanecarboxylate (4.30 g, 93%) as a pale yellow oil. $^1$H-NMR (400 MHz, CDCl$_3$) δ 1.44 (s, 3H), 1.47-1.62 (m, 5H, 2.25-2.34 (m, 1H), 3.69 (s, 3H), 3.73-3.83 (m, 1H), 4.02 (s, 3H), 4.23 (s, 1H), 4.28 (s, 1H), 7.33-7.44 (m, 2H), 7.72 (t, 2H). MS ESI, m/z=488 (M+H)$^+$.

2-[(5-{(2-Fluoro-2-methylpropyl)[2-fluoro-5-(trifluoromethyl)phenyl]amino}-3-methoxypyrazin-2-yl)carbonyl]cyclopropanecarboxylic acid

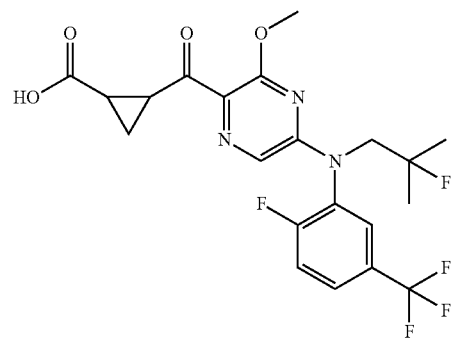 [SMILES: COc1nc(N(CC(C)(C)F)c2cc(C(F)(F)F)ccc2F)cnc1C(=O)C1CC1C(=O)O]

A solution of NaOH (2.95 g, 73.86 mmol) in water (20 mL) was added dropwise to a stirred solution of methyl 2-[(5-{(2-fluoro-2-methylpropyl)[2-fluoro-5-(trifluoromethyl)phenyl]amino}-3-methoxypyrazin-2-yl)carbonyl]cyclopropanecarboxylate (3.6 g, 7.39 mmol) in MeOH (350 mL) at 0° C. The resulting solution was stirred at 20° C. for 36 h. The reaction mixture was poured into ice-water (1 L), extracted with DCM (2×1 L), the organic layer was dried over Na₂SO₄, filtered and evaporated to afford 2-[(5-{(2-fluoro-2-methylpropyl)[2-fluoro-5-(trifluoromethyl)phenyl]amino}-3-methoxypyrazin-2-yl)carbonyl]cyclopropanecarboxylic acid (3.24 g, 93%) as a pale yellow solid. MS ESI, m/z=474 (M+H)⁺.

(1S,2S)-2-[(5-{(2-Fluoro-2-methylpropyl)[2-fluoro-5-(trifluoromethyl)phenyl]amino}-3-methoxypyrazin-2-yl)carbonyl]cyclopropanecarboxylic acid

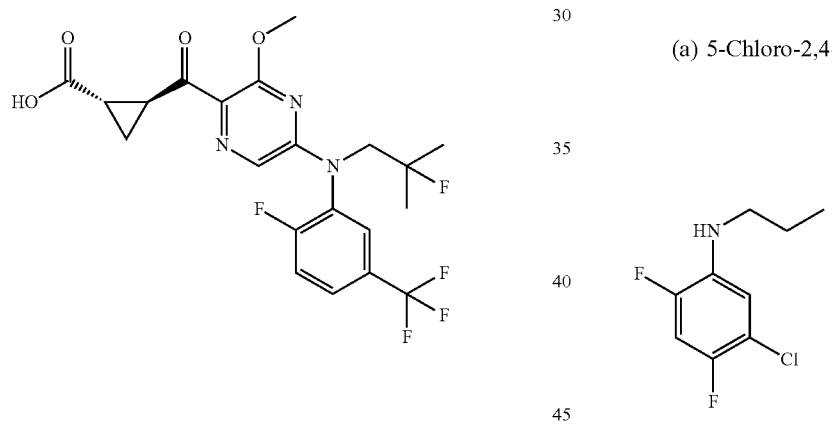

2-[(5-{(2-fluoro-2-methylpropyl)[2-fluoro-5-(trifluoromethyl)phenyl]amino}-3-methoxypyrazin-2-yl)carbonyl]cyclopropanecarboxylic acid product was purified by preparative SFC on a Chiralpak IA column, eluting isocratically with 30% MeOH in CO₂ (modified with 0.05% AcOH) as eluent. The fractions containing the desired compound (first eluting isomere) were evaporated to dryness to afford (1S,2S)-2-[(5-{(2-fluoro-2-methylpropyl) [2-fluoro-5-(trifluoromethyl)phenyl]amino}-3-methoxypyrazin-2-yl)carbonyl] cyclopropanecarboxylic acid (1.200 g, 32.4%) as a white solid.

1H-NMR (400 MHz, DMSO-d₆) δ 1.30-1.41 (m, 5H), 1.43 (s, 3H), 1.87-1.96 (m, 1H), 3.57 (ddd, 1H), 3.78 (s, 3H), 4.30-4.36 (d, 2H), 7.64 (t, 2H), 7.86 (d, 1H), 8.13 (d, 1H), 12.49 (s, 1H). MS ESI, m/z=474 (M+H)⁺.

Example 64

(1S,2S)-2-({5-[(5-Chloro-2,4-difluorophenyl)(propyl)amino]-3-methoxypyrazin-2-yl}carbonyl)cyclopropanecarboxylic acid

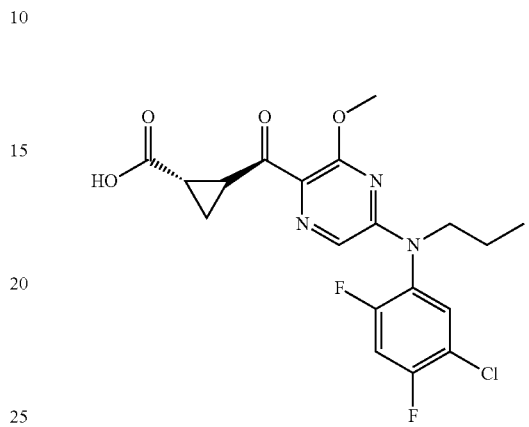

(a) 5-Chloro-2,4-difluoro-N-propylaniline

Propionaldehyde (178 mg, 3.06 mmol) was added dropwise to 5-chloro-2,4-difluoroaniline (500 mg, 3.06 mmol) in 1,2-dichloroethane (5 mL) at 20° C. The resulting solution was stirred at 20° C. for 2 h. The reaction was cooled to 0° C. after which sodium triacetoxyborohydride (1296 mg, 6.11 mmol) was added slowly. The resulting mixture was stirred at 20° C. overnight. The reaction mixture was diluted with EtOAc (100 mL), and washed sequentially with water (75 mL), saturated NaHCO₃ (2×100 mL). The organic layer was dried over Na₂SO₄, filtered and evaporated to afford crude product. The residue was purified by preparative TLC (petroleum ether: EtOAc=20:1), to afford 5-chloro-2,4-difluoro-N-propylaniline (266 mg, 42.3%) as a yellow liquid.

¹H-NMR (300 MHz, CDCl₃) δ 0.98-1.03 (t, 3H), 1.62-1.72 (m, 2H), 3.03-3.08 (t, 2H), 6.61-6.64 (t, 1H), 6.83-6.87 (t, 1H).

MS ESI, m/z=206 (M+H)⁺.

(b) Methyl 2-({5-[(5-chloro-2,4-difluorophenyl)(propyl)amino]-3-methoxypyrazin-2-yl}carbonyl)cyclopropanecarboxylate

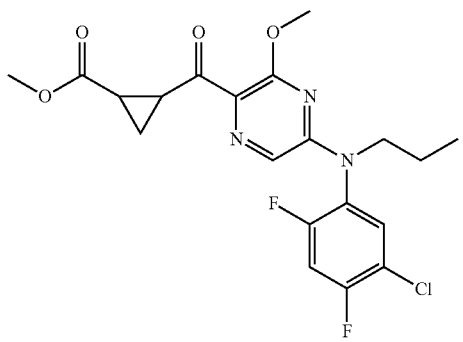 [SMILES: CCCN(c1cnc(C(=O)C2CC2C(=O)OC)c(OC)n1)c1cc(Cl)c(F)cc1F]

Potassium bis(trimethylsilyl)amide (0.837 mL, 0.76 mmol) was added dropwise to methyl 2-[(5-bromo-3-methoxypyrazin-2-yl)carbonyl]cyclopropanecarboxylate (Example 63 (f)) (200 mg, 0.63 mmol) and 5-chloro-2,4-difluoro-N-propylaniline (157 mg, 0.76 mmol) in THF (15 mL) at −20° C. over a period of 10 minutes under nitrogen. The resulting mixture was stirred at −20° C. for 30 min. The reaction mixture was quenched with ice-water (100 mL), extracted with EtOAc (3×100 mL), the organic layer was dried over $Na_2SO_4$, filtered and evaporated to afford a red liquid. The residue was purified by preparative TLC (petroleum ether:EtOAc, 2:1), to afford methyl 2-({5-[(5-chloro-2,4-difluorophenyl)(propyl)amino]-3-methoxypyrazin-2-yl}carbonyl)cyclopropanecarboxylate (145 mg, 51.9%) as a yellow oil.

MS ESI, m/z=440 $(M+H)^+$.

(c) 2-({5-[(5-Chloro-2,4-difluorophenyl)(propyl)amino]-3-methoxypyrazin-2-yl}carbonyl)cyclopropanecarboxylic acid

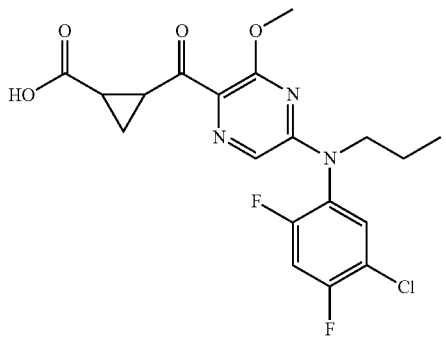 [SMILES: CCCN(c1cnc(C(=O)C2CC2C(=O)O)c(OC)n1)c1cc(Cl)c(F)cc1F]

A solution of lithium hydroxide hydrate (267 mg, 6.37 mmol) in water (0.5 mL) was added dropwise to a stirred mixture of methyl 2-({5-[(5-chloro-2,4-difluorophenyl)(propyl)amino]-3-methoxypyrazin-2-yl}carbonyl)cyclopropanecarboxylate (140 mg, 0.32 mmol) in MeOH (2 mL) cooled to 0° C., over a period of 10 min under air. The resulting mixture was stirred at 60° C. for 1 h. The reaction mixture was poured into ice (100 mL), the reaction mixture was adjusted to pH 3-4 with 2 M HCl, extracted with DCM (3×100 mL), the organic layer was dried over $Na_2SO_4$, filtered and evaporated to afford a yellow solid. The crude product was purified by preparative HPLC (XSelect CSH Prep C18 OBD column, 5μ silica, 19 mm diameter, 150 mm length), using decreasingly polar mixtures of water (containing 0.1% formic acid) and MeCN as eluents. Fractions containing the desired compound were evaporated to dryness to afford 2-({5-[(5-chloro-2,4-difluorophenyl)(propyl)amino]-3-methoxypyrazin-2-yl}carbonyl)cyclopropanecarboxylic acid (119 mg, 88%) as a yellow solid.

MS ESI, m/z=426 $(M+H)^+$.

(d) (1S,2S)-2-({5-[(5-Chloro-2,4-difluorophenyl)(propyl)amino]-3-methoxypyrazin-2-yl}carbonyl)cyclopropanecarboxylic acid

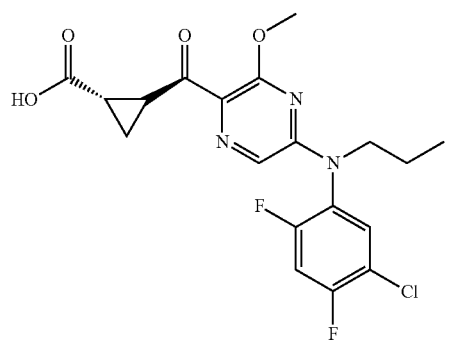

2-({5-[(5-Chloro-2,4-difluorophenyl)(propyl)amino]-3-methoxypyrazin-2-yl}carbonyl)cyclopropanecarboxylic acid was purified by preparative chiral-HPLC on a Chiralpak IB column, eluting isocratically with 30% EtOH in hexane (modified with 0.1% HAc) as eluent. The fractions containing the desired compound (first isomer) were evaporated to dryness to afford (1S,2S)-2-({5-[(5-chloro-2,4-difluorophenyl)(propyl)amino]-3-methoxypyrazin-2-yl}carbonyl)cyclopropanecarboxylic acid (50.0 mg, 42.0%) as a yellow solid.

$^1$H-NMR (400 MHz, $CD_3OD$) δ 1.00 (m, 3H), 1.44-1.49 (m, 2H), 1.69-1.78 (m, 2H), 2.07-2.12 (m, 1H), 3.73-3.98 (m, 6H), 7.42-7.47 (t, 2H), 7.74-7.78 (t, 1H).

MS ESI, m/z=426 $(M+H)^+$.

Example 65

(1S,2S)-2-[(5-{[2-Fluoro-5-(trifluoromethyl)phenyl](2-methylpropyl)amino}-3-methoxypyridin-2-yl)carbonyl]cyclopropanecarboxylic acid

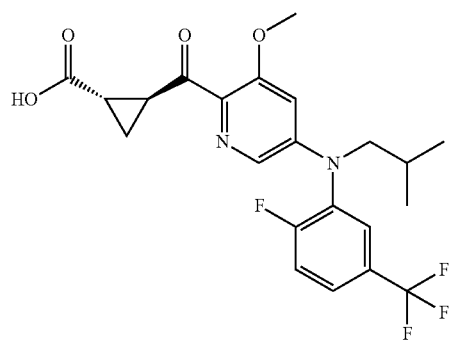 [SMILES: COc1cc(N(CC(C)C)c2cc(C(F)(F)F)ccc2F)cnc1C(=O)[C@H]1C[C@@H]1C(=O)O]

(a) 2-fluoro-N-isobutyl-5-(trifluoromethyl)aniline

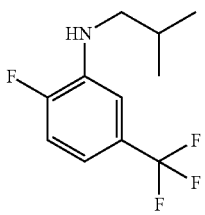 [SMILES: CC(C)CNc1cc(C(F)(F)F)ccc1F]

Isobutyryl chloride (1.12 mL, 10.7 mmol) was added in portions to 2-fluoro-5-(trifluoromethyl)aniline (1.79 g, 10.0 mmol) in DCM (50 ml) and TEA (1.49 mL, 10.7 mmol) stirred at rt. After 15 minutes the reaction was partitioned between aq (100 ml) with conc. HCl (5 mL) and EtOAc/heptane: 1/1. The organic phase was evaporated to dryness and heated in $BH_3$-THF at 55° C. overnight under $N_2$. After cooling the reaction was quenched in aq (150 mL) with some $NH_3$ (aq). Extraction with EtOAc/heptane: 1/1 and evaporation afforded the title compound 2-fluoro-N-isobutyl-5-(trifluoromethyl)aniline (2.03 g, 86% yield) as a colourless oil.

$^1$H-NMR (500 MHz, DMSO-$d_6$) δ 0.91 (d, 6H), 1.88 (dp, 1H), 2.86-2.99 (m, 2H), 5.69-6.37 (m, 1H), 6.8-6.85 (m, 1H), 6.87 (dd, 1H), 7.19 (dd, 1H).

(b) (1S,2S)-2-[(5-{[2-fluoro-5-(trifluoromethyl)phenyl](2-methylpropyl)amino}-3-methoxypyridin-2-yl)carbonyl]cyclopropanecarboxylic acid

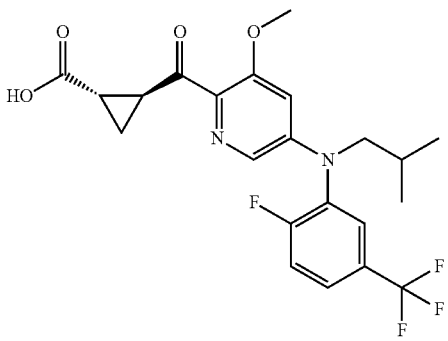 [SMILES: COc1cc(N(CC(C)C)c2cc(C(F)(F)F)ccc2F)cnc1C(=O)[C@H]1C[C@@H]1C(=O)O]

To a 50 ml round bottom flask ethyl-2-(5-bromo-3-methoxypicolinoyl)cyclopropanecarboxylate (Int 3:1) (0.492, 1.5 mmol), 2-fluoro-N-isobutyl-5-(trifluoromethyl)aniline (0.353 g, 1.5 mmol), cesium carbonate (0.746 g, 2.3 mmol), BINAP (0.187 g, 0.30 mmol) and Pd(OAc)$_2$ (0.067 g, 0.30 mmol). After toluene (15 mL) was added the stirred reaction mixture was deoxygenated ($N_2$ bubbling) and heated to 110° C. on a oil bath for 24 hours under nitrogen. After cooling and evaporation the crude material was dissolved in a small amount EtOAc and elated through a SiO$_2$ plug (ca 10 cm$^3$). The SiO$_2$ was washed with EtOAc/heptane 1/1 mixture (ca 100 mL) and the combined eluates was evaporated to dryness to afford a colourless oil. The oil was solved in THF (10 ml) methanol (5 ml) and water (5 ml). Lithium hydroxide (0.113 g, 4.7 mmol) was added and the esterhydrolysis was allowed to proceed 1.5 hours at rt.

The reaction was quenched with acetic acid (0.6 ml) and evaporated. Preparative HPLC as described in general methods followed by chiral chromatography (Chiralpak 1C, 250×20 mm, heptane/EtOH/TEA:60/40/0.1) afforded the title compound (1S,2S)-2-[(5-{[2-fluoro-5-(trifluoromethyl)phenyl](2-methylpropyl)amino}-3-methoxypyridin-2-yl)carbonyl]cyclopropanecarboxylic acid (0.107 g, 0.24 mmol) in 16% yield as a white solid.

$^1$H NMR (500 MHz, DMSO-$d_6$) δ 0.93 (d, 6H), 1.26-1.37 (m, 2H), 1.83-1.98 (m, 2H), 3.53-3.64 (m, 1H), 3.74 (d, 2H), 3.75 (s, 3H), 6.69 (d, 1H), 7.55-7.72 (m, 2H), 7.83 (d, 1H), 8.02 (d, 1H), 12.45 (s, 1H).

MS ESI, m/z=455.4 (M+H)$^+$.

Optical rotation (1 g/100 ml, acetonitrile, 20° C., 589 nm)=+44°

Biological Tests

Abbreviations

DMSO dimethyl sulphoxide
GSH glutathione
PBS phosphate buffered saline

In Vitro hLTC$_4$ Synthase Enzyme Assay (Test A)

In the assay, LTC$_4$ synthase catalyses the reaction where the substrate LTA$_4$ is converted to LTC$_4$. Recombinant human LTC$_4$ synthase is expressed in *Piccia pastoralis* and the purified enzyme is dissolved in 25 mM tris-buffer pH 7.8 supplemented with 0.1 mM glutathione (GSH) and stored at −80° C.

In order to obtain IC$_{50}$-values for the compounds, the following procedure was used:

A volume (24 µL) of 0.25 µg/mL LTC$_4$ synthase in 75 mM tris (pH~8.5), 0.5 mM MgCl$_2$ and 3 mM GSH was preincubated for 10 min with 0.5 µL of compound of interest in DMSO at ten different concentrations, typically in the range $10^{-9.5}$-$10^{-5}$ M as well as with DMSO only. The buffer is used as background. Runs are performed in duplicates.

The enzymatic reaction is initiated by addition of 0.5 µL LTA$_4$ in diglyme (final assay concentration 8 µM).

The reaction is stopped after 1 min by addition of double the reaction volume of a stop solution (MeOH:H$_2$O:acetic acid 70:30:1).

After 15 fold dilution in PBS, LTC$_4$ formation is detected with LTC$_4$ HTRF kit (Cisbio, cat. No 64LC4PEC) and a fluorescence reader. Typically 6 µL of sample is mixed with 3 µL of each of the HTRF reagents d2 and k and analyzed as described in the kit manual.

The detected product concentration, with background subtracted, is plotted versus compound concentration and IC$_{50}$ is determined as 50% of maximum inhibition.

In Vitro hLTC$_4$ Synthase Enzyme Assay (Test B)

In the assay, LTC$_4$ synthase catalyses the reaction where the substrate LTA$_4$ methyl ester is converted to LTC$_4$ methyl ester.

In order to obtain IC$_{50}$-values for the compounds, the following procedure was used:

10 mL of 0.6 nM of human recombinant purified LTC$_4$ synthase expressed from *Pichia Pastoris* in buffer 50 mM tris (pH 7.5), 0.05% BSA 0.03% DD M 100 mM NaCl was preincubated for 30 min with 10 mL of substrate mix containing 6 mM LTA4-methyl ester substrate and 1 mM glutathione in 50 mM Tris pH7.5 0.05% BSA 0.03% DDM 100 mM NaCl together with 0.1 µL of compound of interest in DMSO at ten different concentrations, typically in the range $10^{-9.5}$-$10^{-5}$ M as well as with DMSO only.

The enzymatic reaction is initiated by addition of 10 µL LTC4S enzyme solution to 10 µL substrate solution to the assay plate containing 0.5 mL of compound in DMSO or 0.5 mL DMSO control- The reaction is stopped after 30 min by addition of 40 µL 75% (w/v) acetonitrile in H$_2$O.

After stopping the reaction the LTC4 methyl ester product was detected by LCMSMS, The detected product concentration, with background subtracted, is plotted versus compound concentration and $IC_{50}$ is determined as 50% of maximum inhibition.

Compounds of the invention have been tested in the above assay and have shown to be $LTC_4$ synthase inhibitors as shown in Table A below. The $IC_{50}$-values presented in Table A below are median values of at least two determinations. The values for Examples 1-61 were generated by Test A, and the values from Examples 62-65 were generated by Test B.

TABLE A

| Ex. | $hLTC_4$ synthase $IC_{50}$ [nM] |
|---|---|
| 1 | 18 |
| 2 | 86 |
| 3 | 149 |
| 4 | 263 |
| 5 | 38 |
| 6 | 47 |
| 7 | 18 |
| 8 | 279 |
| 9 | 24 |
| 10 | 445 |
| 11 | 35 |
| 12 | 28 |
| 13 | 34 |
| 14 | 22 |
| 15 | 171 |
| 16 | 800 |
| 17 | 34 |
| 18 | 39 |
| 19 | 105 |
| 20 | 88 |
| 21 | 53 |
| 22 | 112 |
| 23 | 1839 |
| 24 | 2178 |
| 25 | 66 |
| 26 | 478 |
| 27 | 588 |
| 28 | 67 |
| 29 | 370 |
| 30 | 152 |
| 31 | 331 |
| 32 | 1671 |
| 33 | 185 |
| 34 | 19 |
| 35 | 229 |
| 36 | 9 |
| 37 | 25 |
| 38 | 31 |
| 39 | 68 |
| 40 | 356 |
| 41 | 81 |
| 42 | 277 |
| 43 | 74 |
| 44 | 56 |
| 45 | 62 |
| 46 | 26 |
| 47 | 61 |
| 48 | 46 |
| 49 | 65 |
| 50 | 75 |
| 51 | 68 |
| 52 | 359 |
| 53 | 152 |
| 54 | 424 |
| 55 | 636 |
| 56 | 17 |
| 57 | 50 |
| 58 | 19 |
| 59 | 18 |
| 60 | 96 |
| 61 | 39 |
| 62 | 0.289 |
| 63 | 0.248 |
| 64 | 0.483 |
| 65 | 0.658 |

The invention claimed is:

1. A compound which is (1 S,2S)-2-({5-[(5-Chloro-2,4-difluorophenyl)(2-fluoro-2-methylpropyl)amino]-3-methoxypyrazin-2-yl}carbonyl)cyclopropanecarboxylic acid:

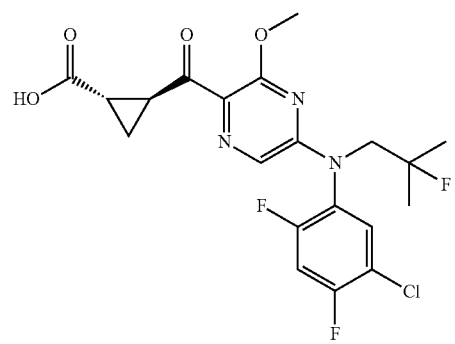 [SMILES: COc1nc(N(CC(C)(C)F)c2cc(Cl)c(F)cc2F)cnc1C(=O)[C@H]1C[C@@H]1C(=O)O]

or a pharmaceutically-acceptable salt thereof.

2. A pharmaceutical formulation, wherein the formulation comprises the compound of claim 1, or a pharmaceutically acceptable salt thereof, in admixture with a pharmaceutically acceptable adjuvant, diluent or carrier.

3. A compound which is (1 S,2S)-2-({5-[(5-Chloro-2,4-difluorophenyl)(2-fluoro-2-methylpropyl)amino]-3-methoxypyrazin-2-yl}carbonyl)cyclopropanecarboxylic acid:

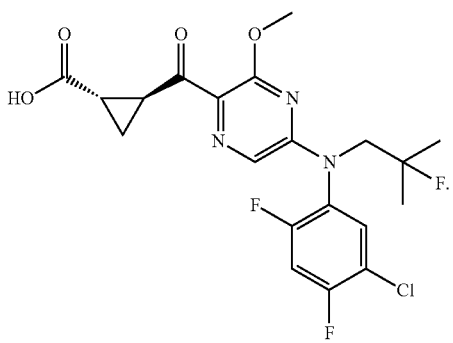

4. A pharmaceutical formulation, wherein the formulation comprises the compound of claim 3, in admixture with a pharmaceutically acceptable adjuvant, diluent or carrier.

* * * * *